US012064730B2

(12) United States Patent
Rasmussen et al.

(10) Patent No.: US 12,064,730 B2
(45) Date of Patent: Aug. 20, 2024

(54) POLYMERIC SUBSTRATES WITH ATTACHED POLYMERIC CHAINS

(71) Applicant: Solventum Intellectual Properties Company, Maplewood, MN (US)

(72) Inventors: Jerald K. Rasmussen, Woodville, WI (US); Stephen B. Roscoe, Woodbury, MN (US); Babu N. Gaddam, Woodbury, MN (US); George W. Griesgraber, Eagan, MN (US); Daniel J. O'Neal, St. Paul, MN (US); Eli P. Narveson, St. Louis Park, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 91 days.

(21) Appl. No.: 15/733,205

(22) PCT Filed: Dec. 14, 2018

(86) PCT No.: PCT/IB2018/060120
§ 371 (c)(1),
(2) Date: Jun. 10, 2020

(87) PCT Pub. No.: WO2019/123177
PCT Pub. Date: Jun. 27, 2019

(65) Prior Publication Data
US 2020/0368694 A1   Nov. 26, 2020

Related U.S. Application Data

(60) Provisional application No. 62/608,184, filed on Dec. 20, 2017.

(51) Int. Cl.
*B01D 67/00* (2006.01)
*B01D 69/02* (2006.01)
*B01D 69/10* (2006.01)
*C08J 7/18* (2006.01)
*C12M 1/00* (2006.01)
*G01N 33/543* (2006.01)
*G01N 33/545* (2006.01)

(52) U.S. Cl.
CPC ... *B01D 67/0006* (2013.01); *B01D 67/00931* (2022.08); *B01D 69/02* (2013.01); *B01D 69/105* (2013.01); *B01D 69/1071* (2022.08); *C08J 7/18* (2013.01); *C12M 29/04* (2013.01); *G01N 33/54393* (2013.01); *G01N 33/545* (2013.01); *B01D 2323/38* (2013.01); *C08J 2377/02* (2013.01)

(58) Field of Classification Search
CPC ........... B01D 67/0006; B01D 67/0093; B01D 69/02; B01D 69/105; B01D 2323/38; B01D 2323/40; B01D 2325/14; B01D 39/1623; B01D 69/10; C08J 7/18; C08J 2377/02; C12M 29/04; G01N 33/54393; G01N 33/545; B01J 20/28033; B01J 20/3212; B01J 20/3217; B01J 20/3251; B01J 20/3297; C07K 1/00

See application file for complete search history.

(56) References Cited

U.S. PATENT DOCUMENTS

| | | | |
|---|---|---|---|
| 3,876,738 A | 4/1975 | Marinaccio | |
| 3,928,517 A | 12/1975 | Knight | |
| 4,330,590 A | 5/1982 | Vesley | |
| 4,539,256 A | 9/1985 | Shipman | |
| 4,707,265 A | 11/1987 | Barnes, Jr. | |
| 4,726,989 A | 2/1988 | Mrozinski | |
| 4,867,881 A | 9/1989 | Kinzer | |
| 4,968,532 A * | 11/1990 | Janssen | C08J 7/16 427/322 |
| 5,120,594 A | 6/1992 | Mrozinski | |
| 5,260,360 A | 11/1993 | Mrozinski | |
| 5,458,782 A | 10/1995 | Hou | |
| 5,962,544 A | 10/1999 | Waller, Jr. | |
| 6,056,529 A | 5/2000 | Meyering | |
| 6,267,916 B1 | 7/2001 | Meyering | |
| 6,413,070 B1 | 7/2002 | Meyering | |
| 6,512,081 B1 | 1/2003 | Rizzardo | |
| 6,776,940 B2 | 8/2004 | Meyering | |

(Continued)

FOREIGN PATENT DOCUMENTS

| | | |
|---|---|---|
| EP | 0142810 | 5/1985 |
| JP | S47-040913 | 10/1972 |

(Continued)

OTHER PUBLICATIONS

Barner et al., Reversible Addition—Fragmentation Chain-Transfer Graft Polymerization of Styrene: Solid Phases for Organic and Peptide Synthesis, 40 J. Polym. Sci. A1, 4180, 4180-4192 (2002). (Year: 2002).*
Barner, "Reversible Addition—Fragmentation Chain-Transfer Graft Polymerization of Styrene: Solid Phases for Organic and Peptide Synthesis", Journal of Polymer Science: Part A: Polymer Chemistry, Dec. 2002, Vo. 40, No. 23, pp. 4180-4192.
Barner, "Reversible Addition—Fragmentation Chain Transfer Graft Copolymerization of Styrene and m-Isopropenyl-α, α-dimethylbenzyl Isocyanate from Polypropylene Lanterns: Solid Phases for Scavenging Applications", Journal of Polymer Science: Part A: Polymer Chemistry, Jan. 2006, vol. 44, No. 2, pp. 857-864.
Barner, "Surface Grafting via the Reversible Addition—Fragmentation Chain-Transfer (RAFT) Process: From Polypropylene Beads to Core—Shell Microspheres", Australian Journal of Chemistry, Sep. 2003, vol. 56, No. 10, p. 1091.

(Continued)

*Primary Examiner* — Hayden Brewster

(57) ABSTRACT

Articles with covalently attached thiocarbonylthio-containing groups are provided. More specifically, the articles include a solid polymeric substrate with a plurality of thiocarbonylthio-containing groups covalently attached directly to a carbon atom in a polymeric backbone of the solid polymeric substrate. Methods of making the articles with covalently attached thiocarbonylthio-containing are provided. Additionally, methods of using these articles to generate further articles with covalently attached polymeric chains are provided.

12 Claims, No Drawings

(56) References Cited

U.S. PATENT DOCUMENTS

| | | | |
|---|---|---|---|
| 7,250,479 | B2 | 7/2007 | Le |
| 7,338,692 | B2 | 3/2008 | Smith |
| 7,662,986 | B2 | 2/2010 | Le |
| 8,544,658 | B2 | 10/2013 | Stenzel |
| 9,260,638 | B2 | 2/2016 | Krepski |
| 2006/0270867 | A1 | 11/2006 | Shih |
| 2007/0154703 | A1 | 7/2007 | Waller |
| 2008/0268551 | A1 | 10/2008 | Bowman |
| 2010/0317817 | A1 | 12/2010 | Linhardt |
| 2012/0252091 | A1 | 10/2012 | Rasmussen |
| 2015/0203593 | A1 | 7/2015 | Shannon |
| 2016/0231208 | A1* | 8/2016 | Rasmussen ............ C07K 1/18 |

FOREIGN PATENT DOCUMENTS

| | | | | |
|---|---|---|---|---|
| WO | WO 2004-078793 | | 9/2004 | |
| WO | WO 2010-147864 | | 12/2010 | |
| WO | WO 2010-147874 | | 12/2010 | |
| WO | WO-2010147864 | A2 * | 12/2010 | ............ A61L 27/52 |
| WO | WO 2013-184366 | | 12/2013 | |
| WO | WO 2014-204763 | | 12/2014 | |
| WO | WO 2015-050767 | | 4/2015 | |
| WO | WO 2015-121225 | | 8/2015 | |
| WO | WO 2018-048696 | | 3/2018 | |
| WO | WO 2018-048698 | | 3/2018 | |
| WO | WO 2019-070889 | | 4/2019 | |
| WO | WO 2019-123176 | | 6/2019 | |

OTHER PUBLICATIONS

Barsbay, "RAFT-Mediated Polymerization and Grafting of Sodium 4-Styrenesulfonate from Cellulose Initiated via Y-Radiation", Polymer, Feb. 2009, vol. 50, No. 4, pp. 973-982.

Barsbay, "Verification of Controlled Grafting of Styrene from Cellulose via Radiation-Induced RAFT Polymerization", Macromolecules, Sep. 2007, vol. 40, pp. 7140-7147.

Chong, "Thiocarbonylthio, Compounds [SC(Ph)S-R] in Free Radical, Polymenzation with Reversible, Addition-Fragmentation Chain Transfer, (RAFT Polymerization). Role of the, Free-Radical Leaving Group (R)", Macromolecules, Apr. 2003, vol. 36, No. 7, pp. 2256-2272.

Davies, "The Separation of Airborne Dust and Particles" Proceedings of the Institution of Mechanical Engineers, Jun. 1953, vol. 167, No. 1B, pp. 185-213.

Harvison, "End Group Reactions of RAFT-Prepared (Co)Polymers", Australian Journal of Chemistry, 2011, vol. 64, No. 8, pp. 992-1006.

Kiani, "Raft Mediated Surface Grafting of t-Butyl Acrylate onto an Ethylene—Propylene Copolymer Initiated by Gamma Radiation", Journal of Polymer Science—Part A—Polymer Chemistry, Mar. 2007, vol. 45, No. 6, pp. 1074-1083.

Luo, "Surface-Initiated Photopolymerization of Poly(ethylene glycol) Methyl Ether Methacrylate on a Diethyldithiocarbamate-Mediated Polymer Substrate", Macromolecules, Apr. 2002, vol. 35, No. 7, pp. 2487-2693.

Moad, "Living Radical Polymerization by the RAFT Process," Australian Journal of Chemistry, 2005, vol. 58, No. 6, pp. 379-410.

Otsu, "Iniferter Concept and Living Radical Polymerization", Journal of Polymer Science—Part A—Polymer Chemistry, Jun. 2000, vol. 38, No. 12, pp. 2121-2136.

Wente, "Manufacture of Superfine Organic Fibers", Naval Research Laboratories Report No. 4364, May 1954, 21 pages.

Wente, "Superfine Thermoplastic Fibers", Industrial & Engineering Chemistry, Aug. 1956, vol. 48, No. 8, pp. 1342-1346.

Williamson, "Regioselective C—H Xanthylation as a Platform for Polyolefin Functionalization", Angewandte Chemie, May 2018, vol. 57, No. 21, pp. 6261-6265.

Xu, "Functionalization of Nylon Membranes via Surface-Initiated Atom-Transfer Radical Polymerization", Langmuir, October Jul. 2007, vol. 23, No. 16, pp. 8585-8592.

Yu, "Thermo- and pH-Responsive Polypropylene Microporous Membrane Prepared by the Photoinduced RAFT-Mediated Graft Copolymerization", Journal of Membrane Science, Nov. 2009, vol. 343, No. 1-2, pp. 82-89.

Zhou_ "Development of a Novel RAFT-UV Grafting Technique to Modify Polypropylene Membrane used for NOM Removal", Separation and Purification Technology, Feb. 2010, vol. 71, No. 2 pp. 233-240.

International Search Report for PCT International Application No. PCT/IB2018/060118, mailed on Apr. 25, 2019, 5 pages.

International Search Report for PCT International Application No. PCT/IB2018/060120, mailed on May 7, 2019, 5 pages.

* cited by examiner

POLYMERIC SUBSTRATES WITH ATTACHED POLYMERIC CHAINS

CROSS REFERENCE TO RELATED APPLICATIONS

This application is a national stage filing under 35 U.S.C. 371 of PCT/IB2018/060120, filed Dec. 14, 2018, which claims the benefit of U.S. Provisional Patent Application No. 62/608,184, filed Dec. 20, 2017, the disclosure of which is incorporated by reference herein in its/their entirety.

BACKGROUND

Detection, quantification, isolation, and purification of target biomaterials, such as viruses and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules are important for therapeutic uses and in biomedical research.

Polymeric materials have been widely used for the separation and purification of various target biomaterials. Such separation and purification methods can be based on various binding factors or mechanisms including the presence of an ionic group, the size of the target biomaterial, a hydrophobic interaction, an affinity interaction, the formation of a covalent bond, and so forth.

Membrane-based technologies, especially in disposable format, are becoming increasingly important in biopharmaceutical and vaccine manufacturing processes. Membranes have been used in passive, size-based separations (for example, in virus removal applications) and, more recently, in active filtration (for example, for the removal of minor contaminants in later stages of purification processes).

Functionalized membranes (i.e., membranes functionalized with various groups including polymeric material) have typically suffered from relatively low biomaterial binding capacities, however, and this has generally limited their use in large-scale purifications. Porous beaded chromatography resins (bearing ion exchange or other interactive ligand functional groups), rather than functionalized membranes, therefore have been used in "capture-and-elute" type protein purification processes.

Various methods have been used for attaching polymeric materials to a substrate such as a membrane. For example, Patent Application WO 2015/050767 (Rasmussen et al.), WO 2013/184366 (Bothof et al.), WO 2014/204763 (Rasmussen et al.) describe ligand-functionalized substrates that can be used for binding various biomaterials.

Controlled radical initiators have been used in the synthesis of various polymeric materials. Some of these controlled radical initiators can be used for reversible addition-fragmentation chain transfer (RAFT) polymerization reactions. RAFT polymerization methods can be used, for example, to more easily control the molecular weight of the resulting polymeric materials.

SUMMARY

Articles containing a solid polymeric substrate with covalently attached polymeric chains and methods of making such articles are provided. These polymeric chains have an acid group, basic group, salt thereof, or a combination thereof. The articles (which are referred to as second articles) are prepared from another article (a first article) that can be referred to as a functionalized substrate. The functionalized substrate contains a solid polymeric substrate with covalently attached thiocarbonylthio-containing groups. The thiocarbonylthio-containing groups on the functionalized substrate can serve as iniferters for polymerization reactions. Advantageously, the nature of the solid polymeric substrate included in the articles can be hydrophobic or hydrophilic and the molecular weight of the covalently attached polymeric chains formed using the functionalized substrates can be controlled.

In a first aspect, a method of making an article having a solid polymeric substrate with covalently attached polymeric chains is provided. The method includes providing a solid polymeric substrate and generating free radicals on a surface of the solid polymeric substrate to form a treated substrate. The method further includes reacting the free radicals of the treated substrate with a fluid comprising a thiocarbonylthio-containing compound to bond a plurality of thiocarbonylthio-containing groups directly and covalently to a polymeric backbone of the solid polymeric substrate and forming a functionalized substrate. The method still further includes preparing a reaction mixture by contacting the functionalized substrate with a radically polymerizable monomer composition comprising a first monomer having (a) at least one ethylenically unsaturated group, (b) at least one ligand functional group that is an acidic group, basic group, or salt thereof, and (c) a spacer group that directly links the at least one ethylenically unsaturated group and the at least one ligand functional group by a chain of at least six catenated atoms. The method yet further includes exposing the reaction mixture to actinic radiation and forming a polymeric chain directly and covalently attached to a carbon atom in a polymeric backbone of the solid polymeric substrate, the polymeric chains being a polymerized product of the radically polymerizable monomer composition.

In a second aspect, an article is provided that includes a) a solid polymeric substrate and b) polymeric chains attached (bonded) directly and covalently to carbon atoms in a polymeric backbone of the solid polymeric substrate. The polymeric chains comprise a polymerized product of a radically polymerizable monomer composition comprising a first monomer having (a) at least one ethylenically unsaturated group, (b) at least one ligand functional group that is an acidic group, basic group, or salt thereof, and (c) a spacer group that directly links the at least one ethylenically unsaturated group and the at least one ligand functional group by a chain of at least six catenated atoms. At least some of the polymeric chains are terminated by a thiol or a thiocarbonylthio-containing group.

DETAILED DESCRIPTION

Articles containing a solid polymeric substrate with covalently attached polymeric chains and methods of making such articles are provided. The polymeric chains have pendant acid groups, basic groups, salts thereof, or a combination thereof. The articles are prepared from an intermediate article that can be referred to as a functionalized substrate. The functionalized substrate contains a solid polymeric substrate with covalently attached thiocarbonylthio-containing groups. The thiocarbonylthio-containing groups on the functionalized substrate can serve as iniferters during the formation of the polymeric chains. The articles can be used for binding biomaterials.

As used herein, the terms "a", "an", "the", and "at least one" are used interchangeably.

The term "and/or" means either or both. For example, "A and/or B" means only A, only B, or both A and B.

The term "aggregated protein" refers to an association of at least two molecules of a product of interest such as a therapeutic protein (e.g., antibody). The association of the at least two molecules may arise by means including, but not limited to, covalent, non-covalent, disulfide, or non-reducible crosslinking.

The term "alkyl" refers to a monovalent group that is a radical of an alkane. The alkyl group can have 1 to 32 carbon atoms, 1 to 20 carbon atoms, 1 to 12 carbon atoms, 1 to 10 carbon atoms, 1 to 6 carbon atoms, or 1 to 4 carbon atoms. The alkyl can be linear, branched, cyclic, or a combination thereof. A linear alkyl has at least one carbon atom while a cyclic or branched alkyl has at least 3 carbon atoms. In some embodiments, if there are greater than 12 carbon atoms, the alkyl is branched.

The term "alkylene" refers to a divalent group that is a radical of an alkane. The alkylene group can have 1 to 32 carbon atoms, 1 to 20 carbon atoms, 1 to 12 carbon atoms, 1 to 10 carbon atoms, 1 to 6 carbon atoms, or 1 to 4 carbon atoms. The alkyl can be linear, branched, cyclic, or a combination thereof. A linear alkylene has at least one carbon atom while a cyclic or branched alkyl has at least 3 carbon atoms. In some embodiments, if there are greater than 12 carbon atoms, the alkylene is branched.

The term "alkoxy" refers to a monovalent group of formula —$OR^a$ where $R^a$ is an alkyl as defined above.

The term "alkenyl" refers to a monovalent group that is a radical of an alkene, which is a hydrocarbon compound having at least one carbon-carbon double bond. In some embodiments, the alkenyl has a single carbon-carbon double bond. In some more specific embodiments, the alkenyl has an ethylenically unsaturated group (the carbon-carbon double bond is between the last two carbon atoms in a chain). The alkenyl can be linear, branched, or cyclic. The alkenyl often has at least 2, at least 3, at least 4, or at least 5 carbon atoms and can have up to 32 carbon atoms, up to 24 carbon atoms, up to 20 carbon atoms, up to 12 carbon atoms, up to 10 carbon atoms, or up to 5 carbon atoms.

The term "alkenyloxy" refers to a monovalent group of formula —$OR^b$ where $R^b$ is an alkenyl as defined above.

The term "aryl" refers to a monovalent group that is a radical of an aromatic carbocyclic compound. The aryl group has at least one aromatic carbocyclic ring and can have 1 to 3 optional rings that are connected to or fused to the aromatic carbocyclic ring. The additional rings can be aromatic, aliphatic, or a combination thereof. The aryl group usually has 5 to 20 carbon atoms or 6 to 10 carbon atoms.

The term "arylene" refers to a divalent group that is a radical of an aromatic carbocyclic compound. The arylene group has at least one aromatic carbocyclic ring and can have 1 to 3 optional rings that are connected to or fused to the aromatic carbocyclic ring. The additional rings can be aromatic, aliphatic, or a combination thereof. The arylene group usually has 5 to 20 carbon atoms or 6 to 10 carbon atoms.

The term "aralkyl" refers to an alkyl group substituted with at least one aryl group. That is, the aralkyl group is of formula —$R^d$—Ar where $R^d$ is an alkylene and Ar is an aryl. The aralkyl group contains 6 to 40 carbon atoms. The aralkyl group often contains an alkylene group having 1 to 20 carbon atoms or 1 to 10 carbon atoms and an aryl group having 5 to 20 carbon atoms or 6 to 10 carbon atoms.

The term "aralkylene" refers to an alkylene group substituted with at least one aryl group.

The term "aralkyloxy" refers to a monovalent group that is of formula —O—$R^d$—Ar with $R^d$ and Ar being the same as defined above for aralkyl.

The term "alkaryl" refers to an aryl group substituted with at least one alkyl group. That is, the alkaryl group is of formula —$Ar^1$—$R^e$ where $Ar^1$ is an arylene and $R^e$ is an alkyl. The alkaryl group contains 6 to 40 carbon atoms. The alkaryl group often contain an arylene group having 5 to 20 carbon atoms or 6 to 10 carbon atoms and an alkyl group having 1 to 20 carbon atoms or 1 to 10 carbon atoms.

The term "aryloxy" refers to a monovalent group of formula —O—Ar where Ar is an aryl.

The term "boronato" refers to a group of formula —$B(OH)_2$.

The term "carboxy" refers to a group of formula —C(=O)—OH.

The term "iniferter" is used to refer to a group that can, under appropriate conditions, function as a free radical initiator, as a chain transfer agent, or as a free radical chain terminator.

The term "hydrocarbyl" refers to a monovalent radical of a hydrocarbon. The hydrocarbyl can be saturated, partially unsaturated, or unsaturated and can have up to 20 carbon atoms, up to 10 carbon atoms, up to 6 carbon atoms, or up to 4 carbon atoms. It often has at least 1 carbon atom or at least 2 carbon atoms. The hydrocarbyl is often an alkyl, aryl, aralkyl, or alkaryl.

The term "hydrocarbylene" refers to a divalent radical of a hydrocarbon. The hydrocarbylene can be saturated, partially unsaturated, or unsaturated and can have up to 40 carbon atoms, up to 20 carbon atoms, up to 10 carbon atoms, up to 6 carbon atoms, or up to 4 carbon atoms. It often has at least 1 carbon atom or at least 2 carbon atoms. The hydrocarbyl is often an alkylene, arylene, aralkylene, or alkarylene.

The term "catenated atom" means an in-chain atom (rather than an atom of a chain substituent).

The term "catenated heteroatom" means a heteroatom replaces one or more carbon atoms in a carbon chain. The heteroatom is typically oxygen, sulfur, or nitrogen.

The term "fluid" refers to a liquid and/or gas.

The term "functionalized substrate" refers to a polymeric substrate having a plurality of covalently attached thiocarbonylthio-containing groups.

The term "heteroatom" means an atom other than carbon or hydrogen. The heteroatom is typically sulfur, nitrogen, or oxygen.

The term "heterohydrocarbyl" refers to a hydrocarbyl with at least one but not all of the catenated carbon atoms replaced with a heteroatom selected from oxygen (—O—), sulfur (—S—), and nitrogen (e.g., —NH—).

The term "(hetero)hydrocarbyl" refers to a hydrocarbyl, heterohydrocarbyl, or both.

The term "heterohydrocarbylene" refers to a hydrocarbylene with at least one but not all of the catenated carbon atoms replaced with a heteroatom selected from oxygen (—O—), sulfur (—S—), and nitrogen (e.g., —NH—).

The term "(hetero)hydrocarbylene" refers to a hydrocarbylene, heterohydrocarbylene, or both.

The term "heteroaralkylene" refers to an aralkylene having a heteroatom in the aryl group. Stated differently, it is an alkylene bonded to a heteroaryl where a heteroaryl is an aryl having one of the ring carbon atoms replaced with a heteroatom selected from oxygen (—O—), sulfur (—S—), and nitrogen (e.g., —NH—).

The term "hydrogen bond acceptor" refers to a heteroatom selected from oxygen, nitrogen, and sulfur that has a lone electron pair. The hydrogen bond acceptor is often carbonyl, carbonyloxy, or ether oxygen.

The term "hydrogen bond donor" refers to a moiety consisting of a hydrogen atom covalently bonded to a heteroatom selected from oxygen, nitrogen, and sulfur. The hydrogen bond donor is often imino, thio, or hydroxy.

The term "hydrogen bonding moiety" means a moiety that includes at least one hydrogen bond donor and at least one hydrogen bond acceptor.

The term "iminocarbonylimino" means a divalent group or moiety of formula —N(R)—C(=O)—N(R)—, wherein each R is independently hydrogen, alkyl (for example, selected from alkyl groups having from one to four carbon atoms), or aryl. Often one or both R groups are hydrogen.

The term "iminothiocarbonylimino" means a divalent group or moiety of formula —N(R)—C(=S)—N(R)—, wherein each R is independently hydrogen, alkyl (for example, selected from alkyl groups having from one to four carbon atoms), or aryl. Often one or both R groups are hydrogen.

The term "isocyanato" means a group of formula —N=C=O.

The term "oxycarbonylimino" means a divalent group or moiety of formula —O—C(=O)—N(R)—, wherein R is hydrogen, alkyl (for example, selected from alkyl groups having from one to four carbon atoms), or aryl. Often the R group is hydrogen.

The term "oxythiocarbonylimino" means a divalent group or moiety of formula —O—C(=S)—N(R)—, wherein R is hydrogen, alkyl (for example, selected from alkyl groups having from one to four carbon atoms), or aryl. Often the R group is hydrogen.

The term "ethylenically unsaturated" means a group of formula —CY=CH$_2$ where Y is hydrogen or hydrocarbyl (e.g., alkyl or aryl).

The term "phosphono" refers to a group of formula —PO$_3$H$_2$ wherein this group is not attached to an oxygen atom (it is usually attached to a carbon atom).

The term "phosphato" refers to a group of formula —OPO$_3$H$_2$.

The terms "polymer" and "polymeric material" are used interchangeably and refer to materials formed by reacting one or more monomers. The terms include homopolymers, copolymers, terpolymers, or the like. Likewise, the terms "polymerize" and "polymerizing" refer to the process of making a polymeric material that can be a homopolymer, copolymer, terpolymer, or the like.

The term "sulfono" refers to a group of formula —SO$_3$H wherein this group is not attached to an oxygen atom (it is usually attached to a carbon atom).

The term "sulfato" refers to a group of formula —OSO$_3$H.

The term "thiocarbonylimino" means a divalent group or moiety of formula —C(=S)NR—, where R is hydrogen, alkyl (for example, selected from alkyl groups having from one to four carbon atoms), or aryl. Group R is often hydrogen.

The term "thiocarbonylthio" refers to a divalent group —S—C(=S)—.

The term "treated substrate" refers to a polymeric substrate having a plurality of free radicals available for reaction with another compound such as a thiocarbonylthio-containing compound.

The terms "in a range of" or "in the range of" are used interchangeably to refer to all values within the range plus the endpoints of the range.

Articles containing a solid polymeric substrate with covalently attached polymeric chains and methods of making such articles are provided. These articles are often referred to herein as "second articles". More particularly, the second article is prepared from a first article that has a plurality of thiocarbonylthio-containing groups attached (bonded) covalently and directly to a backbone polymer material of the solid polymeric substrate. When the first article, which is referred to herein interchangeably as a "functionalized substrate", is contacted with a radically polymerizable monomer composition and exposed to actinic radiation such as ultraviolet radiation, polymeric chains are formed that are covalently and directly attached (bonded) to carbon atoms in a polymeric backbone of the solid polymeric substrate. The polymeric chains are a polymerized product of the radically polymerizable monomer composition. The radically polymerizable monomer composition contains at least one first monomer having (a) at least one ethylenically unsaturated group, (b) at least one ligand functional group that is an acidic group, basic group, or salt thereof, and (c) a spacer group that directly links the at least one ethylenically unsaturated group and the at least one ligand functional group by a chain of at least six catenated atoms.

The articles (including the treated substrates, functionalized substrates (first articles), and second articles) have a solid polymeric substrate. That is, the polymeric substrate is not a liquid and is not dissolved in a solution. The terms "solid polymeric substrate", "polymeric substrate", and "substrate" are used interchangeably herein. The polymeric substrate can be flexible or rigid, porous or non-porous, and can be thermoplastic or thermoset materials. The polymeric substrate can have any desired size, shape, and form. In many examples, the polymeric substrate is in the form of particles, fibers, films, non-woven webs, woven webs, membranes, sponges, or sheets. In some examples, the polymeric substrate is a porous substrate such as a porous membrane or non-woven web.

To prepare large articles or many articles and for ease of manufacturing, the polymeric substrate can be in the form of a roll such as a roll of film, non-woven web, woven web, membrane, sponge, or sheet. This allows the use of roll-to-roll processing to prepare the articles.

Any polymeric material can be used to form the substrates. In some embodiments, the polymeric material is a thermoplastic. Suitable thermoplastics include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates) and copolymers thereof such as poly(ethylene)-co-poly(vinyl acetate), polyesters such as poly(lactic acid), poly(vinyl alcohol) and copolymers thereof such as poly(ethylene)-co-poly(vinyl alcohol), poly(vinyl esters), poly(vinyl ethers), poly(carbonates), polyurethanes, poly((meth)acrylates) and copolymers thereof, and combinations thereof.

Suitable polyolefins for the substrate include poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene), poly(ethylene-co-1-butene-co-1-hexene), poly(butadiene) and copolymers thereof, and combinations thereof.

Suitable fluorinated polymers for the substrate include poly(vinyl fluoride), poly(vinylidene fluoride), copolymers of vinylidene fluoride (such as poly(vinylidene fluoride-cohexafluoropropylene)), copolymers of chlorotrifluoroethylene (such as poly(ethylene-co-chlorotrifluoroethylene)), and combinations thereof.

Suitable polyamides for the substrate include various nylon compositions such as, for example, poly(iminoadipolyliminohexamethylene), poly(iminoadipolyliminodecamethylene), polycaprolactam, and combinations thereof. Suitable polyimides include poly(pyromellitimide), and combinations thereof.

Suitable poly(ether sulfones) for the substrate include poly(diphenylether sulfone), poly(diphenylsulfone-co-diphenylene oxide sulfone), and combinations thereof.

Suitable copolymers of vinyl acetate for the substrate include copolymers of ethylene and vinyl acetate as well as terpolymers of vinyl acetate, vinyl alcohol, and ethylene.

Thiocarbonylthio-containing groups are grafted to the surface of the polymeric substrate to form a functionalized substrate, which is the first article. The polymeric substrate itself is typically free of thiocarbonylthio-containing groups. That is, the polymeric substrate does not include a polymeric material having thiocarbonylthio-containing groups (e.g., a (meth)acrylate polymer having pendant thiocarbonylthio-containing groups) and/or does not include a coating layer that contains a polymeric material having thiocarbonylthio-containing groups. Alternatively, additional thiocarbonyl-containing groups can be grafted to a polymeric substrate or to a coating layer that contains thiocarbonylthio-containing groups. Grafting can substantially increase the density of the thiocarbonylthio-containing groups on the surface of the polymeric substrate.

If the polymeric substrate is porous, the pores can have any desired average size. In some embodiments, the pores are macroporous, mesoporous, microporous, or a mixture thereof. As used herein, the term "macroporous" refers to a material having pores with diameters greater than 50 nanometers, the term "mesoporous" refers a material having pores with diameters in a range of 2 nanometers to 50 nanometers, and "microporous" refers to a material having pores with diameters less than 2 nanometers.

In some applications, the polymeric substrate is a porous membrane. For example, if the second articles will be used for separating biomaterials, the polymeric substrate can be a porous membrane having an average pore size (average longest diameter of the pore) that is often greater than 0.1 micrometer to minimize size exclusion separations, minimize diffusion constraints, and maximize surface area and separation. Generally, the average pore size can be in the range of 0.1 to 10 micrometers. For example, the average pore size is at least 0.2 micrometers, at least 0.4 micrometers, at least 0.6 micrometers, at least 0.8 micrometers and up to 8 micrometers, up to 6 micrometers, up to 4 micrometers, or up to 2 micrometers.

In some applications, a preferred porous polymeric substrate is a macroporous membrane such as a thermally induced phase separation (TIPS) membrane. TIPS membranes are often prepared by forming a solution of a thermoplastic material and a second material above the melting point of the thermoplastic material. Upon cooling, the thermoplastic material crystallizes and phase separates from the second material. The crystallized material is often stretched. The second material is optionally removed either before or after stretching. Macroporous membranes are further described in U.S. Pat. No. 4,539,256 (Shipman), U.S. Pat. No. 4,726,989 (Mrozinski), U.S. Pat. No. 4,867,881 (Kinzer), U.S. Pat. No. 5,120,594 (Mrozinski), U.S. Pat. No. 5,260,360 (Mrozinski), and U.S. Pat. No. 5,962,544 (Waller, Jr.). Some exemplary TIPS membranes include poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and (meth) acrylate-containing polymers or copolymers. TIPS membranes including PVDF are further described in U.S. Pat. No. 7,338,692 (Smith et al.).

In some embodiments, the porous substrate can include a nylon macroporous film or sheet (for example, a macroporous membrane), such as those described in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinaccio et al.), U.S. Pat. No. 3,928,517 (Knight et al.),U.S. Pat. No. 4,707,265 (Barnes, Jr. et al.), and U.S. Pat. No. 5,458,782 (Hou et al.).

In other embodiments, the porous substrate can be a nonwoven web, which can include nonwoven webs manufactured by any of the commonly known processes for producing nonwoven webs. As used herein, the term "nonwoven web" refers to a fabric that has a structure of individual fibers or filaments that are randomly and/or unidirectionally interlaid in a mat-like fashion.

For example, the fibrous nonwoven web can be made by wet laid, carded, air laid, spunlaced, spunbonding, or meltblowing techniques, or combinations thereof. Spunbonded fibers are typically small diameter fibers that are formed by extruding molten thermoplastic polymer as filaments from a plurality of fine, usually circular capillaries of a spinneret, with the diameter of the extruded fibers being rapidly reduced. Meltblown fibers are typically formed by extruding molten thermoplastic material through a plurality of fine, usually circular, die capillaries as molten threads or filaments into a high velocity, usually heated gas (for example, air) stream, which attenuates the filaments of molten thermoplastic material to reduce their diameter. Thereafter, the meltblown fibers are carried by the high velocity gas stream and are deposited on a collecting surface to form a web of randomly-dispersed, meltblown fibers. Any of the nonwoven webs can be made from a single type of fiber or from two or more fibers that differ in the type of thermoplastic polymer and/or thickness.

Further details of manufacturing methods of useful nonwoven substrates have been described by Wente in "Superfine Thermoplastic Fibers," Indus. Eng. Chem., 48, 1342 (1956) and by Wente et al. in "Manufacture of Superfine Organic Fibers," Naval Research Laboratories Report No. 4364 (1954).

The nonwoven web substrate may optionally further comprise one or more layers of scrim. For example, either or both major surfaces of the nonwoven web may each optionally further comprise a scrim layer. The scrim, which is typically a woven or nonwoven reinforcement layer made from fibers, is included to provide strength to the nonwoven web. Suitable scrim materials include, but are not limited to, nylon, polyester, fiberglass, polyethylene, polypropylene, and the like. The average thickness of the scrim can vary but often ranges from about 25 to about 100 micrometers, preferably about 25 to about 50 micrometers. The scrim layer may optionally be bonded to the nonwoven article. A variety of adhesive materials can be used to bond the scrim to the nonwoven. Alternatively, the scrim may be heat-bonded to the nonwoven web.

The porosity of nonwoven substrates is typically characterized by properties such as fiber diameter, or basis weight, or solidity, rather than by pore size. The fibers of the nonwoven substrate are typically microfibers having an effective fiber diameter of from at least 0.5, 1, 2, or even 4 micrometers and at most 15, 10, 8, or even 6 micrometers, as calculated according to the method set forth in Davies, C. N., "The Separation of Airborne Dust and Particles," Institution of Mechanical Engineers, London, Proceedings 1B, 1952, The nonwoven substrate preferably has a basis weight in the range of at least 5, 10, 20, or even 50 g/m$^2$; and at most 800, 600, 400, 200, or even 100 g/m$^2$. The minimum tensile strength of the nonwoven web is about 4.0 Newtons. It is generally recognized that the tensile strength of nonwoven substrates is lower in the machine direction than in the cross-web direction due to better fiber bonding and entanglement in the latter.

Nonwoven web loft is measured by solidity, a parameter that defines the solids fraction in a volume of web. Lower solidity values are indicative of greater web loft. Solidity ($\alpha$) is a unitless fraction typically represented by: $\alpha = m_f \div \rho_f \times L_{nonwoven}$ where $m_f$ is the fiber mass per sample surface area, $\rho_r$ is the fiber density, and $L_{nonwoven}$ is the nonwoven thickness. Solidity is used herein to refer to the nonwoven substrate itself and not to the functionalized nonwoven substrate. When a nonwoven substrate contains mixtures of two or more kinds of fibers, the individual solidities are determined for each kind of fiber using the same $L_{nonwoven}$ and these individual solidifies are added together to obtain the web's solidity, $\alpha$.

The first articles include a functionalized substrate having a plurality of thiocarbonylthio-containing groups directly and covalently attached (bonded) to the surface of the polymeric substrate. The thiocarbonylthio-containing groups are typically covalently attached to a carbon atom in a polymeric backbone of the solid polymeric substrate. The thiocarbonylthio-containing groups are covalently attached by reacting with a free radical on a surface of the solid polymeric substrate. Various methods can be used to generate the free radicals on this surface. Polymeric substrates having free radicals available for further reaction are referred to as treated substrates.

In a first method of forming a treated substrate, an imbibing solution is prepared. The imbibing solution contains a Type II photoinitiator dissolved in a solvent. The solvent is an organic solvent and/or water. The imbibing solution is applied to a surface of the polymeric substrate as a coating layer. The coating layer is then exposed to actinic radiation, which is typically in the ultraviolet region of the electromagnetic spectrum. Upon exposure to the actinic radiation, the Type II photoinitiator abstracts a hydrogen from the polymeric substrate resulting in the generation of free radicals on its surface and the formation of the treated substrate.

Type II photoinitiators included in the imbibing solution are typically aromatic ketone compounds. Examples include, but are not limited to, benzophenone, carboxybenzophenone, 4-(3-sulfopropyloxy)benzophenone sodium salt, Michler's ketone, benzil, anthraquinone, 5,12-naphthacenequinone, aceanthracenequinone, benz(A)anthracene-7,12-dione, 1,4-chrysenequinone, 6,13-pentacenequinone, 5,7,12, 14-pentacenetetrone, 9-fluorenone, anthrone, xanthone, thioxanthone, 2-(3-sulfopropyloxy)thioxanthen-9-one, acridone, dibenzosuberone, acetophenone, and chromone.

The imbibing solution can contain any suitable amount of the Type II photoinitiator. The concentration is often in a range of 0.1 to 20 weight percent based on a total weight of the Type II photoinitiator and the solvent. For example, the concentration can be at least 0.2 weight percent, at least 0.5 weight percent, at least 1 weight percent, at least 2 weight percent, or at least 5 weight percent and, depending on its solubility in the solvent, can be up to 20 weight percent, up to 16 weight percent, up to 12 weight percent, up to 10 weight percent, up to 8 weight percent, up to 6 weight percent, or up to 5 weight percent.

Suitable solvents for use in the imbibing solution are typically organic solvents but can be water (when the Type II photoinitiator is water soluble) or a mixture of water and an organic solvent. Suitable non-protic polar organic solvents include esters (e.g., ethyl acetate, propyl acetate), alkoxyalkyl acetates (e.g., methoxyethyl acetate, ethoxyethyl acetate, propoxyethyl acetate, and butoxyethyl acetate), trialkyl phosphates such as triethylphosphate, ketones (e.g., acetone, methyl ethyl ketone, methyl propyl ketone, and methyl isobutyl ketone), sulfoxides (e.g., dimethyl sulfoxide). Suitable protic polar organic solvents include alcohols (e.g., methanol, ethanol, propanol, isopropanol, n-butanol, and tert-butyl alcohol), glycols (e.g., ethylene glycol and propylene glycol), glycol ethers (e.g., methoxyethanol, ethoxyethanol, propoxyethanol, butoxyethanol, methyl carbitol and ethyl carbitol), and mixtures thereof. The polar organic solvent can be mixed with water, if desired. Suitable nonpolar organic solvents include alkanes (e.g., pentane, hexane, heptane, isooctane, and decane), aromatic solvents (e.g., benzene, toluene, and xylene), and ethers (e.g., diethyl ether, tetrahydrofuran, dioxane). Although they may be useful in some instances, most alcohols and ethers are not preferred as solvents due to their propensity for undergoing interfering hydrogen abstraction reactions.

Any method of application of the imbibing solution can be used. In many processes, the imbibing solution is applied as a coating layer to the polymeric substrate. If the polymeric substrate is porous, pressure can be applied to remove air bubbles and excess imbibing solution before exposing the treated substrate to actinic radiation. For example, a cover film that is transparent to the actinic radiation can be applied such that the imbibing coating layer is positioned between the polymeric substrate and the cover film. Pressure can be applied to the surface of the cover film opposite the imbibing coating.

The source of actinic radiation is often an ultraviolet (UV) light source. UV light can be provided by various light sources such as light emitting diodes (LEDs), black lights, medium pressure mercury lamps, etc. or a combination thereof. The actinic radiation can also be provided with higher intensity light sources such as those available from Fusion UV Systems Inc. The ultraviolet light sources can be relatively low light intensity sources such as blacklights that provide generally 10 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc., in Sterling, VA) over a wavelength range of 280 to 400 nanometers. Alternatively, relatively high light intensity sources such as medium pressure mercury lamps can be used that provide intensities generally greater than 10 mW/cm$^2$, preferably between 15 and 450 mW/cm$^2$. The exposure time can be up to about 30 minutes or even longer.

In some embodiments, it is preferable to use lights that emit a narrow spectrum of light in the ultraviolet region of the electromagnetic spectrum. These light sources, which include LEDs and lasers, can enhance the rate of free radical generation, or can enhance the rate of polymerization while maintaining the reactive nature of the polymeric material in subsequent monomer grafting steps.

The thiocarbonylthio-containing compound can be present when free radicals are generated on the surface of the solid polymeric substrates or can be introduced after generation of the free radicals. If the thiocarbonylthio-containing compound is present during free radical generation, it is typically dissolved in the imbibing solution along with the Type II photoinitiator. If the thiocarbonylthio-containing compound is not present during free radical generation, the intermediate radical derived from the Type II photoinitiator via hydrogen abstraction typically couples with the radical on the surface of the substrate to form a hemi-pinacol type compound. The thiocarbonylthio-containing compound can be applied as a second coating layer to the solid polymeric substrate comprising hemi-pinacol groups. The coated substrate is again exposed to actinic radiation to regenerate the substrate radical and transfer the thiocarbonylthio-containing group to the surface of the substrate. The product is the functionalized substrate (i.e., first article).

In other processes for generating free radicals on a surface of the polymeric substrate, the substrate itself is photoactive. An imbibing solution is prepared containing the thiocarbonylthio-containing compound dissolved in a solvent. The imbibing solution is applied to a surface of the polymeric substrate as a coating layer. The coating layer is then exposed to actinic radiation, which is typically in the ultraviolet region of the electromagnetic spectrum. Upon exposure to the actinic radiation, the polymeric substrate absorbs enough energy that some of its covalent bonds are broken, resulting in the generation of free radicals on its surface and the formation of a treated substrate. The thiocarbonylthio-containing group is subsequently transferred to the substrate. Examples of photoactive polymeric substrates include polysulfones and poly(ether sulfones). Other photoactive polymeric substrates often contain an aromatic group such as, for example, homopolymers and block copolymers of poly(methylphenylsilane) and various polyimides based on benzophenone tetracarboxylic dianhydride.

In other processes for generating free radicals on a surface of the polymeric substrate, ionizing radiation is used rather than a Type II photoinitiator. As used herein, the term "ionizing radiation" refers to radiation that is of a sufficient dose and energy to form free radical reaction sites on the surface and/or in the bulk of the polymeric substrate. The radiation is of sufficient energy if it is absorbed by the polymeric substrate and results in the cleavage of chemical bonds in the substrate and the formation of free radicals. The ionizing radiation is often beta radiation, gamma radiation, electron beam radiation, x-ray radiation, plasma radiation, or other suitable types of electromagnetic radiation. Preferably, ionizing radiation is conducted in an inert environment to prevent oxygen from reacting with the radicals.

In many embodiments of this process, the ionizing radiation is electron beam radiation, gamma ray radiation, x-ray radiation, or plasma radiation because of the ready availability of suitable generators. Electron beam generators are commercially available such as, for example, the ESI ELECTROCURE EB SYSTEM from Energy Sciences, Inc. (Wilmington, MA, USA) and the BROADBEAM EB PROCESSOR from E-beam Technologies (Davenport, IA, USA). Gamma ray radiation generators are commercially available from MDS Nordion that use a cobalt-60 high energy source.

For any given type of ionizing radiation, the dose delivered can be measured in accordance with ISO/ASTM52628-13, "Standard Practice for Dosimetry in Radiation Processing," by ASTM International (West Conshohocken, PA). By altering the extractor grid voltage, beam diameter, exposure time, and distance from the irradiation source, various dose rates can be obtained.

When ionizing radiation is used, the free radicals are typically formed on a surface of the polymeric substrate prior to contact with the thiocarbonylthio-containing compound. That is, there is a first step of generating the free radicals on the surface of the solid polymeric substrate to form a treated substrate and a second step of applying a coating layer of the thiocarbonylthio-containing compound to the treated substrate. The thiocarbonylthio-containing compound and the polymeric substrate having free radicals (i.e., treated substrate) react to covalently attach thiocarbonylthio-containing groups to the polymeric substrate forming a functionalized substrate.

The thiocarbonylthio-containing group is typically attached to (grafted to or bonded to) the polymeric substrate in the functionalized substrate (i.e., first article). In most cases, the thiocarbonylthio-containing group is directly attached to a carbon atom in a polymeric backbone of the polymeric substrate. There is typically no intervening linking group such as an ester linkage, amide linkage, urethane linkage, ether linkage, siloxane linkage, or the like between the polymeric substrate and the thiocarbonyl-containing group. The thiocarbonyl-containing groups are often not those that are known to be effective as agents for reversible addition-fragmentation chain transfer (RAFT) polymerization reactions.

In many embodiments, the thiocarbonylthio-containing group is of formula —S—C(=S)—R$^1$. Group R$^1$ in the thiocarbonylthio-containing group is typically selected to be an alkoxy, aralkyloxy, alkenyloxy or —N(R$^4$)$_2$. Each R$^4$ is an alkyl or two adjacent R$^4$ groups are combined with the nitrogen to which they are both attached to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic.

Suitable alkoxy groups for R$^1$ typically have at least 1 carbon atom, at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkoxy groups have 1 to 20 carbon atoms, 1 to 10 carbon atoms, 2 to 10 carbon atoms, 1 to 6 carbon atoms, 2 to 6 carbon atoms, or 1 to 4 carbon atoms.

Suitable alkenyloxy groups for R$^1$ typically have at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkenyloxy groups have 2 to 20 carbon atoms, 2 to 10 carbon atoms, 2 to 6 carbon atoms, or 2 to 4 carbon atoms.

Suitable aralkyloxy groups for R$^1$ typically contains an alkylene group having 1 to 10 carbon atoms, 1 to 6 carbon atoms, or 1 to 4 carbon atoms and an aryl group having 5 to 12 carbon atoms, 6 to 12 carbon atoms, or 6 to 10 carbon atoms. The aryl group in the aralkyloxy group is often phenyl.

In some embodiments of the thiocarbonylthio-containing group, R$^1$ is of formula —N(R$^4$)$_2$ where each R$^4$ is an alkyl or where the two adjacent R$^4$ groups are combined with the nitrogen to which they are both attached to form a first heterocyclic ring having 1 to 3 heteroatoms selected from nitrogen, oxygen, and sulfur and 2 to 5 carbon atoms, the first heterocyclic ring being saturated or unsaturated (e.g., partially or fully unsaturated) and optionally fused to one or more second rings that are carbocyclic or heterocyclic.

Suitable alkyl $R^4$ groups typically have at least 1 carbon atom, at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkyl groups have 1 to 20 carbon atoms, 1 to 10 carbon atoms, 2 to 10 carbon atoms, 1 to 6 carbon atoms, 2 to 6 carbon atoms, or 1 to 4 carbon atoms.

When the formula —$N(R^4)_2$ forms a first heterocyclic ring, the heterocyclic ring typically has a first ring structure with 5 to 7 ring members or 5 to 6 ring members and with 1 to 3 heteroatoms or 1 to 2 heteroatoms in the ring. Ring members that are not a heteroatom are carbon. If there is one heteroatom in the first ring structure, the heteroatom is nitrogen. If there are two or three heteroatoms in the first ring structure, one heteroatom is nitrogen and any additional heteroatom is selected from nitrogen, oxygen, and sulfur. The first ring optionally can be fused to one or more second ring structures that are heterocyclic or carbocyclic and saturated or unsaturated (e.g., partially or fully unsaturated). If the second ring structure is heterocyclic, it typically has 5 to 7 or 5 to 6 ring members and 1, 2, or 3 heteroatoms selected from nitrogen, oxygen, and sulfur. If the second ring structure is carbocyclic, it is often benzene or a saturated ring having 5 or 6 ring members. In many embodiments, the heterocyclic ring has a single ring structure with 5 or 6 ring members and with either 1 or 2 heteroatoms in the ring. Examples of heterocyclic rings include, but are not limited to, morpholino, thiomorpholino, pyrrolidinyl, piperidinyl, homo-piperidinyl, indolyl, carbazolyl, imidazolyl, and pyrazolyl.

The thiocarbonylthio-containing compound can be represented by the general formula Q- S—C(=S)—$R^1$ where Q is the remainder of the compound. Group Q can include a second group (or even a third group) of formula —S—C(=S)—$R^1$ if the thiocarbonylthio-containing compound contains more than one such group. Group $R^1$ is the same as defined above. The thiocarbonylthio-containing compound reacts with a solid polymeric substrate (SS) as shown in Reaction Scheme A.

attached to the solid substrate for simplicity sake, there are a plurality of such attached groups on the functionalized substrate.

Group Q in the thiocarbonylthio-containing compound becomes a free radical during the transfer process shown in Reaction Scheme A. This group can be selected so that the S-Q bond is sufficiently weak to allow homolytic cleavage without any side reactions. In contrast to typical RAFT polymerization reactions, the expelled radical (Q*) does not need to be selected so that it can initiate free radical polymerization reactions because there are no monomers present at the time the thiocarbonylthio-containing group is covalently attached to the solid substrate. This allows the use of thiocarbonylthio-containing compounds that would ordinarily not be used in typical RAFT controlled radical polymerization reactions.

Thus, the expelled radical (Q*) may be a primary radical, as opposed to the secondary or tertiary radicals used in typical RAFT polymerizations. The expelled radical may cause reversal of the transfer reaction (i.e., if the reactions shown in the second step of Reaction Scheme A are reversible, the covalently attached group —S—C(=S)—$R^1$ can combine with the expelled radical (Q*) to reform Q- S—C(=S)—$R^1$, resulting in the reformation of a radical on the surface of the substrate). Alternatively, the expelled radical (Q*) may become deactivated in a variety of radical termination processes well known in the art, such as by coupling to form Q-Q.

Some example thiocarbonylthio-containing compounds are the symmetrical compounds of Formula (I).

$$R^1—C(=S)—S—S—C(=S)—R^1 \quad (I)$$

Group $R^1$ is the same as defined above. Examples of thiocarbonylthio-containing compounds of Formula (I) include, but are not limited to, dixanthogen (where $R^1$ is an ethoxy) and tetraethylthiuram disulfide (where is $R^1$ is of formula —$N(R^4)_2$ where each $R^4$ is ethyl).

Other example thiocarbonylthio-containing compounds are of Formula (II).

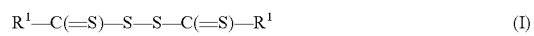

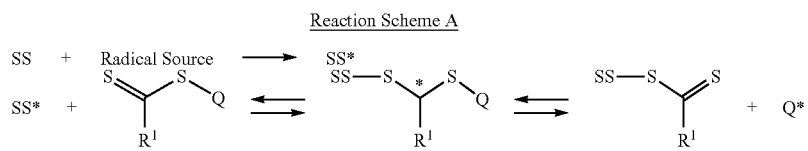

In Reaction Scheme A, free radical sites are first generated on the solid substrate. SS* represents the solid polymeric substrate having free radicals (i.e., treated substrate). When the thiocarbonylthio-containing compound is contacted with the solid substrate having free radicals, the group —S—C(=S)—$R^1$ is transferred to the solid substrate via an intermediate sulfur-stabilized radical that subsequently expels the radical Q*. This results in a radical transfer from the surface of the substrate to group Q of the thiocarbonylthio-containing compound. The reactions in the second equation of Reaction Scheme A are indicated as being reversible; however, the reactions are not necessarily reversible provided that the forward reactions can occur. The functional substrate is SS—S—C(=S)—$R^1$. Although Reaction Scheme A shows only one —S—C(=S)—$R^1$ group

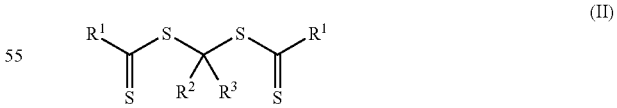

In Formula (II), each $R^1$ is an alkoxy, aralkyloxy, alkenyloxy, or —$N(R^4)_2$. Suitable alkoxy, aralkyloxy, alkenyloxy, and —$N(R^4)_2$ groups for $R^1$ are the same as described above for the thiocarbonylthio-containing group. Group $R^2$ is of formula —$(OR^5)_q$—$OR^6$ or of formula —C(=O)—X—$R^7$. Group $R^3$ is hydrogen, alkyl, aryl, substituted aryl (i.e., an aryl substituted with at least one alkyl, alkoxy, or halo), alkaryl, a group of formula —C(=O)—$OR^8$, or a group of formula —C(=O)—$N(R^9)_2$. Group $R^5$ is an alkylene, group $R^6$ is an alkyl, and q is an integer equal to at least 0. Group $R^7$ is hydrogen, alkyl, aryl, aralkyl, or substituted aryl (i.e., an aryl substituted with at least one alkyl, alkoxy, or halo). Groups $R^8$ and $R^9$ are each independently an alkyl, aryl, aralkyl, or alkaryl. Group X is a single bond, oxy, or —$NR^{10}$—. Group $R^{10}$ is hydrogen, alkyl, aryl, aralkyl, or alkaryl.

In some embodiments of Formula (II), group $R^2$ is of formula —$(OR^5)_q$—$OR^6$. In formula —$(OR^5)_q$—$OR^6$, the variable q is an integer equal to at least 0. Stated differently, $R^2$ forms an ether or polyether group with the carbon atom to which it is attached (i.e., the carbon atom between the two dithiocarbamate or dithiocarbonate groups). In many embodiments, q is equal to 0, at least 1, at least 2, or at least 3 and up to 20 or more, up to 10, up to 8, up to 6, up to 4, or up to 2. For example, q can be in a range of 0 to 20, 0 to 10, 0 to 6, 0 to 4, or 0 to 2. When q is equal to 0, $R^2$ is equal to an alkoxy group of formula —$OR^6$. Group $R^6$ is an alkyl. Group $R^5$, if present, is an alkylene. Suitable alkyl and alkylene groups for $R^5$ and $R^6$ typically have at least 1 carbon atom, at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkyl and alkylene groups have 1 to 20 carbon atoms, 1 to 10 carbon atoms, 2 to 10 carbon atoms, 1 to 6 carbon atoms, 2 to 6 carbon atoms, or 1 to 4 carbon atoms. In many examples, where $R^2$ is of formula —$(OR^5)_q$—$OR^6$, q is 0 and $R^2$ is of formula —$OR^6$.

In other embodiments of Formula (II), group $R^2$ is of formula —C(=O)—X—$R^7$ where $R^7$ is hydrogen, alkyl, aryl, substituted alkyl, or alkaryl and where X is a single bond, oxy or —$NR^{10}$— with $R^{10}$ being hydrogen, alkyl, aryl, aralkyl, or alkaryl. That is, $R^2$ is an ester group when X is oxy, an amide group when X is —$NR^{10}$—, and a ketone group when X is a single bond. When $R^7$ and/or $R^{10}$ is an alkyl, the alkyl group typically has at least 1 carbon atom, at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkyl groups have 1 to 20 carbon atoms, 1 to 10 carbon atoms, 2 to 10 carbon atoms, 1 to 6 carbon atoms, 2 to 6 carbon atoms, or 1 to 4 carbon atoms. When $R^7$ and/or $R^{10}$ is an aryl, the aryl often has 5 to 12 carbon atoms, 6 to 12 carbon atoms, or 6 to 10 carbon atoms. The aryl is often phenyl. When $R^7$ and/or $R^{10}$ is an alkaryl, the alkaryl group often contains an arylene group having 5 to 12 carbon atoms, 6 to 12 carbon atoms, or 6 to 10 carbon atoms and an alkyl group having 1 to 10 carbon atoms, 1 to 6 carbon atoms, or 1 to 4 carbon atoms. The arylene group in the alkaryl group is often phenylene or biphenylene. When $R^{10}$ is an aralkyl, the aralkyl group often contains an alkylene group having 1 to 10 carbon atoms, 1 to 6 carbon atoms, or 1 to 4 carbon atoms and an aryl group having 5 to 12 carbon atoms, 6 to 12 carbon atoms, or 6 to 10 carbon atoms. The aryl group in the aralkyl group is often phenyl. When $R^7$ is a substituted aryl, it can be substituted with an alkyl, alkoxy, or halo. The alkyl and alkoxy substitution group often have 1 to 10 carbon atoms, 1 to 6 carbon atoms, or 1 to 4 carbon atoms and an aryl group having 5 to 12 carbon atoms, 6 to 12 carbon atoms, or 6 to 10 carbon atoms. The halo substitution group can be chloro, bromo, fluoro, or iodo.

Often, when $R^2$ is a group of formula —C(=O)—X—$R^7$, $R^7$ is an alkyl. Group X is often a single bond, oxy, or —NH—.

In many embodiments of Formula (II), the group $R^3$ is hydrogen. That is, Formula (II) is often of Formula (II-1).

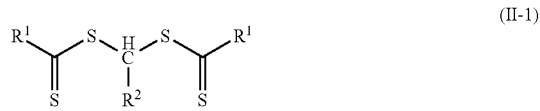

In other embodiments of Formula (II), group $R^3$ is an alkyl, aryl, aralkyl, alkaryl, a group of formula —C(=O)—$OR^8$, or a group of formula —C(=O)—$N(R^9)_2$. Groups $R^8$ and $R^9$ are each an alkyl, aryl, aralkyl, alkaryl. Where $R^3$ and/or $R^8$ and/or $R^9$ is an alkyl, the alkyl group typically has at least 1 carbon atom, at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkyl groups have 1 to 20 carbon atoms, 1 to 10 carbon atoms, 2 to 10 carbon atoms, 1 to 6 carbon atoms, 2 to 6 carbon atoms, or 1 to 4 carbon atoms. Where $R^3$ and/or $R^8$ and/or $R^9$ is an aryl, the aryl often has 5 to 12 carbon atoms, 6 to 12 carbon atoms, or 6 to 10 carbon atoms. The aryl is often phenyl. When $R^3$ and/or $R^8$ and/or $R^9$ is an alkaryl, the alkaryl group often contains an arylene group having 5 to 12 carbon atoms, 6 to 12 carbon atoms, or 6 to 10 carbon atoms and an alkyl group having 1 to 10 carbon atoms, 1 to 6 carbon atoms, or 1 to 4 carbon atoms. The arylene group in the alkaryl group is often phenylene or biphenylene. Where $R^3$ and/or $R^8$ and/or $R^9$ is an aralkyl, the aralkyl group often contains an alkylene group having 1 to 10 carbon atoms, 1 to 6 carbon atoms, or 1 to 4 carbon atoms and an aryl group having 5 to 12 carbon atoms, 6 to 12 carbon atoms, or 6 to 10 carbon atoms. The aryl group in the aralkyl group is often phenyl.

The compounds of Formula (II) can be formed using any suitable method. One such method is shown in Reaction Scheme B for compounds where $R^2$ is of formula —$(OR^5)_q$—$OR^6$. In many such compounds, q is zero and $R^2$ is —$OR^6$.

Reaction Scheme B

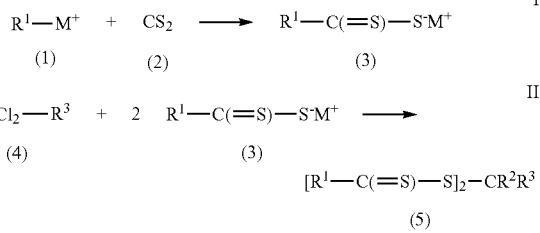

In reaction II, a compound of formula (4) is reacted with a compound of formula (3) to prepare the compound of formula (5), which corresponds to Formula (II) above. Reaction II is typically conducted at temperatures between about 0° C. and about 80° C. in the presence of an organic solvent such as acetone, acetonitrile, or an alcohol. The compound of formula (3) can be formed, for example, by treating a salt of formula (1) with carbon disulfide (Reaction I). Compound (1) is a salt of an alkoxide, aryloxide, or amine where M+ is an alkali metal, a tetralkyl ammonium ion, a trialkyl ammonium ion, or a dialkylammonium ion.

In some examples of Reaction Scheme B, a commercially available compound (4) is reacted with a commercially available compound (3). Commercially available examples of compound (4) include, but are not limited to, dichloromethyl methyl ether, dichloromethyl butyl ether, methyl dichloromethoxyacetate. Commercially available examples of compound (3) include, but are not limited to, sodium diethyldithiocarbamate trihydrate and various xanthate salts such as potassium ethyl xanthate, sodium ethyl xanthate, potassium isopropyl xanthate, sodium isopropyl xanthate, and potassium amyl xanthate.

Another method is shown in Reaction Scheme C for preparing compounds of Formula (II) where $R^2$ is an amide or ester group of formula —C(=O)—X—$R^7$ and $R^3$ is hydrogen.

Reaction Scheme C

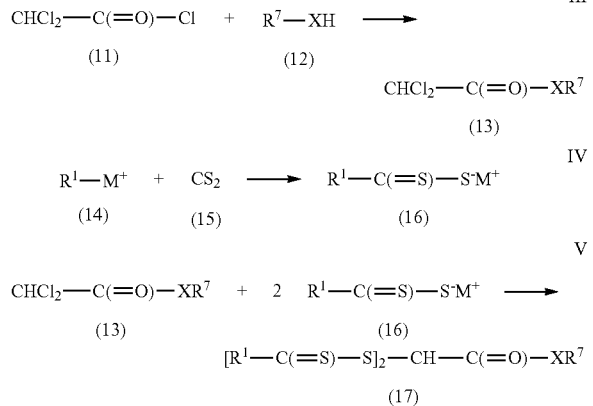

In this reaction scheme, dichloroacetyl chloride (compound (11)) is reacted (Reaction III) with a compound of formula $R^7$—XH (compound (12)), which is an alcohol ($R^7$—OH) or an amine ($R^7$—NR$^{10}$H). That is, X is either oxy or —N($R^{10}$)—. Reaction III often is conducted in the presence of a base such as, for example, trimethylamine and a catalyst such as, for example, pyridine or dimethylaminopyridine. Any organic solvent that is present is usually an aprotic solvent such as methylene chloride or tetrahydrofuran. The product of Reaction III is compound (13) of formula CHCl$_2$—C(=O)—$R^7$. Compound (13) is reacted (Reaction V) with compound (16), which can be formed by the reaction (Reaction IV) of a compound of formula $R^1$-$M^+$ (compound (14)) with carbon disulfide (15). Compound (14) is a salt of an alkoxide or of an amine where $M^+$ is usually an alkali metal ion, a tetraalkyl ammonium ion, a trialkyl ammonium ion, or a dialkylammonium ion. The reaction (Reaction V) of compound (13) with compound (16) is typically conducted at temperatures between about 0° C. and about 80° C. in the presence of an organic solvent such as acetone, acetonitrile, or an alcohol.

In some examples of Reaction Scheme C, commercially available compounds of formula CHCl$_2$—C(=O)—XR$^7$, which is compound (13), are reacted with commercially available compounds of formula $R^1$—C(=S)—S$^-$M$^+$, which is compound (16). Examples of commercially available compound (13) include, but are not limited to, methyl dichloroacetate, ethyl dichloroacetate, and butyl dichloroacetate. Examples of commercially available compound (16) include, but are not limited to, sodium diethyldithiocarbamate trihydrate and various xanthate salts such as potassium ethyl xanthate, sodium ethyl xanthate, potassium isopropyl xanthate, sodium isopropyl xanthate, and potassium amyl xanthate.

Another method of forming the compounds of Formula (II) is shown in Reaction Scheme D for compounds where $R^2$ is a ketone group of formula —C(=O)—$R^7$ and $R^3$ is hydrogen. To be a ketone group, X in the formula —CO—X—$R^7$ is a single bond.

Reaction Scheme D

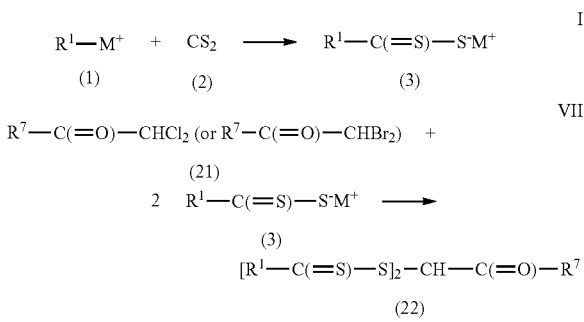

In this reaction scheme, a dihalo ketone compound (compound (21)) is reacted with a compound of formula $R^1$—C(=S)—S$^-$M$^+$, which is compound (3) as shown in Reaction VII. Compound (3) can be formed, for example, by treating a salt of formula (1) with carbon disulfide (Reaction I). Compound (1) is a salt of an alkoxide, aryloxide, or amine where M+ is an alkali metal, a tetralkyl ammonium ion, a trialkyl ammonium ion, or a dialkylammonium ion. Reaction I is often conducted at temperatures between about 0° C. and about 80° C. in the presence of an organic solvent such as acetone, acetonitrile, or an alcohol. The reaction (Reaction VII) of compound (21) with compound (3) is typically conducted at temperatures between about 0° C. and about 80° C. in the presence of an organic solvent such as acetone, acetonitrile, or an alcohol.

In some examples of Reaction Scheme D, commercially available compounds of formula $R^2$—C(=O)—CHCl$_2$ and $R^2$—C(=O)—CHBr$_2$ (compound (21)) include 1,1-dichloropropan-2-one, 2,2-dichloro-1-phenyl-ethanone, 2,2-dibromo-1-(4-bromophenyl)ethanone, 1,1-dichloro-3,3-dimethyl-2-butanone, and 1,1-dichloro-3,3-dimethyl-2-butanone. Examples of compound (3) include, but are not limited to, sodium diethyldithiocarbamate trihydrate and various xanthate salts such as potassium ethyl xanthate, sodium ethyl xanthate, potassium isopropyl xanthate, sodium isopropyl xanthate, and potassium amyl xanthate.

In some embodiments of the compounds of Formula (II), group $R^1$ is an alkoxy, aryloxy, aralkyloxy, or alkenoxy group. Such $R^1$ groups are of formula —OR$^{11}$ where $R^{11}$ is an alkyl, aryl, aralkyl, or alkenyl group. That is the compound is of Formula (II-A).

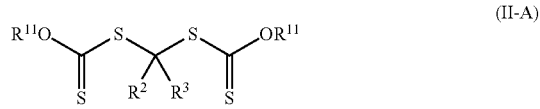

These compounds are bis-dithiocarbonate compounds having a single carbon atom between the two dithiocarbonate groups.

In some other more specific compounds of Formula (II-A), $R^{11}$ is an alkenyl (i.e., —$OR^{11}$ is an alkenyloxy), $R^2$ is an alkoxy ($R^2$ is of formula —$(OR^5)_q$—$OR^6$ where q is zero, which is equal to —$OR^6$), and $R^3$ is hydrogen. A specific example compound includes, but it not limited to, 1,1-bis(10-undecenyloxycarbothioylsulfanyl)methyl ether.

In other more specific compounds of Formula (II-A), $R^{11}$ is an alkyl (i.e., —$OR^{11}$ is an alkoxy), $R^2$ is an alkoxy ($R^2$ is of formula —$(OR^5)_q$—$OR^6$ where q is zero, which is equal to —$OR^6$), and $R^3$ is of formula —$C(=O)$—$OR^8$ where $R^8$ is an alkyl. A specific example is methyl 2,2-bis(isopropoxycarbothioylsulfanyl)-2-methoxy-acetate.

In some embodiments of Formula (II-A), $R^3$ is hydrogen, $R^2$ is an alkoxy ($R^2$ is of formula —$(OR^5)_q$—$OR^6$ where q is zero, which is equal to —$OR^6$), and $R^1$ of Formula (II) is an alkoxy, aralkyloxy, or alkenyloxy. Such compounds are of Formula (II-A1).

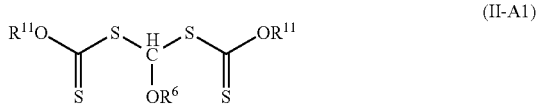

(II-A1)

Groups $R^{11}$ is an alkyl, aralkyl, or alkenyl. In many embodiments of Formula (II-A1), $R^6$ is an alkyl. Specific example compounds include, but are not limited to, 1,1-bis(isopropoxycarbothioylsulfanyl)methyl methyl ether, 1,1-bis(isopropoxycarbothioylsulfanyl)methyl butyl ether, or 1,1-bis(ethoxycarbothioylsulfanyl)methyl butyl ether.

In other embodiments of Formula (II-A), $R^3$ is hydrogen, $R^2$ is a group of formula —$C(=O)$—$X$—$R^7$, and $R^1$ is an alkoxy, aralkyloxy, or alkenyloxy. Such compounds are of Formula (II-A2).

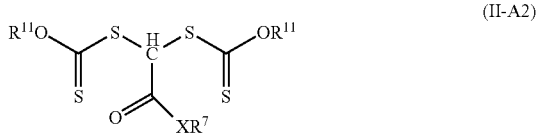

(II-A2)

Groups $R^{11}$ is an alkyl, aralkyl, or alkenyl. The group $R^{11}$ is often an alkyl. Examples of compounds of Formula (II-A2 where X is equal to oxy and $R^7$ is an alkyl include, but are not limited to, 2-ethylhexyl 2,2-bis(isopropoxycarbothioylsulfanyl)acetate, methyl 2,2-bis(isopropoxycarbothioylsulfanyl)acetate, and tert-butyl 2,2-bis(isopropoxycarbothioylsulfanyl)acetate. An example compound of Formula (II-A2) where X is a single bond and $R^7$ is an alkyl is 1,1-bis(isopropoxycarbothioylsulfanyl)-2-propanone.
Examples of compounds of Formula (II-A2) where X is a single bond and $R^7$ is an aryl or substituted aryl are 2,2-bis(isopropoxycarbothioylsulfanyl)-1-phenylethanone and 2,2-bis(isopropoxycarbothioylsulfanyl)-1-(4-bromophenyl) ethanone. An example of a compound of Formula (II-A2) where X is equal to oxy and $R^7$ is an aryl is phenyl 2,2-bis(isopropoxycarbothioylsulfanyl)acetate. An example of a compound of Formula (II-A2) where X is equal to —$NR^{10}$— is N,N-dibutyl-2,2-bis(isopropoxycarbothioylsulfanyl)acetamide. In this compound both $R^7$ and $R^{10}$ are alkyl (i.e., butyl) groups.

In other embodiments of the compound of Formula (II), group $R^1$ is of formula —$N(R^4)_2$ as shown in Formula (II-B).

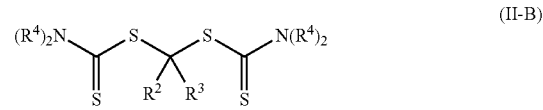

(II-B)

These compounds are bis-dithiocarbamate compounds having a single carbon atom between the two dithiocarbonate groups.

In some embodiments of Formula (II-B), $R^3$ is hydrogen and $R^2$ is an alkoxy ($R^2$ is of formula —$(OR^5)_p$—$OR^6$ where p is zero, which is equal to —$OR^6$). Such compounds are of Formula (II-B1).

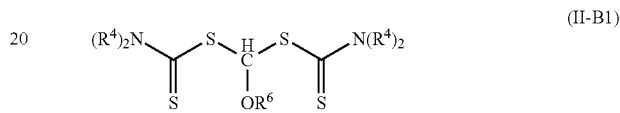

(II-B1)

In many such compounds, each $R^4$ is an alkyl. Specific example compounds include, but are not limited to, 1,1-bis(diethylcarbamothioylsulfanyl)methyl butyl ether and 1,1-bis(diethylcarbamothioylsulfanyl)methyl methyl ether.

In other embodiments of Formula (II-B), $R^3$ is hydrogen and $R^2$ is a group of formula —$C(=O)$—$X$—$R^7$. Such compounds are of Formula (II-B2).

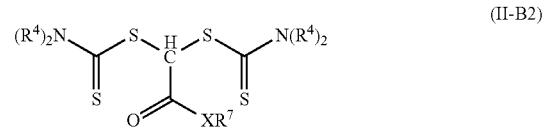

(II-B2)

The group $R^7$ is often an alkyl. Examples of compounds of Formula (II-B2) where X is equal to oxy and $R^7$ is an alkyl include, but are not limited to, 2-ethylhexyl 2,2-bis(diethylcarbamothioylsulfanyl)acetate, methyl 2,2-bis(diethylcarbamothioylsulfanyl)acetate, and octyl 2,2-bis(diethylcarbamothioylsulfanyl)acetate.

Other example thiocarbonylthio-containing compounds are of Formula (III).

$R^1$—$C(=S)$—$S$—$CH_2$—$R^{12}$ (III)

Group $R^1$ is the same as defined above for the thiocarbonylthio-containing group. $R^{12}$ is a group of formula —$C(=O)$—$OR^{13}$ where each $R^{13}$ is hydrogen, alkyl, aryl, aralkyl, or alkaryl, a group of formula —$C(=O)R^{14}$ where each $R^{14}$ is independently alkyl, aryl, aralkyl, or alkaryl, a group of formula —$OR^{15}$ where $R^{15}$ is alkyl, aryl, aralkyl, or alkaryl, or a group of formula —$C(=O)$—$N(R^{16})_2$ where $R^{16}$ is each independently hydrogen or alkyl. When $R^{13}$ is hydrogen, the $R^{12}$ group may be neutralized such that it is a group of the formula —$C(=O)$—$O^-M^+$, where M+ is an alkali metal, a tetraalkyl ammonium ion, a trialkyl ammonium ion, or a dialkylammonium ion.

Suitable $R^{13}$, $R^{14}$, $R^{15}$, and $R^{16}$ alkyl groups typically have at least 1 carbon atom, at least 2 carbon atoms, at least 3 carbon atoms, or at least 4 carbon atoms and can have up to 20 carbon atoms, up to 18 carbon atoms, up to 16 carbon atoms, up to 12 carbon atoms, or up to 10 carbon atoms. Some example alkyl groups have 1 to 20 carbon atoms, 1 to 10 carbon atoms, 2 to 10 carbon atoms, 1 to 6 carbon atoms, 2 to 6 carbon atoms, or 1 to 4 carbon atoms.

Suitable $R^{13}$, $R^{14}$, or $R^{15}$ aryl groups typically have 5 to 12 carbon atoms, 6 to 12 carbon atoms, or 6 to 10 carbon atoms. In many embodiments, the aryl group is phenyl.

Suitable $R^{13}$, $R^{14}$, or $R^{15}$ aralkyl groups typically contains an alkylene group having 1 to 10 carbon atoms, 1 to 6 carbon atoms, or 1 to 4 carbon atoms and an aryl group having 5 to 12 carbon atoms, 6 to 12 carbon atoms, or 6 to 10 carbon atoms. The aryl group in the aralkyl group is often phenyl.

Suitable $R^{13}$, $R^{14}$, or $R^{15}$ alkaryl groups typically contains an arylene group having 5 to 12 carbon atoms, 6 to 12 carbon atoms, or 6 to 10 carbon atoms and an alkyl group having 1 to 10 carbon atoms, 1 to 6 carbon atoms, or 1 to 4 carbon atoms. The arylene group in the alkaryl group is often phenylene or biphenylene.

Examples of thiocarbonylthio-containing compounds of Formula (III) include, but are not limited to, methyl 2-ethoxycarbothioylsulfanylacetate (where $R^1$ is ethoxy and $R^{12}$ is a group of formula —C(=O)—OR$^{13}$ where $R^{13}$ is an methyl), 2-ethoxycarbothioylsulfanylacetate sodium salt (where $R^1$ is ethoxy and $R^{12}$ is a group of formula —C(=O)—O$^-$Na$^+$), O-ethyl-(2-amino-2-oxo-ethyl)sulfanylmethanethioate (where $R^1$ is ethoxy and $R^{12}$ is of formula —C(=O)—N(R$^{16}$)$_2$ where each $R^{16}$ is hydrogen), and isopropylxanthoylmethyloctyl ether (where $R^1$ is isopropoxy and $R^{12}$ is a group of formula —OR$^{15}$ with $R^{15}$ being an n-octyl).

The amount of the thiocarbonylthio-containing groups attached to the polymeric substrate is typically in a range of 0.1 to 100 micromoles per gram of the first article (i.e., micromoles per gram of the functionalized substrate). The amount is often at least 0.2, at least 0.5, at least 1, at least 2, at least 4, at least 5, or at least 10 micromoles per gram and is often up to 100, up to 80, up to 60, up to 40, up to 30, or up to 20 micromoles per gram.

No monomers having a free radically polymerizable group such as an ethylenically unsaturated group are present when the thiocarbonylthio-containing compounds are reacted with the treated substrate. This tends to increase the likelihood that the thiocarbonylthio group will be transferred to the treated substrate, and thus may increase the density of the thiocarbonylthio-containing groups on the surface of the polymeric substrate. This also allows the preparation and isolation of a functionalized substrate with covalently attached thiocarbonylthio-containing groups in the absence of any competing polymerization or grafting reactions and may allow better control over subsequent contemplated grafting (polymerization) reactions. There is no polymeric material formed in solution simultaneously with the formation of the functionalized substrate.

The functionalized substrate is a first article in the preparation of a second article having attached polymeric chains. More specifically, a method of preparing the second article includes preparing a reaction mixture by contacting the first article (i.e., functionalized substrate) having attached thiocarbonylthio groups with a radically polymerizable monomer composition. The method yet further includes exposing the reaction mixture to actinic radiation and to form the second article with attached polymeric chains, the polymeric chains being a polymerized product of the radically polymerizable monomer composition. At least some of the polymeric chains are terminated with a thiol group or with a thiocarbonylthio-containing group.

In this method, the functionalized substrate (i.e., first article) is prepared as described above. The functionalized substrate, which has thiocarbonylthio groups of formula —SC(=S)—R$^1$ covalently attached to the surface of the polymeric substrate, is placed in contact with a radically polymerizable monomer composition to form a reaction mixture. When the reaction mixture comprising the radically polymerizable monomer composition, which contains a first monomer, is exposed to actinic radiation such as ultraviolet radiation, polymerization can occur with the thiocarbonylthio-containing group functioning as an iniferter (e.g., photoiniferter). The polymerization process is shown schematically in Reaction Scheme E.

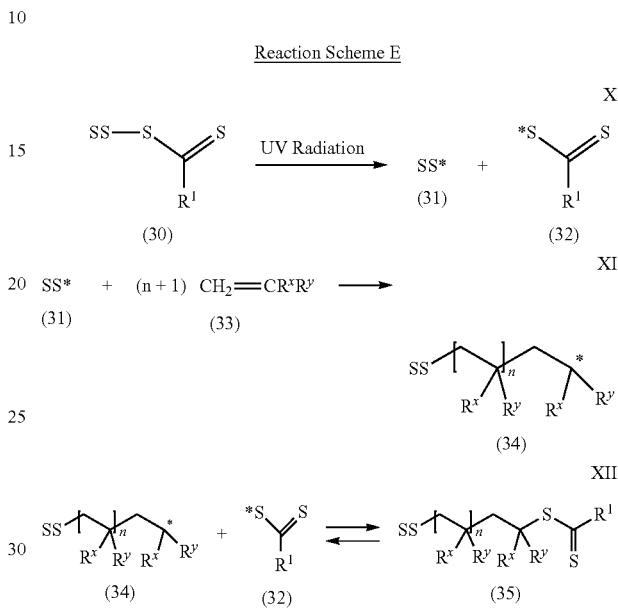

In Reaction Scheme E, exposure to actinic radiation (e.g., ultraviolet radiation) results in formation of a radical on the substrate surface (31) and a radical of the thiocarbonylthio-containing group (32) as shown in Reaction X. A first monomer (shown for simplicity as CH$_2$=CR$^x$R$^y$ (33) in Reaction Scheme E) reacts with the radical on the substrate surface (31) resulting in the generation of a second radical that can react with another monomer. The polymerization of the (n+1) moles of the first monomer is shown as compound (34) in Reaction XI. At any point in this process, the growing radical (34) may recombine with the thiocarbonylthio radical (32) to form a terminated chain as shown as compound (35) in Reaction XII. Upon continued exposure to actinic radiation, the radical (34) and the thiocarbonylthio radical (32) can form again from compound (35). If more monomers are present, the regenerated radical (34) can undergo further polymerization. Eventually, this radical will combine with a thiocarbonylthio radical (32). The polymerization reaction stops when exposure to actinic radiation is stopped. The product is a second article having a plurality of polymeric chains grafted to the polymeric substrate. At least some of the polymeric chains are terminated with a thiol group or a thiocarbonylthio-containing group. Often, the thiocarbonylthio-containing group is of formula —S—C(=S)—R$^1$ as shown as the product of Reaction XII.

Although less preferred, the process shown in Reaction Scheme E may also be carried out through the use of thermal energy, as is well known in the art for iniferter compounds (see, for example, T. Otsu, J. Polym. Sci., Part A: Polym. Chem., 38, 2121-2136 (2000)).

The radically polymerizable monomer composition in the reaction mixture contains a first monomer having (a) at least one ethylenically unsaturated group, (b) at least one ligand functional group that is an acidic group, basic group, or salt thereof, (c) a spacer group that directly links the at least one ethylenically unsaturated group and the at least one ligand functional group by a chain of at least six catenated atoms. The first monomer can be in a neutral state but can be negatively charged (if acidic) or positively charged (if basic) under some pH conditions. The first monomer can be permanently charged (for example, when the ligand functional group is in the form of a quaternary ammonium salt).

The first monomer can include a single ethylenically unsaturated group or multiple ethylenically unsaturated groups (for example, two or three or up to as many as six), which can be the same or different in nature (preferably, the same). The first monomer often has only one ethylenically unsaturated group.

The first monomer has an acidic group, a basic group, or a salt thereof. The acidic groups and the basic groups are not a polypeptide or protein. As used herein, the term "polypeptide" refers to a compound that contains more than four amino acid units.

Suitable acidic groups of the first monomer include those that exhibit at least a degree of acidity (which can range from relatively weak to relatively strong), as well as salts thereof. Such acidic groups or salts thereof include those commonly utilized as ion exchange or metal chelate type ligands. The acid groups are often selected from carboxy, phosphono, phosphato, sulfono, sulfato, boronato, and combinations thereof. In certain embodiments, the acidic group(s) include carboxy, phosphono, sulfono, and combinations thereof. In certain embodiments, the acidic group is a carboxy group. If the acidic group is a salt, the counterion is often selected from an alkali metal (for example, sodium or potassium), alkaline earth metal (for example, magnesium or calcium), ammonium, and tetraalkylammonium, and the like, and combinations thereof.

Suitable basic groups of the first monomer include those that exhibit at least a degree of basicity (which can range from relatively weak to relatively strong), as well as salts thereof. Such basic groups or salts thereof include those commonly utilized as ion exchange or metal chelate type ligands. The basic group is often a tertiary amino group, quaternary amino group, guanidino group, or biguanidino group. If the basic group is a salt, the counterion is often selected from a halide (e.g., chloride or bromide), carboxylate (e.g., acetate), nitrate, phosphate, bisulfate, methyl sulfate, hydroxide ions, and the like, and combinations thereof.

The spacer group of the monomer(s) can be directly linked to at least one ethylenically unsaturated group and at least one ligand functional group thereof by a chain of at least 6 catenated atoms. Thus, the chain can include 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more catenated atoms (for example, including up to as many as 40 or 50). In certain embodiments, the chain includes at least 7 catenated atoms (more preferably, at least 8, and even more preferably, at least 9, at least 10, at least 11, or at least 12 catenated atoms) and/or includes no more than 30 catenated atoms (more preferably, no more than 25, even more preferably, no more than 20, and even more preferably, no more than 16 catenated atoms). If the monomer has a (meth) acryloyl group, the carbonyl of this group is counted as being part of the spacer group.

Although not wishing to be bound by theory, the length of the chain may contribute to adoption of helical or partially helical conformations by the polymer backbone (formed through monomer polymerization). When the chain is relatively short (for example, less than 6 catenated atoms), ionic repulsion between acidic groups or between basic groups may force the polymer backbone into a random coil type conformation. As chain length increases, adoption of helical conformations may become possible and may be maximized at chain lengths of 8 to 14 catenated atoms. A helical conformation of substrate-grafted polymer may facilitate presentation of the acidic group(s), basic group(s), or salt(s) thereof, for interaction with target biomaterials, such as viruses and other microorganisms, proteins, cells, endotoxins, acidic carbohydrates, nucleic acids, and the like.

In certain embodiments, spacer groups include at least one hydrogen bonding moiety, which is defined above as a moiety including at least one hydrogen bond donor and at least one hydrogen bond acceptor (both of which are heteroatom-containing). Example hydrogen donors are imino, thio, and hydroxy groups. Example hydrogen acceptors are carbonyl, carbonyloxy, or ether oxygen. More preferred spacer groups include at least two hydrogen bonding moieties or include at least one hydrogen bonding moiety and at least one hydrogen bond acceptor that is distinct from (not part of) the hydrogen bonding moiety.

In certain embodiments, hydrogen bonding moieties include those that include at least two hydrogen bond donors (for example, donors such as imino, thio, or hydroxy), at least two hydrogen bond acceptors (for example, acceptors in the form of a carbonyl, carbonyloxy, or ether oxygen), or both. For example, an iminocarbonylimino moiety (having two N—H donors and at least two acceptors in the form of two lone electron pairs on carbonyl) can sometimes be preferred over a single iminocarbonyl moiety. In certain embodiments, the spacer groups include those that include at least one iminocarbonylimino moiety (more preferably, in combination with at least one acceptor such as carbonyloxy), at least two iminocarbonyl moieties, or a combination thereof.

The hydrogen bond donor and hydrogen bond acceptor of the hydrogen bonding moiety can be adjacent (directly bonded) to each other or can be non-adjacent (preferably, adjacent or separated by a chain of no more than 4 catenated atoms; more preferably, adjacent). The heteroatoms of the hydrogen bond donor and/or hydrogen bond acceptor can be located within the chain of catenated atoms of the spacer group or, alternatively, can be located within chain substituents.

Although hydrogen bond donors can also function as hydrogen bond acceptors (through a lone electron pair of the donor's heteroatom), the hydrogen bonding moiety preferably includes distinct donor and acceptor moieties. This can facilitate intramolecular (intermonomer) hydrogen bond formation. Although not wishing to be bound by theory, such intramolecular hydrogen bonds between adjacent monomer or near neighbor repeat units in the polymer molecule may contribute to at least a degree of spacer group stiffening, which may facilitate presentation of the acidic group(s), basic group(s), or salt(s) thereof for interaction with target biomaterials.

In certain embodiments, hydrogen bonding moieties include carbonylimino, thiocarbonylimino, iminocarbonylimino, iminothiocarbonylimino, oxycarbonylimino, oxythiocarbonylimino, and the like, and combinations thereof. In certain embodiments, hydrogen bonding moieties include carbonylimino, iminocarbonylimino, oxycarbonylimino, and combinations thereof (more preferably, carbonylimino, iminocarbonylimino, and combinations thereof). In certain embodiments, spacer groups include those that are divalent, trivalent, or tetravalent (more preferably, divalent or trivalent; and even more preferably, divalent).

A class of useful first monomers are those of Formula (IV).

$$CH_2=CR^{21}-C(=O)-X^1-R^{22}-[Z-R^{22}]_n-L \qquad (IV)$$

In Formula (IV), group $R^{21}$ is selected from hydrogen, alkyl, aryl, and combinations thereof. Each group $R^{22}$ is independently a (hetero)hydrocarbylene. Group $X^1$ is —O— or —$NR^{23}$— where $R^{23}$ is selected from hydrogen or hydrocarbyl. Group Z is heterohydrocarbylene including at least one hydrogen bond donor, at least one hydrogen bond acceptor, or a combination thereof. The variable n is an integer of 0 or 1. Group L is a ligand functional group that is an acidic group, a basic group, or salt thereof.

The monomers of Formula (IV) have an ethylenically unsaturated group of formula $CH_2=CR^{21}$— where $R^{21}$ is hydrogen, alkyl, aryl, or combinations thereof. In most embodiments, $R^{21}$ is either hydrogen or methyl.

Each $R^{22}$ is independently a (hetero)hydrocarbylene. Example hydrocarbylenes include alkylene groups, arylene groups, aralkylene groups, and alkarylene groups. Example heterohydrocarbylenes include heteroaralkylene, hydroxy-substituted alkylene, and hydroxy-substituted aralkylene. In certain embodiments, each $R^{22}$ is independently hydrocarbylene. For example, each $R^{22}$ is independently alkylene.

In certain embodiments, $X^1$ is —O— (oxy) or —$NR^{23}$—. Group $R^{23}$ is hydrogen or hydrocarbyl. The hydrocarbyl can be an alkyl or aryl. In many examples, $R^{23}$ is hydrogen.

In certain embodiments, Z is heterohydrocarbylene including at least one hydrogen bond donor, at least one hydrogen bond acceptor, or a combination thereof. Hydrogen donors are typically donors such as imino, thio, or hydroxy. Hydrogen acceptors are typically carbonyl, carbonyloxy, or ether oxygens. Thus, group Z is often a hydrogen bonding moiety such as carbonylimino, thiocarbonylimino, iminocarbonylimino, iminothiocarbonylimino, oxycarbonylimino, oxythiocarbonylimino, and the like, and combinations thereof. In certain embodiments, hydrogen bonding moieties include carbonylimino, iminocarbonylimino, oxycarbonylimino, and combinations thereof (more preferably, carbonylimino, iminocarbonylimino, and combinations thereof).

In certain embodiments, n is an integer of 1 in the monomers of Formula (IV).

In certain embodiments, L is a ligand functional group including at least one acidic group or salt thereof selected from carboxy, phosphono, phosphato, sulfono, sulfato, boronato, and combinations thereof (more preferably, selected from carboxy, phosphono, sulfono, and combinations thereof). In other embodiments, L is a functional group including at least one basic group or salt thereof. The basic group is typically a tertiary amino group, a quaternary amino group, a guanidino group, or a biguanidino group. In some embodiments, L is a carboxy, guanidino, or a salt thereof.

Such monomers can be prepared by known synthetic methods or by analogy to known synthetic methods. For example, amino group-containing carboxylic, sulfonic, or phosphonic acids can be reacted with ethylenically unsaturated compounds that include at least one group that is reactive with an amino group. Similarly, acidic group-containing compounds that also contain a hydroxy group can be reacted with ethylenically unsaturated compounds that include at least one group that is reactive with a hydroxy group, optionally in the presence of a catalyst.

Preferred monomers are (meth)acryloyl-containing monomers, which refers to acryloyl-containing monomers and/or methacryloyl-containing monomers. Similarly, the term "(meth)acrylate" refers to an acrylate and/or a methacrylate monomer. In such monomers, the carbonyl group is part of the spacer group.

Representative examples of useful monomers of Formula (IV) can be prepared by reacting an alkenyl azlactone of Formula (V)

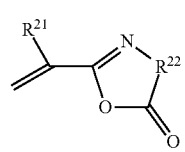

with a compound (or salt thereof) of Formula (VI).

$$H-X^2-R^{22}-L \qquad (VI)$$

The groups $R^{21}$, $R^{22}$, and L are defined as in Formula (IV). Groups $X^2$ is oxy or —$NR^{23}$— where $R^{23}$ is hydrogen or hydrocarbyl (e.g., alkyl or aryl). The resulting compounds are of Formula (IV-1).

$$CH_2=CR^{21}-C(=O)-NH-R^{22}-C(=O)-X^2-R^{22}-L \qquad (IV-1)$$

These compounds are of Formula (IV) where $X^1$ is —NH—, the variable n is equal to 1, and Z is equal to —C(=O)—$X^2$—.

Representative examples of useful alkenyl azlactones of Formula (V) include 4,4-dimethyl-2-vinyl-4H-oxazol-5-one (vinyldimethylazlactone, VDM), 2-isopropenyl-4H-oxazol-5-one, 4,4-dimethyl-2-isopropenyl-4H-oxazol-5-one, 2-vinyl-4,5-dihydro-[1,3]oxazin-6-one, 4,4-dimethyl-2-vinyl-4,5-dihydro-[1,3]oxazin-6-one, 4,5-dimethyl-2-vinyl-4,5-dihydro-[1,3]oxazin-6-one, and the like, and combinations thereof.

Other representative examples of useful monomers of Formula (IV) can be prepared by reacting an (meth)acryloyl isocyanate monomer of Formula (VII)

$$CH_2=CR^{21}-C(=O)-X^1-R^{22}-N=C=O \qquad (VII)$$

with a compound (or salt thereof) of Formula (VI) as described above. The resulting monomers are of Formula (IV-2).

$$CH_2=CR^{21}-C(=O)-X^1-R^{22}-NH-C(=O)-X^2-R^{22}-L \qquad (IV-2)$$

These monomers are of Formula (IV) where the variable n is equal to 1 and Z is equal to —NH—C(=O)—$X^2$—. The groups $R^{21}$, $R^{22}$, $X^1$, $X^2$, and L are the same as defined above.

Representative examples of ethylenically unsaturated isocyanates of Formula (VII) include 2-isocyanatoethyl (meth)acrylate (IEM or IEA), 3-isocyanatopropyl (meth)acrylate, 4-isocyanatocyclohexyl (meth)acrylate, and the like, and combinations thereof.

Representative examples of useful compounds of Formula (VI) that can provide an acidic L group (or salt thereof) include amino group-containing carboxylic, sulfonic, boronic, and phosphonic acids and combinations thereof, or salts thereof. Useful amino carboxylic acids include α-amino acids (L-, D-, or DL-α-amino acids) such as glycine, alanine, valine, proline, serine, phenylalanine, histidine, tryptophan, asparagine, glutamine, N-benzylglycine, N-phenylglycine, sarcosine, and the like; β-aminoacids such as β-alanine, homoleucine, homoglutamine, homophenylalanine, and the like; other α, ω-aminoacids such as γ-aminobutyric acid, 6-aminohexanoic acid, 11-aminoundecanoic acid, and the like; and combinations thereof. Useful amino sulfonic acids include aminomethanesulfonic acid, 2-aminoethanesulfonic acid (taurine), 3-amino-1-propanesulfonic acid, 6-amino-1-hexanesulfonic acid, and the like, and combinations thereof. Useful aminoboronic acids include m-aminophenylboronic acid, p-aminophenylboronic acid, and the like, and combinations thereof. Useful aminophosphonic acids include 1-aminomethylphosphonic acid, 2-aminoethylphosphonic acid, 3-aminopropylphosphonic acid, and the like, and combinations thereof.

Representative examples of other useful compounds of Formula (VI) having an acidic L group (or salt thereof) include compounds including a hydroxy group and an acidic group. Specific examples include glycolic acid, lactic acid, 6-hydroxyhexanoic acid, citric acid, 2-hydroxyethylsulfonic acid, 2-hydroxyethylphosphonic acid, and the like, and combinations thereof.

Still other representative compounds of Formula (VI) having an acidic L group (or salt thereof) are those that contain more than one acidic group include aspartic acid, glutamic acid, α-aminoadipic acid, iminodiacetic acid, $N_\alpha$, $N_\alpha$-bis(carboxymethyl)lysine, cysteic acid, N-phosphonomethylglycine, and the like, and combinations thereof.

Many of the above-described compounds of Formula (VI) that have an acidic L group (or salt thereof) are commercially available. Still other useful acidic group-containing compounds can be prepared by common synthetic procedures. For example, various diamines or aminoalcohols can be reacted with one equivalent of a cyclic anhydride to produce an intermediate acidic group-containing compound including a carboxyl group and an amino or hydroxy group.

In addition, useful monomers having an acidic group can be prepared by reaction of hydroxy- or amine-containing (meth)acrylate or (meth)acrylamide monomers with a cyclic anhydride to produce carboxyl group-containing monomers.

In certain embodiments, useful monomers of Formula (IV) having an L group that is an acidic group (or salt thereof) may be prepared from the reaction of alkenyl azlactones with aminocarboxylic acids, monomers prepared from the reaction of alkenyl azlactones with aminosulfonic acids, monomers prepared from the reaction of ethylenically unsaturated isocyanates with aminocarboxylic acids, monomers prepared from the reaction of ethylenically unsaturated isocyanates with aminosulfonic acids, or combinations thereof.

Some example monomers having a group L in Formula (IV) that is an acidic group or salt thereof are the following (which are shown as acids, but salts of such acids may also be used):

VDM-4-aminomethyl-cyclohexanecarboxylic acid:

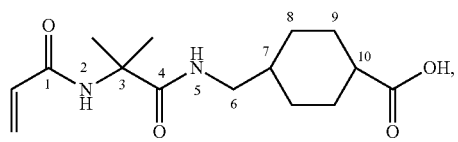 [SMILES: C=CC(=O)NC(C)(C)C(=O)NCC1CCC(C(=O)O)CC1]

VDM-2-hydroxy-4-aminobutanoic acid:

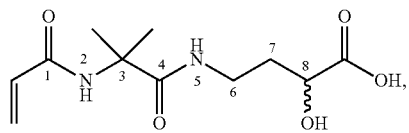 [SMILES: C=CC(=O)NC(C)(C)C(=O)NCCC(O)C(=O)O]

VDM-2-amino-3-hydroxypropanoic acid (VDM-serine):

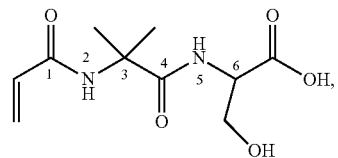 [SMILES: C=CC(=O)NC(C)(C)C(=O)NC(CO)C(=O)O]

VDM-2-amino-3-(4-hydroxyphenyl)propanoic acid (VDM-tyrosine):

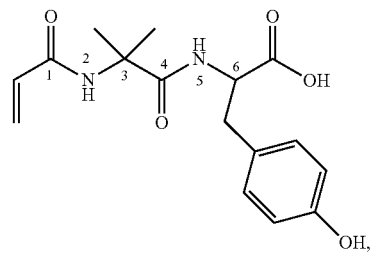 [SMILES: C=CC(=O)NC(C)(C)C(=O)NC(Cc1ccc(O)cc1)C(=O)O]

VDM-(2S)-2-amino-3-(1H-indol-3-yl)propanoic acid (VDM-tryptophan):

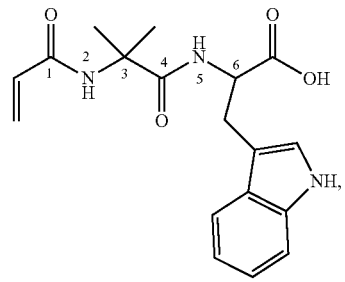 [SMILES: C=CC(=O)NC(C)(C)C(=O)NC(Cc1c[nH]c2ccccc12)C(=O)O]

VDM-7-aminoheptanoic acid:

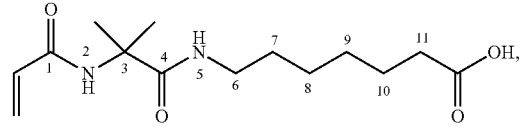 [SMILES: C=CC(=O)NC(C)(C)C(=O)NCCCCCCC(=O)O]

VDM-2-amino-3-(1H-imidazol-4-yl)propanoic acid (VDM-histidine):

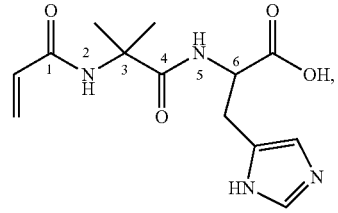 [SMILES: C=CC(=O)NC(C)(C)C(=O)NC(Cc1cnc[nH]1)C(=O)O]

IEM-3-aminopropanoic acid:

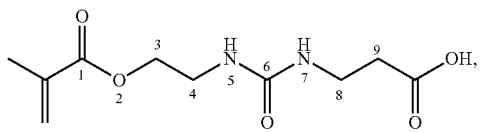 [SMILES: C=C(C)C(=O)OCCNC(=O)NCCC(=O)O]

IEM-taurine:

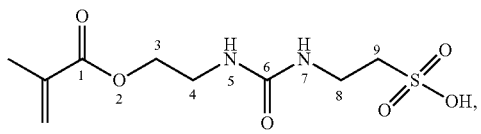 [SMILES: C=C(C)C(=O)OCCNC(=O)NCCS(=O)(=O)O]

VDM-taurine:

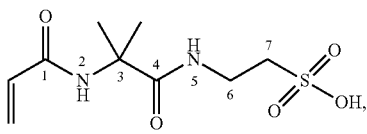 [SMILES: C=CC(=O)NC(C)(C)C(=O)NCCS(=O)(=O)O]

VDM-2-(hydroxyethyl)phosphonic acid:

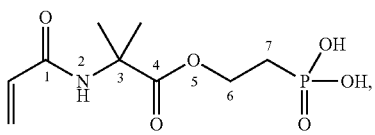 [SMILES: C=CC(=O)NC(C)(C)C(=O)OCCP(=O)(O)O]

VDM-3-aminopropanoic acid:

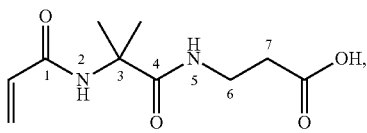 [SMILES: C=CC(=O)NC(C)(C)C(=O)NCCC(=O)O]

VDM-4-aminobutyric acid:

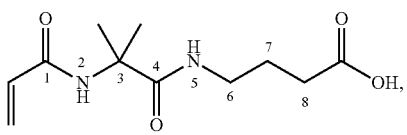 [SMILES: C=CC(=O)NC(C)(C)C(=O)NCCCC(=O)O]

VDM-5-aminovaleric acid:

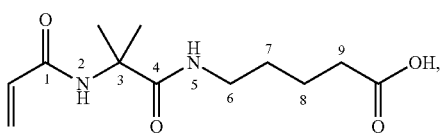 [SMILES: C=CC(=O)NC(C)(C)C(=O)NCCCCC(=O)O]

VDM-6-aminocaproic acid:

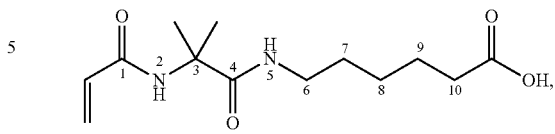

VDM-Phenylalanine:

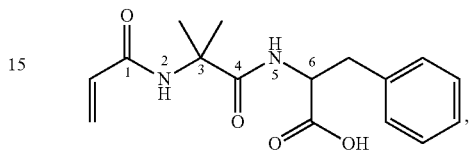

and

IEM-Phenylalanine:

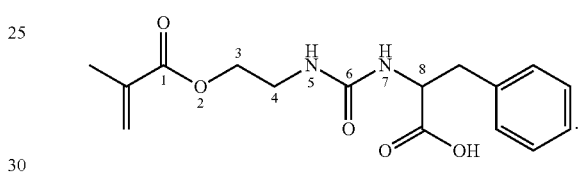

Representative examples of useful compounds of Formula (VI) that can provide a basic L group often contain at least one amino or hydroxy group and at least one basic group such as a tertiary or quaternary amino group. Specific examples include 2-(dimethylamino)ethylamine, 3-(diethylamino)propylamine, 6-(dimethylamino)hexylamine, 2-aminoethyltrimethylammonium chloride, 3-aminopropyltrimethylammonium chloride, 2-(dimethylamino)ethanol, 3-(dimethylamino)-1-propanol, 6-(dimethylamino)-1-hexanol, 1-(2-aminoethyl)pyrrolidine, 2-[2-(dimethylamino)ethoxy]ethanol, histamine, 2-aminomethylpyridine, 4-aminomethylpyridine, 4-aminoethylpyridine, and the like, and combinations thereof.

Some example monomers having a group L in Formula (IV) that is a basic group such as a tertiary or quaternary amino group are the following:

VDM-2-aminoethyltrimethylammonium chloride:

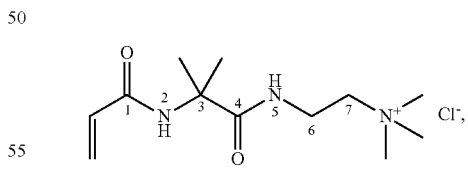

IEM-2-aminoethyltrimethylammonium chloride:

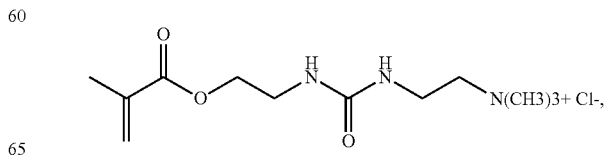

and

VDM adducts of dimethylaminoalkanols:

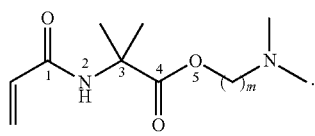

Some monomers of Formula (IV) have an L group that is a guanidino or biguanidino group. That is, L is of formula —$NR^{24}$—[C(=$NR^{24}$)—$NR^{24}]_m R^{25}$ where m is 1 or 2. When m is equal to 1, group L is a guanidino group and when m is equal to 2, group L is a biguanidino group. Group $R^{24}$ is hydrogen or hydrocarbyl and group $R^{25}$ is hydrogen, hydrocarbyl, or —$N(R^{24})_2$. Suitable hydrocarbyl groups for $R^{24}$ and $R^{25}$ are often aryl or alkyl groups. In many embodiments, $R^{24}$ and/or $R^{25}$ are hydrogen. Such monomers can be prepared as described in PCT Patent Applications WO 2014/204763 (Rasmussen et al.) and WO 2013/184366 (Bothof et al.).

Monomers with guanidino or biguanidino groups can be prepared, for example, by reaction of a (meth)acryloyl halide (e.g., (meth)acryloyl chloride), a (meth)acryloyl isocyanate (as in Formula (VI) above), or an alkenyl azlactone (as in Formula (V) above) with a compound of Formula (VIII).

$$HNR^{23}-R^{22}-NR^{24}-[C(=NR^{24})-NR^{24}]_m R^{25} \quad (VIII)$$

The compounds of Formula (VIII) correspond to compounds of Formula (VI) where $X^2$ is —$NR^{23}$— and L is —$NR^{24}$—[C(=$NR^{24}$)—$NR^{24}]_m R^{25}$. These compounds can be formed by reaction of a diamine with a guanylating agent as described, for example, in PCT Patent Application WO 2014/204763 (Rasmussen et al.). The groups $R^{22}$, $R^{23}$, $R^{24}$, and $R^{25}$ plus the variable m are the same as described above. Some compounds of Formula (VIII) are available commercially, for example, 4-aminobutylguanidine (agmatine).

When the compound of Formula (VIII) is reacted with an alkenyl azlactone, a monomer of Formula (IV-3) is formed.

$$CH_2=CR^{21}-C(=O)-NH-R^{22}-C(=O)-NR^{23}-R^{22}-NR^{24}-[C(=NR^{24})-NR^{24}]_m R^{25} \quad (IV-3)$$

This monomer is of Formula (IV) where n is equal to 1, Z is —C(=O)—$NR^{23}$—, and $X^1$ is —NH—. The groups $R^{21}$, $R^{22}$, $R^{23}$, $R^{24}$, and $R^{25}$ plus the variable m are the same as described above.

When the compound of Formula (VIII) is reacted with (meth)acryloyl isocyanate, a monomer of Formula (IV-4) is formed.

$$CH_2=CR^{21}-C(=O)-X^1-R^{22}-NH-C(=O)-NR^{23}-R^{22}-NR^{24}-[C(=NR^{24})-NR^{24}]_m R^{25} \quad (IV-4)$$

This monomer is of Formula (IV) where n is equal to 1, Z is —NH—C(=O)—$NR^{23}$—, L is of formula —$NR^{24}$—[C(=$NR^{24}$)—$NR^{24}]_m R^{25}$. The groups $R^{21}$, $R^{22}$, $R^{23}$, $R^{24}$, and $R^{25}$ plus the variable m are the same as described above.

Some specific examples of the first monomer having a guanidino group for L are shown below. The structures are shown as neutral compounds for simplicity but can be present as various salts such as, for example, chloride salts or sulfate salts:

2-({[(4-[amino(imino)methyl]aminobutyl)amino]carbonyl}-amino)ethyl methacrylate

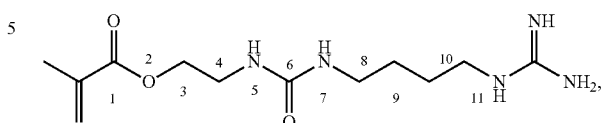

$N^2$-acryloyl-$N^1$-(4-{[amino(imino)methyl]amino}butyl)-2-methylalaninamide

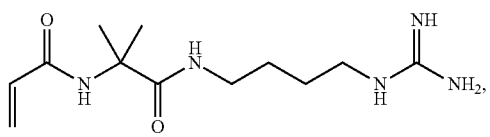 [SMILES: C=CC(=O)NC(C)(C)C(=O)NCCCCNC(=N)N]

$N^2$-acryloyl-$N^1$-(6-{[amino(imino)methyl]amino}hexyl)-2-methylalaninamide

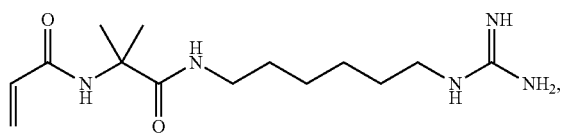 [SMILES: C=CC(=O)NC(C)(C)C(=O)NCCCCCCNC(=N)N]

and 2-({[N-(2-[amino(imino)methyl]aminoethyl)-N-benzylamino]carbonyl}-amino)ethyl methacrylate

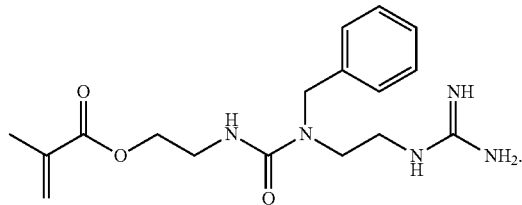 [SMILES: C=C(C)C(=O)OCCNC(=O)N(CCNC(=N)N)Cc1ccccc1]

The above-described first monomers can be homopolymerized to provide the polymeric chains. In other embodiments, various first monomers can be combined and copolymerized. In still other embodiments, other types of monomers can be combined with the first monomer and copolymerized.

In some embodiments, other monomers (second monomers) are copolymerized with the first monomers to adjust the binding capacity and/or to achieve other desired properties. Any suitable second monomer can be used. The second monomer can be, for example, a hydrophilic monomer to adjust the degree of hydrophilicity imparted to the substrate. The hydrophilic monomer has an ethylenically unsaturated group and a hydrophilic group such as, for example, a poly(oxyalkylene) group, hydroxyl group, or amido group. Suitable hydrophilic monomers include acrylamide, dimethylacrylamide, hydroxyethyl(meth)acrylate, hydroxypropyl(meth)acrylate, polyethylene glycol mono (meth)acrylate, 2-hydroxyethylacrylamide, N-vinylpyrrolidone, and the like, and combinations thereof.

Optionally, the first monomer can be copolymerized with a second monomer that has at least two ethylenically unsaturated groups. These monomers are often multifunctional (meth)acryloyl monomers (i.e., multifunctional (meth)acrylate monomers and (meth)acrylamide monomers). These types of second monomer are typically used in only relatively small amounts (for example, from 0.1 to 5 percent by weight, based upon the total weight of monomers) to impart a degree of branching and/or relatively light crosslinking to a resulting copolymer. Higher amounts can be used for certain applications, but higher amounts may reduce binding capacity for various biomaterials.

Useful multifunctional (meth)acryloyl monomers include di(meth)acrylates, tri(meth)acrylates, tetra(meth)acrylates, multifunctional (meth)acrylamides, and the like, and combinations thereof. Such multifunctional (meth)acryloyl monomers include ethyleneglycol di(meth)acrylate, glycerol di(meth)acrylate, 1,6-hexanediol di(meth)acrylate, poly(ethylene glycol) di(meth)acrylates, polybutadiene di(meth)acrylate, polyurethane di(meth)acrylates, propoxylated glycerin tri(meth)acrylate, methylenebisacrylamide, ethylenebisacrylamide, hexamethylenebisacrylamide, diacryloylpiperazine, and the like, and combinations thereof.

The plurality of grafted polymeric chains is usually terminated with thiocarbonylthio-containing groups. As such, the second article can be subjected to a second round of graft polymerization. In this method, the second article, which has polymeric chains terminated with thiocarbonylthio groups of formula —SC(=S)—R$^1$, is placed in contact with a second radically polymerizable monomer composition to form a second reaction mixture. This second radically polymerizable monomer composition may contain the same monomer(s) as in the first grafting reaction, or it may contain different monomer(s). Exposure to actinic radiation results in chain extension of the grafted polymeric chains since the thiocarbonylthio groups again can function as photoiniferters. When the monomer(s) in the second reaction mixture are different from those in the first reaction mixture, a block copolymer is formed that is grafted to the polymeric substrate.

In some second articles, at least some of the polymeric chains are terminated with thiocarbonylthio and/or thiol groups.

The second articles may be treated by processes, as are well known in the art, to remove the thiocarbonylthio group and/or to replace it with other chemical groups. In some embodiments, the thiocarbonylthio group is reacted to become a thiol group. Various processes are described, for example, in M. A. Harvison, et al., Aust. J. Chem., 64, 992-1006 (2011).

Advantageously, the polymeric chains can be varied in molecular weight depending on the amount of monomer present, the exposure time of the functionalized substrate to actinic radiation, and the concentration of groups of formula —S—C(=S)—R$^1$ on the functionalized substrate. It is believed that the molecular weight distribution of the polymeric chains is often narrower than with other known methods of grafting a plurality of polymeric chains to a polymeric substrate. In typical free radical polymerizations, the polymer formed has a relatively broad distribution of chain lengths due to conventional chain termination events and the overall kinetics of the polymerization reaction. Thus, it is anticipated that free radical grafting to solid substrates also will result in a distribution of graft chain lengths. On the other hand, controlled radical initiators have been shown to be effective at controlling polymer chain length, leading to a much narrower distribution of polymer molecular weight. Work by various investigators has shown that charge-clustered ligands are better than individual ligands for effective ion-exchange binding of proteins and that the binding affinity improves as the cluster number increases. While not wanting to be bound by theory, it is believed that it is highly likely that short grafted chains may be less effective at binding proteins than are longer chains. The thiocarbonylthio-containing groups attached to the solid substrate may, by virtue of their ability to act as iniferters, be providing control over the graft chain length, thus reducing the number of short grafted ligand chains. In effect, this tends to increase the average overall efficiencies of the grafted ligands.

Following polymerization, washing, and drying, typical total weight gains by the solid substrate generally can be in the range of 0.1 percent (%) to 30% (preferably, in the range of 0.5% to 10%). That is, this is the weight of the attached polymeric chains in the second article.

In certain embodiments, the final articles have 0.02 mmoles of monomer grafted per gram of the second article. This can be referred to as the "graft density" and is calculated by measuring the difference in weight between the solid substrate and the solid substrate having covalently attached polymeric chains (i.e., second article). This weight gain is divided by the theoretical molecular weight of the monomers used. It is expressed as millimoles of monomer per gram of the final article. In some embodiment, the amount of monomer grafted is at least 0.02 mmole/gram, at least 0.04 mmole/gram, at least 0.06 mmole/gram, at least 0.08 mmole/gram, or at least 0.10 mmoles/gram. In certain embodiments, the amount grafted is up to 1.0 mmole/gram, up to 0.8 mmole/gram, up to 0.6 mmole/gram, up to 0.5 mmole/gram, up to 0.4 mmole/gram, up to 0.35 mmole/gram, up to 0.3 mmole/gram, up to 0.25 mmoles/gram, or up to 0.2 mmole/gram.

The grafted polymeric chains can alter the properties of the original solid substrate. The second articles often can retain properties of the solid substrate (for example, mechanical and thermal stability, porosity, and so forth) but can also exhibit enhanced binding capacity for various biomaterials. The grafted polymeric chains advantageously do not clog the pores of the porous substrate. Articles containing a porous substrate with covalently attached polymeric chains (i.e., second articles) can be particularly useful as filter media for the purification of biological or other fluid samples comprising biologically derived species (biomaterials). The biomaterials can include, for example, viruses, proteins, bacteria, cells, cellular debris, endotoxins, various microorganisms, carbohydrates, and the like.

In some embodiments, the biomaterial being removed from the fluid is the object of the purification. For example, a recombinant protein or enzyme may be prepared in cell culture or by fermentation, and the substrate can be used to capture the protein or enzyme as the first step in the purification process. In another example, the substrate may be used to capture microorganisms from a fluid as the first step in a process of eliminating, concentrating, enumerating, and/or identifying the microorganisms.

In other embodiments, the biomaterial being removed from the fluid is a contaminant that must be removed prior to additional processing steps for the fluid. Contaminants may include viruses, host cell proteins, nucleic acids, endotoxins, media components, etc.

If desired, efficiency of binding and/or capture can be improved by using a plurality of stacked or layered, second articles having a porous substrate with covalently attached polymeric chains as a filter element. In many such filter elements, the porous substrate is a porous membrane. The individual layers of the filter element can be the same or different. The layers can vary in porosity, degree of grafting, and so forth. The filter element can further include an upstream pre-filter layer and/or a downstream support layer. The individual layers can be planar or pleated, as desired.

The filter element can be part of a filter cartridge, a filter assembly including one or more of the above-described filter elements and a filter housing, and the like. Any of these articles can further include conventional components such as housings, holders, adapters, and the like, and combinations thereof.

Examples of suitable pre-filter and support layer materials include any suitable porous membranes of polypropylene, polyester, polyamide, resin-bonded or binder-free fibers (for example, glass fibers), and other synthetics (woven and nonwoven fleece structures); sintered materials such as polyolefins, metals, and ceramics; yarns; special filter papers (for example, mixtures of fibers, cellulose, polyolefins, and binders); polymer membranes; and the like; and combinations thereof.

Target biomaterials may include proteins. A wide variety of biological solutions containing a protein may be utilized in the processes of the present disclosure. The solution, which contains a protein, may include, for example, fermentation broth or cell culture or murine ascites fluid. The protein can be any protein, or fragment thereof, known in the art. The protein may be derived from natural sources or from recombinant sources. The protein may have a native sequence or a non-natural sequence. In some embodiments, the protein is an enzyme. In some embodiments, the protein is a hormone. In some embodiments, the protein is an antibody. In a specific embodiment, the protein is a monoclonal antibody, or a fragment thereof. Fragments of antibodies include F(ab), F(ab'), F(ab')$_2$, Fv, and single-chain antibodies. In some cases, the protein may be a human monoclonal antibody. In other cases, the protein is an immunoglobulin G (IgG) antibody. In still other cases, the protein is a fusion protein such as an Fc-fusion protein.

In certain processes of the present disclosure, the target biomaterial includes aggregated proteins (in particular, antibodies). Thus, in another aspect of the disclosure, a process is provided that results in the separation of aggregated proteins (in particular, antibodies) from monomeric proteins (in particular, antibodies). The process involves allowing an initial biological solution that includes aggregated proteins (in particular, antibodies) (the target biomaterial) and monomeric proteins (in particular, antibodies), to contact the contacting surface (e.g., upstream or upper surface) of the filter element under conditions effective to separate the aggregated proteins from the monomeric proteins such that a final biological solution (i.e., the product obtained by contacting the initial biological solution with the filter element) includes purified monomeric proteins.

In certain embodiments of the process, allowing the biological solution to contact the contacting surface (e.g., upstream or upper surface) of the filter element occurs by passing the biological solution across the filter media or by allowing the biological solution to flow through the filter media, or both. In certain embodiments, allowing the biological solution to contact the contacting surface (e.g., upstream or upper surface) involves allowing the biological solution to flow through filter media.

In certain embodiments, the process involves purifying the biological fluid without the need for an eluting step. That is, this process does not bind the target proteins and wash through the impurities; rather, it is binding the impurities and allowing the target proteins to pass through. This is advantageous at least because it avoids dilution of the target proteins, which prevents the need to later concentrate the eluted proteins, thereby providing processing efficiency and decreasing processing time. This is also advantageous because it allows for the capture and disposal of impurities bound to the filter media, which is desirable when the filter media is enclosed within a disposable filter article. Furthermore, buffer exchanges and pH adjustments may be unnecessary.

The process involves allowing the biological solution to contact the contacting surface (e.g., upstream or upper surface) of the filter element under conditions effective to separate the impurities from the target proteins to provide the desired results.

In certain embodiments, such conditions include a pH of the biological solution of below 9, or below 8.5, or below 8, or below 7.5, or below 7, or below 6.5. In certain embodiments, such conditions include a pH of the biological solution of at least 4, or at least 4.5, or at least 5.

In certain embodiments, such conditions include a conductivity of the biological solution of at least 1 millisiemens per centimeter (mS/cm), or at least 2 mS/cm, or at least 3 mS/cm, or at least 4 mS/cm, or at least 5 mS/cm, or at least 6 mS/cm, or at least 7 mS/cm, or at least 8 mS/cm, or at least 9 mS/cm, or at least 10 mS/cm. In certain embodiments, such conditions include a conductivity of the biological solution of no greater than 110 mS/cm, or no greater than 100 mS/cm, or no greater than 50 mS/cm, or no greater than 40 mS/cm, or no greater than 30 mS/cm.

In certain aspects of the disclosure, a process for capture or removal of a target biomaterial is provided that uses articles of the present disclosure that include filter elements having a contacting surface (e.g., an upstream or upper surface). Such articles can be in the form of an array of sample containers (e.g., a 96-well plate) with each container including a filter element having a contacting surface (e.g., an upstream or upper surface). The process includes: providing a filter element or an array of sample containers of the present disclosure; and allowing a biological solution including a target biomaterial to contact the contacting surface (e.g., upstream or upper surface) of the filter element under conditions effective for binding of the target biomaterial.

In certain embodiments, assessment of optimal conditions for the process is conveniently conducted using an array of sample containers, wherein each container includes filter elements of the present disclosure. A particularly useful array of containers is, for example, a 96-well filter plate in which each well includes filter elements of the disclosure. Each well of an individual plate may include the same filter element, that is, the filter elements may be functionalized with the same polymer or copolymer composition. Alternatively, two or more different filter elements, i.e., functionalized with different polymer compositions, may be disposed within the wells of a single plate. Each well may include a single layer of a filter element, or alternatively may contain more than one layer of filter elements. In the latter case, the multiple layers of filter elements may be functionalized with the same polymer, or with different polymers. Protein solutions may then be prepared utilizing a variety of buffer salts, buffer pH values, buffer conductivities, and/or protein concentrations. These initial solutions may then be applied into the wells of the plate so as to contact the contacting surface (e.g., upstream or upper surface) of the filter elements. Following a predetermined contact time, the protein solution may be passed through the filter elements, such as by centrifugation or by vacuum filtration, and may be collected in the wells of a collection plate. The filtrate (final solution) thus collected may be analyzed for concentration of monomeric protein and aggregated protein, such as by HPLC analysis, and compared with that of the initial solution. In this manner, optimal conditions (in terms of buffer, pH, conductivity, etc.) for removal of aggregated protein with minimal loss of monomeric protein can be assessed within the context of a single, high throughput experiment. Such techniques are well known to one of skill in the art.

Various articles and methods of making the articles are provided.

Embodiment 1A is a method of making an article having a solid polymeric substrate with covalently attached polymeric chains. The method includes providing a solid polymeric substrate and generating free radicals on a surface of the solid polymeric substrate to form a treated substrate. The method further includes reacting the free radicals of the treated substrate with a fluid comprising a thiocarbonylthio-containing compound to covalently bond a plurality of thiocarbonylthio-containing groups directly and covalently to the solid polymeric substrate and forming a functionalized substrate. The method still further includes preparing a reaction mixture by contacting the functionalized substrate with a radically polymerizable monomer composition comprising a first monomer having (a) at least one ethylenically unsaturated group, (b) at least one ligand functional group that is an acidic group, basic group, or salt thereof, and (c) a spacer group that directly links the at least one ethylenically unsaturated group and the at least one the ligand functional group by a chain of at least six catenated atoms. The method yet further includes exposing the reaction mixture to actinic radiation and forming a polymeric chain directly and covalently attached to a carbon atom in a polymeric backbone of the solid polymeric substrate, the polymeric chains being a polymerized product of the radically polymerizable monomer composition.

Embodiment 2A is the method of embodiment 1A, wherein at least some of the polymeric chains are terminated with a thiol group or a thiocarbonylthio-containing group.

Embodiment 3A is the method of embodiment 1A or 2A, wherein generating free radicals on the surface of the solid polymeric substrate comprises applying a coating layer comprising a type II photoinitiator to the surface of the solid polymeric substrate and irradiating the coating layer with ultraviolet radiation to abstract hydrogen atoms from the solid polymeric substrate to form the treated substrate.

Embodiment 4A is the method of embodiment 1A or 2A, wherein the thiocarbonylthio-containing compound is present when generating free radicals on the surface of the solid polymeric substrate.

Embodiment 5A is the method of embodiment 1A or 2A, wherein generating free radicals on the surface of the solid polymeric substrate to form the treated substrate comprises exposing the solid polymeric substrate to electron beam radiation, gamma radiation, or to a plasma in an inert environment.

Embodiment 6A is the method of embodiment 5A, wherein the thiocarbonylthio-containing compound is absent when generating free radicals on the surface of the solid polymeric substrate.

Embodiment 7A is the method of embodiment 1A or 2A, wherein the solid polymeric substrate is photoactive and wherein generating free radicals occurs upon exposure to actinic radiation.

Embodiment 8A is the method of embodiment 7A, wherein the solid substrate is a poly(ether sulfone).

Embodiment 9A is the method of any one of embodiments 1A to 8A, wherein the thiocarbonylthio-containing group contains at least one thiocarbonylthio-containing group of formula —S—C(=S)—$R^1$ where $R^1$ is an alkoxy, aralkyloxy, alkenyloxy, or —N($R^4$)$_2$ where each $R^4$ is an alkyl or where two adjacent $R^4$ groups are combined with the nitrogen to which they are both attached to form a first heterocyclic ring having 1 to 3 heteroatoms selected from nitrogen, oxygen, and sulfur and 2 to 5 carbon atoms, the first heterocyclic ring being saturated or unsaturated (e.g., partially or fully unsaturated) and optionally fused to one or more second rings that are carbocyclic or heterocyclic.

Embodiment 10A is the method of embodiment 9A, wherein $R^1$ is an alkoxy.

Embodiment 11A is the method of embodiment 9A, wherein $R^1$ is of formula —N($R^4$)$_2$ and each $R^4$ is an alkyl.

Embodiment 12A is the method of any one of embodiments 1A to 11A, wherein the solid polymeric substrate is porous.

Embodiment 13A is the method of embodiment 12A, wherein the solid polymeric substrate is a porous membrane.

Embodiment 14A is the method of embodiment 12A, wherein the solid polymeric substrate is a porous non-woven substrate.

Embodiment 15A is the method of any one of embodiments 1A to 14A, wherein the first monomer is of Formula (IV).

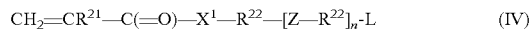

Group $R^{21}$ is selected from hydrogen, alkyl, cycloalkyl, aryl, and combinations thereof. Group $R^{22}$ is a (hetero)hydrocarbylene. Group $X^1$ is —O— or —NR$^{23}$— where $R^{23}$ is selected from hydrogen or hydrocarbyl. Z is heterohydrocarbylene including at least one hydrogen bond donor, at least one hydrogen bond acceptor, or a combination thereof. The variable n is an integer of 0 or 1 and L is a ligand functional group comprising an acidic group, a basic group, or salt thereof.

Embodiment 16A is the method of embodiment 15A, wherein n is equal to 1, Z is —C(=O)—$X^2$—where $X^2$ is oxy or —NR$^{23}$—, and the first monomer of Formula (IV) is of Formula (IV-1).

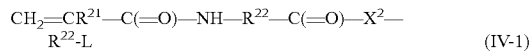

Embodiment 17A is the method of embodiment 15A, wherein n is equal to 1, Z is —NH—C(=O)—$X^2$— where $X^2$ is oxy or —NR$^{23}$—, and the first monomer of Formula (IV) is of Formula (IV-2).

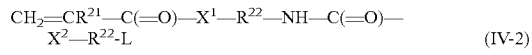

Embodiment 18A is the method of embodiment 15A, wherein n is equal to 1, Z is —C(=O)—NR$^{23}$—, $X^1$ is —NR$^{23}$—, L is of formula —NR$^{24}$—[C(=NR$^{24}$)—NR$^{24}$]$_m$R$^{25}$ where m is 1 or 2, $R^{24}$ is hydrogen or hydrocarbyl, $R^{25}$ is hydrogen, hydrocarbyl, or —N($R^{24}$)$_2$, and the first monomer is of Formula (IV-3).

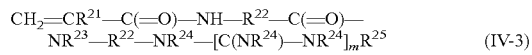

Embodiment 19A is the method of embodiment 15A, wherein n is equal to 1, Z is —NH—C(=O)—NR$^{23}$—, L is of formula —NR$^{24}$—[C(=NR$^{24}$)—NR$^{24}$]$_m$R$^{25}$ where m is 1 or 2, R$^{24}$ is hydrogen or hydrocarbyl, R$^{25}$ is hydrogen, hydrocarbyl, or —N(R$^{24}$)$_2$, and the first monomer of Formula (IV) is of Formula (IV-4).

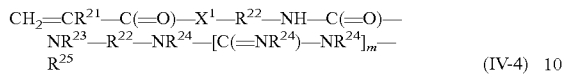

$$CH_2=CR^{21}-C(=O)-X^1-R^{22}-NH-C(=O)-NR^{23}-R^{22}-NR^{24}-[C(=NR^{24})-NR^{24}]_m-R^{25} \quad (IV\text{-}4)$$

Embodiment 20A is the method of embodiment 15A, wherein Z is a hydrogen bonding moiety selected from carbonylimino, thiocarbonylimino, iminocarbonylimino, iminothiocarbonylimino, oxycarbonylimino, oxythiocarbonylimino, and the like, and combinations thereof. In certain embodiments, hydrogen bonding moieties include carbonylimino, iminocarbonylimino, oxycarbonylimino, and combinations thereof.

Embodiment 1B is an article that includes a) a solid polymeric substrate and b) polymeric chains attached directly and covalently to carbon atoms in a polymeric backbone of the solid polymeric substrate. The polymeric chains comprise a polymerized product of a radically polymerizable monomer composition comprising a first monomer having (a) at least one ethylenically unsaturated group, (b) at least one ligand functional group selected from acidic groups, basic groups, and salts thereof, and (c) a spacer group that directly links the at least one ethylenically unsaturated group and the at least one ligand functional group by a chain of at least six catenated atoms. At least some of the polymeric chains are terminated by a thiol or a thiocarbonylthio-containing group.

Embodiment 2B is the article of embodiment 1B, wherein the thiocarbonylthio-containing group is of formula —S—C(=S)—R$^1$ wherein group R$^1$ in the thiocarbonylthio-containing group is typically selected to be an alkoxy, aralkyloxy, alkenyloxy or —N(R$^4$)$_2$; and each R$^4$ is an alkyl or two adjacent R$^4$ groups are combined with the nitrogen to which they are both attached to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic.

Embodiment 3B is the article of embodiment 1B or 2B, wherein the first monomer is of Formula (IV).

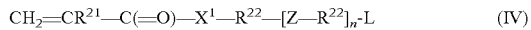

$$CH_2=CR^{21}-C(=O)-X^1-R^{22}-[Z-R^{22}]_n-L \quad (IV)$$

Group R$^{21}$ is selected from hydrogen, alkyl, cycloalkyl, aryl, and combinations thereof. Group R$^{22}$ is a (hetero)hydrocarbylene. Group X$^1$ is —O— or —NR$^{23}$— where R$^{23}$ is from hydrogen or hydrocarbyl. Z is heterohydrocarbylene including at least one hydrogen bond donor, at least one hydrogen bond acceptor, or a combination thereof. The variable n is an integer of 0 or 1 and L is a ligand functional group comprising an acidic group, a basic group, or salt thereof.

Embodiment 4B is the article of embodiment 3B, wherein n is equal to 1, Z is —C(=O)—X$^2$— where X$^2$ is oxy or —NR$^{23}$—, and the first monomer of Formula (IV) is of Formula (IV-1).

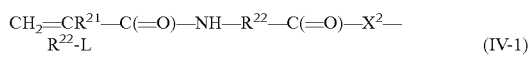

$$CH_2=CR^{21}-C(=O)-NH-R^{22}-C(=O)-X^2-R^{22}-L \quad (IV\text{-}1)$$

Embodiment 5B is the article of embodiment 3B, wherein n is equal to 1, Z is —NH—C(=O)—X$^2$— where X$^2$ is oxy or —NR$^{23}$—, and the first monomer of Formula (IV) is of Formula (IV-2).

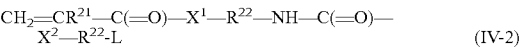

$$CH_2=CR^{21}-C(=O)-X^1-R^{22}-NH-C(=O)-X^2-R^{22}-L \quad (IV\text{-}2)$$

Embodiment 6B is the article of embodiment 3B, wherein n is equal to 1, Z is —C(=O)—NR$^{23}$—, X$^1$ is —NR$^{23}$—, L is of formula —NR$^{24}$—[C(=NR$^{24}$)—NR$^{24}$]$_m$R$^{25}$ where m is 1 or 2, R$^{24}$ is hydrogen or hydrocarbyl, R$^{25}$ is hydrogen, hydrocarbyl, or —N(R$^{24}$)$_2$, and the first monomer is of Formula (IV-3).

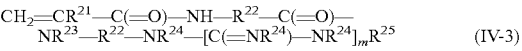

$$CH_2=CR^{21}-C(=O)-NH-R^{22}-C(=O)-NR^{23}-R^{22}-NR^{24}-[C(=NR^{24})-NR^{24}]_mR^{25} \quad (IV\text{-}3)$$

Embodiment 7B is the article of embodiment 3B, wherein n is equal to 1, Z is —NH—C(=O)—NR$^{23}$—, L is of formula —NR$^{24}$—[C(=NR$^{24}$)—NR$^{24}$]$_m$R$^{25}$ where m is 1 or 2, R$^{24}$ is hydrogen or hydrocarbyl, R$^{25}$ is hydrogen, hydrocarbyl, or —N(R$^{24}$)$_2$, and the first monomer of Formula (IV) is of Formula (IV-4).

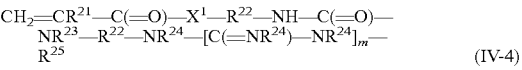

$$CH_2=CR^{21}-C(=O)-X^1-R^{22}-NH-C(=O)-NR^{23}-R^{22}-NR^{24}-[C(=NR^{24})-NR^{24}]_m-R^{25} \quad (IV\text{-}4)$$

Embodiment 8B is the article of embodiment 3B, wherein Z is a hydrogen bonding moiety selected from carbonylimino, thiocarbonylimino, iminocarbonylimino, iminothiocarbonylimino, oxycarbonylimino, oxythiocarbonylimino, and the like, and combinations thereof. In certain embodiments, hydrogen bonding moieties include carbonylimino, iminocarbonylimino, oxycarbonylimino, and combinations thereof.

Embodiment 9B is the article of any one of embodiments 1B to 8B, wherein the solid polymeric substrate is porous.

Embodiment 10B is the article of embodiment 9B, wherein the solid polymeric substrate is a porous membrane.

Embodiment 11B is the article of embodiment 9B, wherein the solid polymeric substrate is a non-woven substrate.

EXAMPLES $^1$H NMR Analysis

Proton nuclear magnetic resonance ($^1$H NMR) analysis was carried out using a BRUKER A500 NMR spectrometer (Bruker Corporation, Billerica, MA).

Combustion Ion Chromatography Analysis

Samples of the functionalized substrates (from Preparative Examples 1-27) were individually analyzed for sulfur content by combustion ion chromatography using an AQF-100 furnace (Mitsubishi Chemical Corporation, Tokyo, Japan) and an ICS-2000 ion chromatography system (Dionex Corporation, Sunnyvale, CA). Each sample was decomposed in the furnace and the carrier gases were bubbled through an absorber solution. The absorber solution was analyzed by ion chromatography for sulfate ion.

The instrument was calibrated by analyzing varied volumes of stock solutions containing known amounts of sulfur. A calibration curve was then created by plotting the peak area consistent with sulfate against the mass of the component in the calibration standard. Three samples from each functionalized substrate were placed into separate ceramic sample boats and analyzed in the same manner as the standards. The mean value (n=3) for sulfur content was reported as ppm of sulfur (μg S/g of sample). Based on the sulfur content measured for the sample, the concentration of the corresponding thiocarbonylthio containing groups in the sample was calculated by dividing the measured ppm of sulfur (μg S/g of sample) by 64 (the number of μg of S in one µmole of thiocarbonylthio group). The result was reported in micromoles of thiocarbonylthio groups per gram of sample (µmol/g). The results are reported in Tables 1-6.

X—Ray Fluorescence (XRF) Analysis

Three samples were cut from each functionalized substrate of Preparative Examples 32-36. Each sample was individually placed into a stainless steel XRF sample holder and secured into position using double coated tape and a hollow aluminum scatter elimination cup. Each sample was subsequently analyzed for sulfur using a Primus II wavelength dispersive X-ray fluorescence spectrometer (Rigaku Corporation, Tokyo, Japan) equipped with a rhodium X-ray source, a vacuum atmosphere, and a 20 mm diameter measurement area. The scan conditions used for sulfur (S) detection are listed in the Table A below.

TABLE A

| Element | Analytical Line | Angular Range | Step Size | Count Time | X-ray Tube Voltage/Current | Crystal | Detector |
|---|---|---|---|---|---|---|---|
| Sulfur (S) | K-α | 107.02-114.02° 2Θ | 0.05° | 1.0 sec | 30/100 kV/mA | Ge | Flow Proportional Counter |

Each sample of the functionalized substrate was analyzed in triplicate. The mean value for sulfur content (n=9) was reported as ppm of sulfur (µs S/g of sample). Based on the sulfur content measured for the sample, the concentration of the corresponding thiocarbonylthio containing groups in the sample was calculated by dividing the measured ppm of sulfur (µg S/g of sample) by 64 (the number of µs of S in one mole of thiocarbonylthio group). The result was reported in micromoles of thiocarbonylthio groups per gram of sample (mol/g). The results are reported in Tables 7-8.

Static IgG Capacity Method

Grafted substrates of the Examples were analyzed for static binding capacity by incubating a disk of the grafted substrate in a solution of test analyte overnight. The disk was prepared by die-punching an 18 mm diameter disk from a sheet of the substrate. Each disk was placed in a 5 mL centrifuge tube with 4.5 mL of human IgG (Sigma-Aldrich Corporation, St. Louis, MO) challenge solution at a concentration of about 3.5 mg/mL in 50 mM HEPES buffer at pH 7.0. The tubes were capped and tumbled overnight (typically 14 hours) on a rotating mixer (Barnstead/Thermolyne LABQUAKE Tube Shaker, obtained from VWR International, Radnor, PA). The supernatant solutions were analyzed using a UV-VIS spectrometer (Agilent 8453, Agilent Technologies, Santa Clara, CA) at 280 nm (with background correction applied at 325 nm). The static binding capacity for each substrate was determined by comparison to the absorbance of the starting IgG solution and the results are reported in mg/mL (mg of protein bound per mL of substrate volume) as the average of three replicates.

Synthesis of methyl 2-ethoxycarbothioylsulfanylacetate

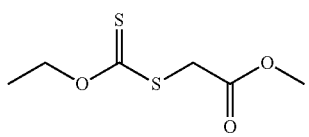

A stirred solution of methyl chloroacetate (10.85 g, available from Alfa Aesar, Haverhill, Massachusetts) in acetone (100 mL) was chilled in a water/ice bath. Potassium ethyl xanthate (16.0 g, available from Alfa Aesar) was added to the solution followed by an additional 50 mL of acetone. The reaction mixture was stirred for two hours and then filtered through a bed of Celite. The resulting pale yellow solution was concentrated under reduced pressure to provide 17.68 g of methyl 2-ethoxycarbothioylsulfanylacetate as a pale yellow liquid. $^1$H-NMR (CDCl$_3$): δ 1.35 (t, 3H), 3.69 (s, 3H), 3.86 (s, 2H), 4.57 (q, 2H).

Synthesis of Dixanthogen

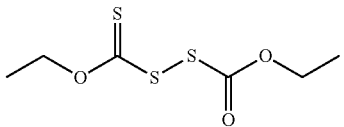

A solution of sodium peroxydisulfate [8.00 g (available from Alfa Aesar) in 50 mL of deionized water] was added dropwise over a 15 minute period to a stirred solution of potassium ethyl xanthate [10.86 g (available from Alfa Aesar) in 50 mL of deionized water]. When about half of the sodium peroxydisulfate was added, the reaction flask was warm to the touch. At this point the reaction flask was placed in a cold water bath and maintained in the bath for the remainder of the addition. The bath was removed and the resulting reaction product was extracted with diethyl ether. The diethyl ether fraction was dried with anhydrous sodium sulfate, filtered, and concentrated under reduced pressure to provide 7.63 g of dixanthogen as a yellow oil. $^1$H-NMR (CDCl$_3$): δ 1.40 (t, 3H), 4.67 (q, 2H).

Synthesis of O-ethyl-(2-amino-2-oxo-ethyl)sulfanylmethanethioate

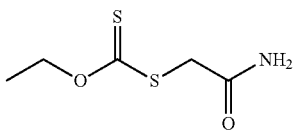

A stirred solution of bromoacetamide (10.85 g, available from Sigma-Aldrich Corporation, St. Louis, MO) in acetone (100 mL) was chilled in a water/ice bath. Potassium ethyl xanthate (16.0 g, Alfa Aesar) was added as a solid and after 15 minutes an additional 50 mL of acetone was added to the reaction. The reaction was stirred for a total of 1.25 hours total and then filtered through a bed of Celite. The resulting yellow solution was concentrated under reduced pressure to yield a colorless solid. The solid was dried in a vacuum oven overnight at ambient temperature to provide 14.02 g of O-ethyl-(2-amino-2-oxo-ethyl)sulfanylmethanethioate. $^1$H-NMR (acetone-d$\delta$): δ 1.39 (t, 3H), 3.91 (s, 2H), 4.63 (q, 2H), 6.6 (broad s, 1H), 7.1 (broad s, 1H).

Synthesis of (isopropoxycarbothioylsulfanyl)methyl octyl ether

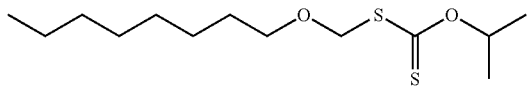 [SMILES: CCCCCCCCOCSC(=S)OC(C)C]

Isopropanol (871.1 g), in a flask equipped with a mechanical stirrer, was purged with nitrogen. Sodium metal cubes (20.25 g, Sigma-Aldrich Corporation) were cut into small pieces and added to the flask over a period of three hours. The temperature was then increased to 65° C. The sodium dissolved with evolution of hydrogen over three additional hours resulting in a clear solution. The mixture was then cooled to 35° C. using an ice bath, to provide a thick slurry. Carbon disulfide (73.80 g) was added slowly over 30 minutes to the slurry followed by stirring for an additional 30 minutes to give a yellow solution. Solvent removal under vacuum gave a yellow solid which was further dried under high vacuum (1 mm Hg) for four hours to provide 136.7 g of sodium isopropyl xanthate as a yellow powder.

A mixture of sodium isopropyl xanthate (3.90 g) and acetone (50 mL) was cooled in an ice bath. A solution of chloromethyl octyl ether (4.00 g, TCI America) was added slowly over 15 minutes. After stirring at room temperature for three hours, the solvent was removed under vacuum. Ethyl acetate (30 mL) was added and the mixture was washed with water two times. The organic phase was concentrated under vacuum and the residual oil was purified by column chromatography ($SiO_2$, 1 to 10% ethyl acetate in hexanes) to provide 5.42 g of (isopropoxycarbothioylsulfanyl)methyl octyl ether as a yellow oil. $^1$H-NMR: δ 5.75-5.82 (m, 1H), 5.27 (s, 2H), 3.51 (t, J=6.6 Hz, 2H), 1.53-1.59 (m, 2H), 1.39 (d, J=6.3, 6H), 1.20-1.35 (m, 10H), 0.86 (t, J=7.1 Hz, 3H).

Synthesis of 4-[[2-methyl-2-(prop-2-enoylamino)propanoyl]amino]butanoic acid, sodium salt (VDM-GABA)

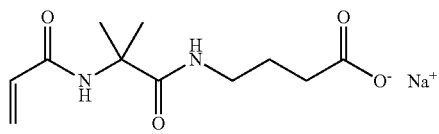 [SMILES: C=CC(=O)NC(C)(C)C(=O)NCCCC(=O)[O-] ; [Na+]]

4-Aminobutanoic acid (GABA) (5.15 g, 0.05 mol) was added to a 100 mL round bottom flask. An aqueous solution of sodium hydroxide (1.0 N, 50 mL) was added to the flask and the resulting mixture was stirred until the solids dissolved. The flask was then placed in an ice-water bath and stirred for 15 minutes. 2-Vinyl-4,4-dimethylazlactone (VDM) (6.95 g, 0.05 mol, obtained from SNPE, Inc, Princeton, NJ) was added by syringe and the reaction was stirred for 30 minutes with the flask continuously maintained in the ice-water bath. The cooling bath was then removed and the reaction was allowed to warm to room temperature over a period of 30 minutes. $^1$H-NMR of an aliquot confirmed complete conversion to 4-[[2-methyl-2-(prop-2-enoylamino)propanoyl]amino]butanoic acid, sodium salt. The pH of the reaction was adjusted to about 7 by the addition of a few drops of a concentrated hydrochloric acid solution. $^1$H-NMR ($D_2O$) δ 1.34 (s, 6H), 1.59 (p, 2H), 2.04 (t, 2H), 3.05 (t, 2H), 5.62 (d, 1H), 6.0-6.2 (m, 2H).

Preparative Example 1

An 18 cm×23 cm section of nylon membrane substrate (nylon 6,6 membrane, single reinforced layer nylon three zone membrane, nominal pore size 1.8 micron, 0.165 mm thick, bulk density 0.415 g/cm$^3$, #080ZN from 3M Purification, Inc., Meriden, CT) was placed on a sheet of clear polyester film (10 mil thick). A first coating solution of benzophenone (0.5 weight percent) in acetone was prepared and approximately 10-15 mL of the coating solution was pipetted onto the top surface of the substrate. The first coating solution was allowed to soak into the substrate and then a second sheet of the polyester film was placed on top of the substrate. Excess first coating solution was removed by rolling a 2.28 kg cylindrical weight over the top of the three-layer sandwich. Ultraviolet (UV) light-initiated treatment was conducted by irradiating the sandwich using a stand (Classic Manufacturing, Inc., Oakdale, MN) equipped with 18 bulbs (Sylvania RG2 40W F40/350BL/ECO, 10 bulbs positioned above and 8 bulbs positioned below the substrate, with each bulb 1.17 meters (46 inches) long and spaced 5.1 cm (2 inches) on center). The substrate was placed on a glass plate positioned in the stand with a bulb to substrate distance of 3.5 cm. The irradiation time was 15 minutes. Following irradiation, the polyester sheets were removed and the resulting treated substrate was placed in a 1000 mL polyethylene bottle. The bottle was filled with acetone, sealed, and shaken for 30 minutes to wash off any residual benzophenone. The wash solution was decanted. The wash procedure was repeated two more times and then the substrate was air dried. The resulting treated substrate was cut into a 9 cm×11.5 cm section and placed on a sheet of clear polyester film.

A second coating solution of methyl 2-ethoxycarbothioylsulfanylacetate (2.6 weight percent) in acetone was prepared and 2.5 mL of the second coating solution was pipetted onto the top surface of the treated substrate. The second coating solution was allowed to soak into the treated substrate and then a second sheet of the polyester film was placed on top of the substrate. Excess second coating solution was removed by rolling a 2.28 kg cylindrical weight over the top of the three-layer sandwich. The sandwich was irradiated in the stand described above for 30 minutes. Following irradiation, the polyester sheets were removed. The resulting substrate functionalized with covalently attached thiocarbonylthio containing groups (—S—C(S)OCH$_2$CH$_3$) was placed in a 250 mL polyethylene bottle for washing. The bottle was filled with acetone, sealed, and shaken for 30 minutes. The wash solution was decanted. The wash procedure was repeated two more times and then the functionalized substrate was air dried. A sample of the functionalized substrate was analyzed by combustion ion chromatography and the result is reported in Table 1.

Preparative Example 2

The same procedure as described in Preparative Example 1 was followed with the exception that the treated substrate coated with the second coating solution was irradiated for 15 minutes, instead of 30 minutes. A sample of the functionalized substrate was analyzed by combustion ion chromatography and the result is reported in Table 1.

Preparative Example 3

The same procedure as described in Preparative Example 1 was followed with the exception that the treated substrate coated with the second coating solution was irradiated for 10 minutes, instead of 30 minutes. A sample of the functionalized substrate was analyzed by combustion ion chromatography and the result is reported in Table 1.

Preparative Example 4

The same procedure as described in Preparative Example 1 was followed with the exception that the treated substrate coated with the second coating solution was irradiated for 5 minutes, instead of 30 minutes. A sample of the functionalized substrate was analyzed by combustion ion chromatography and the result is reported in Table 1.

TABLE 1

Effect of Varying Irradiation Time of $2^{nd}$ Coating on the Reaction Product (Preparative Examples 1-4)

| Preparative Example Number | Irradiation Time for 2nd Coating Solution (minutes) | Conc. of —S—C(S)OCH$_2$CH$_3$ Groups in the Analytical Sample (µmol/gram) |
| --- | --- | --- |
| 1 | 30 | 6.8 |
| 2 | 15 | 4.7 |
| 3 | 10 | 5.1 |
| 4 | 5 | 4.2 |

Preparative Example 5

An 18 cm×23 cm section of nylon membrane substrate (nylon 6,6 membrane, single reinforced layer nylon three zone membrane, nominal pore size 1.8 micron, 0.165 mm thick, bulk density 0.415 g/cm$^3$, #080ZN from 3M Purification, Inc., Meriden, CT) was placed on a sheet of clear polyester film (10 mil thick). A first coating solution of benzophenone (0.5 weight percent) in acetone was prepared and approximately 10-15 mL of the coating solution was pipetted onto the top surface of the substrate. The first coating solution was allowed to soak into the substrate and then a second sheet of the polyester film was placed on top of the substrate. Excess first coating solution was removed by rolling a 2.28 kg cylindrical weight over the top of the three-layer sandwich. Ultraviolet (UV) light-initiated treatment was conducted by irradiating the sandwich using a stand (Classic Manufacturing, Inc.) equipped with 18 bulbs (Sylvania RG2 40W F40/350BL/ECO, 10 bulbs positioned above and 8 bulbs positioned below the substrate, with each bulb 1.17 meters (46 inches) long and spaced 5.1 cm (2 inches) on center). The substrate was placed on a glass plate positioned in the stand with a bulb to substrate distance of 3.5 cm. The irradiation time was 15 minutes. Following irradiation, the polyester sheets were removed and the resulting treated substrate was placed in a 1000 mL polyethylene bottle. The bottle was filled with acetone, sealed, and shaken for 30 minutes to wash off any residual benzophenone. The wash solution was decanted. The wash procedure was repeated two more times and then the substrate was air dried.

The resulting treated substrate was cut into a 9 cm×11.5 cm section and placed on a sheet of clear polyester film. A second coating solution of dixanthogen (3.1 weight percent) in acetone was prepared and 2.5 mL of the second coating solution was pipetted onto the top surface of the treated substrate. The second coating solution was allowed to soak into the treated substrate and then a second sheet of the polyester film was placed on top of the substrate. Excess second coating solution was removed by rolling a 2.28 kg cylindrical weight over the top of the three-layer sandwich. The sandwich was irradiated in the stand described above for 30 minutes. Following irradiation, the polyester sheets were removed. The resulting substrate functionalized with covalently attached thiocarbonylthio containing groups (—S—C(S)OCH$_2$CH$_3$) was placed in a 250 mL polyethylene bottle for washing. The bottle was filled with acetone, sealed, and shaken for 30 minutes. The wash solution was decanted. The wash procedure was repeated two more times and then the functionalized substrate was air dried. A sample of the functionalized substrate was analyzed by combustion ion chromatography and the result is reported in Table 2.

Preparative Example 6

The same procedure as described in Preparative Example 5 was followed with the exception that the treated substrate coated with the second coating solution was irradiated for 15 minutes, instead of 30 minutes. A sample of the functionalized substrate was analyzed by combustion ion chromatography and the result is reported in Table 2.

Preparative Example 7

The same procedure as described in Preparative Example 5 was followed with the exception that the treated substrate coated with the second coating solution was irradiated for 10 minutes, instead of 30 minutes. A sample of the functionalized substrate was analyzed by combustion ion chromatography and the result is reported in Table 2.

Preparative Example 8

The same procedure as described in Preparative Example 5 was followed with the exception that the treated substrate coated with the second coating solution was irradiated for 5 minutes, instead of 30 minutes. A sample of the functionalized substrate was analyzed by combustion ion chromatography and the result is reported in Table 2.

TABLE 2

Effect of Varying Irradiation Time of $2^{nd}$ Coating on the Reaction Product (Preparative Examples 5-8)

| Preparative Example Number | Irradiation Time for 2nd Coating Solution (minutes) | Conc. of —S—C(S)OCH$_2$CH$_3$ Groups in the Analytical Sample (µmol/gram) |
| --- | --- | --- |
| 5 | 30 | 9.5 |
| 6 | 15 | 8.1 |
| 7 | 10 | 8.1 |
| 8 | 5 | 7.1 |

Preparative Example 9

An 18 cm×23 cm section of nylon membrane substrate (nylon 6,6 membrane, single reinforced layer nylon three zone membrane, nominal pore size 1.8 micron, 0.165 mm thick, bulk density 0.415 g/cm$^3$, #080ZN from 3M Purification, Inc.) was placed on a sheet of clear polyester film (10 mil thick). A first coating solution of benzophenone (1.0 weight percent) in acetone was prepared and approximately 10-15 mL of the coating solution was pipetted onto the top surface of the substrate. The first coating solution was allowed to soak into the substrate and then a second sheet of the polyester film was placed on top of the substrate. Excess first coating solution was removed by rolling a 2.28 kg cylindrical weight over the top of the three-layer sandwich. Ultraviolet (UV) light-initiated treatment was conducted by irradiating the sandwich using a stand (Classic Manufacturing, Inc.) equipped with 18 bulbs (Sylvania RG2 40W F40/350BL/ECO, 10 bulbs positioned above and 8 bulbs positioned below the substrate, with each bulb 1.17 meters (46 inches) long and spaced 5.1 cm (2 inches) on center). The substrate was placed on a glass plate positioned in the stand with a bulb to substrate distance of 3.5 cm. The irradiation time was 15 minutes. Following irradiation, the polyester sheets were removed and the resulting treated substrate was placed in a 1000 mL polyethylene bottle for washing. The bottle was filled with acetone, sealed, and shaken for 30 minutes to wash off any residual benzophenone. The wash solution was decanted. The wash procedure was repeated two more times and then the substrate was air dried.

The resulting treated substrate was cut into a 9 cm×11.5 cm section and placed on a sheet of clear polyester film. A second coating solution of tetraethylthiuram disulfide (available from Sigma-Aldrich Corporation, 4.0 weight percent) in acetone was prepared and 2.5 mL of the second coating solution was pipetted onto the top surface of the treated substrate. The second coating solution was allowed to soak into the treated substrate and then a second sheet of the polyester film was placed on top of the substrate. Excess second coating solution was removed by rolling a 2.28 kg cylindrical weight over the top of the three-layer sandwich. The sandwich was irradiated in the stand described above for 30 minutes. Following irradiation, the polyester sheets were removed. The resulting substrate functionalized with covalently attached thiocarbonylthio containing groups (—S—C(S)N(CH$_2$CH$_3$)$_2$) was placed in a 250 mL polyethylene bottle for washing. The bottle was filled with acetone, sealed, and shaken for 30 minutes. The wash solution was decanted. The wash procedure was repeated two more times and then the functionalized substrate was air dried. A sample of the functionalized substrate was analyzed by combustion ion chromatography and the result is reported in Table 3.

Preparative Example 10

The same procedure as described in Preparative Example 9 was followed with the exception that the first coating solution was benzophenone (2.5 weight percent) in acetone, instead of 1.0 weight percent. A sample of the functionalized substrate was analyzed by combustion ion chromatography and the result is reported in Table 3.

Preparative Example 11

The same procedure as described in Preparative Example 9 was followed with the exception that the first coating solution was benzophenone (5.0 weight percent) in acetone, instead of 1.0 weight percent. A sample of the functionalized substrate was analyzed by combustion ion chromatography and the result is reported in Table 3.

Preparative Example 12

The same procedure as described in Preparative Example 9 was followed with the exception that the first coating solution was benzophenone (10.0 weight percent) in acetone, instead of 1.0 weight percent. A sample of the functionalized substrate was analyzed by combustion ion chromatography and the result is reported in Table 3.

TABLE 3

Effect of Varying Benzophenone Concentration on the Reaction Product (Preparative Examples 9-12)

| Preparative Example Number | Conc. of Benzophenone in 1st Coating Solution (weight %) | Conc. of —S—C(S)N(CH$_2$CH$_3$)$_2$ Groups in the Analytical Sample (μmol/gram) |
|---|---|---|
| 9 | 1.0 | 6.1 |
| 10 | 2.5 | 8.7 |
| 11 | 5.0 | 8.1 |
| 12 | 10.0 | 9.2 |

Preparative Example 13

A 9 cm×11.5 cm section of nylon membrane substrate (nylon 6,6 membrane, single reinforced layer nylon three zone membrane, nominal pore size 1.8 micron, 0.165 mm thick, bulk density 0.415 g/cm$^3$, #080ZN from 3M Purification, Inc.) was placed on a sheet of clear polyester film (10 mil thick). A coating solution containing benzophenone (0.5 weight percent) and methyl 2-ethoxycarbothioylsulfanylacetate (2.6 weight percent) in acetone was prepared. Approximately 2.5-3 mL of the coating solution was pipetted onto the top surface of the substrate. The coating solution was allowed to soak into the substrate and then a second sheet of the polyester film was placed on top of the substrate. Excess coating solution was removed by rolling a 2.28 kg cylindrical weight over the top of the three-layer sandwich. Ultraviolet (UV) light-initiated functionalization was conducted by irradiating the sandwich using a stand (Classic Manufacturing, Inc.) equipped with 18 bulbs (Sylvania RG2 40W F40/350BL/ECO, 10 bulbs positioned above and 8 bulbs positioned below the substrate, with each bulb 1.17 meters (46 inches) long and spaced 5.1 cm (2 inches) on center). The substrate was placed on a glass plate positioned in the stand with a bulb to substrate distance of 3.5 cm. The irradiation time was 30 minutes. Following irradiation, the polyester sheets were removed.

The resulting substrate functionalized with covalently attached thiocarbonylthio containing groups (—S—C(S)OCH$_2$CH$_3$) was placed in a 250 mL polyethylene bottle for washing. The bottle was filled with acetone, sealed, and shaken for 30 minutes. The wash solution was decanted. The wash procedure was repeated two more times and then the functionalized substrate was air dried. A sample of the functionalized substrate was analyzed by combustion ion chromatography and the result is reported in Table 4.

Preparative Example 14

The same procedure as described in Preparative Example 13 was followed with the exception that the irradiation time was 15 minutes, instead of 30 minutes. A sample of the functionalized substrate was analyzed by combustion ion chromatography and the result is reported in Table 4.

Preparative Example 15

The same procedure as described in Preparative Example 13 was followed with the exception that the irradiation time was 10 minutes, instead of 30 minutes. A sample of the functionalized substrate was analyzed by combustion ion chromatography and the result is reported in Table 4.

Preparative Example 16

The same procedure as described in Preparative Example 13 was followed with the exception that the irradiation time was 5 minutes, instead of 30 minutes. A sample of the functionalized substrate was analyzed by combustion ion chromatography and the result is reported in Table 4.

Preparative Example 17

The same procedure as described in Preparative Example 13 was followed with the exception that the coating solution contained benzophenone (1.0 weight percent) and methyl 2-ethoxycarbothioylsulfanylacetate (2.5 weight percent) in acetone. A sample of the functionalized substrate was analyzed by combustion ion chromatography and the result is reported in Table 5.

Preparative Example 18

The same procedure as described in Preparative Example 13 was followed with the exception that the coating solution contained benzophenone (1.0 weight percent) and methyl 2-ethoxycarbothioylsulfanylacetate (7.5 weight percent) in acetone. A sample of the functionalized substrate was analyzed by combustion ion chromatography and the result is reported in Table 5.

Preparative Example 19

The same procedure as described in Preparative Example 13 was followed with the exception that the coating solution contained benzophenone (3.0 weight percent) and methyl 2-ethoxycarbothioylsulfanylacetate (5.0 weight percent) in acetone. A sample of the functionalized substrate was analyzed by combustion ion chromatography and the result is reported in Table 5.

Preparative Example 20

The same procedure as described in Preparative Example 13 was followed with the exception that the coating solution contained benzophenone (3.0 weight percent) and methyl 2-ethoxycarbothioylsulfanylacetate (5.0 weight percent) in acetone. A sample of the functionalized substrate was analyzed by combustion ion chromatography and the result is reported in Table 5.

Preparative Example 21

The same procedure as described in Preparative Example 13 was followed with the exception that the coating solution contained benzophenone (5.0 weight percent) and methyl 2-ethoxycarbothioylsulfanylacetate (2.5 weight percent) in acetone. A sample of the functionalized substrate was analyzed by combustion ion chromatography and the result is reported in Table 5.

Preparative Example 22

The same procedure as described in Preparative Example 13 was followed with the exception that the coating solution contained benzophenone (5.0 weight percent) and methyl 2-ethoxycarbothioylsulfanylacetate (7.5 weight percent) in acetone. A sample of the functionalized substrate was analyzed by combustion ion chromatography and the result is reported in Table 5.

TABLE 4

Effect of Varying Irradiation Time on the Reaction Product (Preparative Examples 13-16)

| Preparative Example Number | Irradiation Time for the Coating Solution (minutes) | Conc. of —S—C(S)OCH$_2$CH$_3$ Groups in the Analytical Sample μmol/gram |
|---|---|---|
| 13 | 30 | 8.4 |
| 14 | 15 | 5.9 |
| 15 | 10 | 5.1 |
| 16 | 5 | 4.3 |

TABLE 5

Effect of Varying Benzophenone and Methyl 2-ethoxycarbothioylsulfanylacetate Concentrations on the Reaction Product (Preparative Examples 17-22)

| Preparative Example Number | Conc. of Benzophenone in the Coating Solution (weight %) | Conc. of methyl 2-ethoxy carbothioylsulfanylacetate in the Coating Solution (weight %) | Conc. of —S—C(S)OCH$_2$CH$_3$ Groups in the Analytical Sample (μmol/gram) |
|---|---|---|---|
| 17 | 1.0 | 2.5 | 6.0 |
| 18 | 1.0 | 7.5 | 5.1 |
| 19 | 3.0 | 5.0 | 7.9 |
| 20 | 3.0 | 5.0 | 6.5 |
| 21 | 5.0 | 2.5 | 8.6 |
| 22 | 5.0 | 7.5 | 5.3 |

Preparative Example 23

An 18 cm×23 cm section of nylon membrane substrate (nylon 6,6 membrane, single reinforced layer nylon three zone membrane, nominal pore size 1.8 micron, 0.165 mm thick, bulk density 0.415 g/cm$^3$, #080ZN from 3M Purification, Inc.) was placed on a sheet of clear polyester film (10 mil thick). A coating solution containing benzophenone (0.5 weight percent) and methyl 2-ethoxycarbothioylsulfanylacetate (2.6 weight percent) in heptane was prepared. Approximately 10-15 mL of the coating solution was pipetted onto the top surface of the substrate. The coating solution was allowed to soak into the substrate and then a second sheet of the polyester film was placed on top of the substrate. Excess coating solution was removed by rolling a 2.28 kg cylindrical weight over the top of the three-layer sandwich. Ultraviolet (UV) light-initiated functionalization was conducted by irradiating the sandwich using a stand (Classic Manufacturing, Inc.) equipped with 18 bulbs (Sylvania RG2 40W F40/350BL/ECO, 10 bulbs positioned above and 8 bulbs positioned below the substrate, with each bulb 1.17 meters (46 inches) long and spaced 5.1 cm (2 inches) on center). The substrate was placed on a glass plate positioned in the stand with a bulb to substrate distance of 3.5 cm. The irradiation time was 60 minutes. Following irradiation, the polyester sheets were removed.

The resulting substrate functionalized with covalently attached thiocarbonylthio containing groups (—S—C(S)OCH$_2$CH$_3$) was placed in a 1000 mL polyethylene bottle for washing. The bottle was filled with acetone, sealed, and shaken for 30 minutes. The wash solution was decanted. The wash procedure was repeated two more times and then the functionalized substrate was air dried. A sample of the functionalized substrate was analyzed by combustion ion chromatography and the result is reported in Table 6.

Preparative Example 24

The same procedure as described in Preparative Example 23 was followed with the exception that the irradiation time was 30 minutes, instead of 60 minutes. A sample of the functionalized substrate was analyzed by combustion ion chromatography and the result is reported in Table 6.

Preparative Example 25

The same procedure as described in Preparative Example 23 was followed with the exception that the irradiation time was 15 minutes, instead of 60 minutes. A sample of the functionalized substrate was analyzed by combustion ion chromatography and the result is reported in Table 6.

Preparative Example 26

The same procedure as described in Preparative Example 23 was followed with the exception that the irradiation time was 10 minutes, instead of 60 minutes. A sample of the functionalized substrate was analyzed by combustion ion chromatography and the result is reported in Table 6.

Preparative Example 27

The same procedure as described in Preparative Example 23 was followed with the exception that the irradiation time was 5 minutes, instead of 60 minutes. A sample of the functionalized substrate was analyzed by combustion ion chromatography and the result is reported in Table 6.

TABLE 6

Effect of Irradiation Time on the Reaction Product (Preparative Examples 23-27)

| Preparative Example Number | Irradiation Time (minutes) | Conc. of —S—C(S)OCH$_2$CH$_3$ Groups in the Analytical Sample (µmol/gram) |
|---|---|---|
| 23 | 60 | 20.7 |
| 24 | 30 | 17.3 |
| 25 | 15 | 14.8 |
| 26 | 10 | 9.5 |
| 27 | 5 | 8.1 |

Preparative Example 28

A 9 cm×11.5 cm section of nylon membrane substrate (nylon 6,6 membrane, single reinforced layer nylon three zone membrane, nominal pore size 1.8 micron, 0.165 mm thick, bulk density 0.415 g/cm$^3$, #080ZN from 3M Purification, Inc.) was placed on a sheet of clear polyester film (10 mil thick). A coating solution containing benzophenone (0.5 weight percent) and (isopropoxycarbothioylsulfanyl)methyl octyl ether (4.0 weight percent) in heptane was prepared. Approximately 2.5-3 mL of the coating solution was pipetted onto the top surface of the substrate. The coating solution was allowed to soak into the substrate and then a second sheet of the polyester film was placed on top of the substrate. Excess coating solution was removed by rolling a 2.28 kg cylindrical weight over the top of the three-layer sandwich. Ultraviolet (UV) light-initiated functionalization was conducted by irradiating the sandwich using a stand (Classic Manufacturing, Inc.) equipped with 18 bulbs (Sylvania RG2 40W F40/350BL/ECO, 10 bulbs positioned above and 8 bulbs positioned below the substrate, with each bulb 1.17 meters (46 inches) long and spaced 5.1 cm (2 inches) on center). The substrate was placed on a glass plate positioned in the stand with a bulb to substrate distance of 3.5 cm. The irradiation time was 60 minutes. Following irradiation, the polyester sheets were removed.

The resulting substrate functionalized with covalently attached thiocarbonylthio containing groups (—S—C(S)OCH(CH$_3$)$_2$) was placed in a 250 mL polyethylene bottle for washing. The bottle was filled with acetone, sealed, and shaken for 30 minutes. The wash solution was decanted. The wash procedure was repeated two more times and then the functionalized substrate was air dried. A sample of the functionalized substrate was analyzed by XRF and the result is reported in Table 7.

Preparative Example 29

The same procedure as described in Preparative Example 28 was followed with the exception that the irradiation time was 30 minutes, instead of 60 minutes. A sample of the functionalized substrate was analyzed by XRF and the result is reported in Table 7.

Preparative Example 30

The same procedure as described in Preparative Example 28 was followed with the exception that the irradiation time was 15 minutes, instead of 60 minutes. A sample of the functionalized substrate was analyzed by XRF and the result is reported in Table 7.

Preparative Example 31

The same procedure as described in Preparative Example 28 was followed with the exception that the irradiation time was 10 minutes, instead of 60 minutes. A sample of the functionalized substrate was analyzed by XRF and the result is reported in Table 7.

TABLE 7

Effect of Irradiation Time on the Reaction Product (Preparative Examples 28-31)

| Preparative Example Number | Irradiation Time (minutes) | Conc. of —S—C(S)OCH(CH$_3$)$_2$ Groups in the Analytical Sample (µmol/gram) |
|---|---|---|
| 28 | 60 | 4.2 |
| 29 | 30 | 2.8 |
| 30 | 15 | 2.4 |
| 31 | 10 | 1.9 |

Preparative Examples 32-36

Six samples (each 9 cm×11.5 cm) of a nylon membrane substrate (nylon 6,6 membrane, single reinforced layer nylon three zone membrane, nominal pore size 1.8 µm, 0.165 mm thick, bulk density 0.415 g/cm$^3$, #080ZN from 3M Purification, Inc) were individually placed in separate polyethylene bags with zip-lock type closures. Six vials were prepared with each vial containing a 5 mL solution of methyl-2-ethoxycarbothioylsulfanyl acetate (2.6 weight percent) in heptane that was sparged by bubbling nitrogen through the solution for 2 minutes. The opened bags and vials were placed in a glove box under a nitrogen atmosphere for 15 minutes. Each bag was sealed, removed from the glove box, and then exposed to e-beam irradiation at a selected dose of either 0.5 Mrad, 1.0 Mrad, 3.0 Mrad, 6.0 Mrad, 9.0 Mrad, or 0.0 Mrad (Control Sample A). Each bag was returned to the glove box and maintained for 5 minutes. Next, each bag was opened and 5 mL of the methyl-2-ethoxycarbothioylsulfanyl acetate solution was added to the substrate. A roller was used to facilitate saturation of the substrate with the solution. The bags were resealed and maintained in the nitrogen atmosphere of the glove box for at least 15 additional minutes. Each substrate was subsequently removed from the bag and individually placed into one of six polyethylene bottles (250 mL). Each bottle was filled with heptane, sealed, and placed on a horizontal roller for 30 minutes in order to wash residual methyl-2-ethoxycarbothioylsulfanyl acetate from the substrate. The wash solvent was decanted. The wash procedure was repeated two more times and then each functionalized substrate was air dried. A sample of each functionalized substrate was analyzed by X-ray fluorescence spectroscopy and the results are reported in Table 8.

TABLE 8

Effect of E-Beam Irradiation Dose on the Reaction Product (Preparative Examples 32-36)

| Preparative Example Number | E-Beam Irradiation (Mrad) | Conc. of —S—C(S)OCH$_2$CH$_3$ Groups in the Analytical Sample (µmol/gram) |
| --- | --- | --- |
| 32 | 0.5 | 10.4 |
| 33 | 1.0 | 12.1 |
| 34 | 3.0 | 19.0 |
| 35 | 6.0 | 18.9 |
| 36 | 9.0 | 23.1 |
| Control Sample A | 0.0 | <0.2* |

*The control sample measured <10 ppm sulfur

Example 1

A coating solution of 4-[[2-methyl-2-(prop-2-enoylamino)propanoyl]amino]butanoic acid, sodium salt (VDM-GABA) in deionized water (0.75 M) was prepared.

The functionalized substrate of Preparative Example 1 (9 cm by 12 cm) was equilibrated for a minimum of 18 hours in a low humidity chamber (Sampia Dry Keeper, Sanplatec Corporation, available from VWR International, Radnor, PA) at a relative humidity (RH) of 20-25 percent prior to being grafted. The functionalized substrate was removed from the chamber and immediately weighed. The functionalized substrate was then placed on a sheet of clear polyester film (10 mil thick) and about 4.5 mL of the coating solution was pipetted onto the top surface of the substrate. The coating solution was allowed to soak into the substrate for about 1 minute, and then a second sheet of clear polyester film (10 mil thick) was placed over the top surface of the substrate. A 2.28 kg cylindrical weight was rolled over the top of the resulting three-layer sandwich (polyester film-functionalized substrate-polyester film) to squeeze out excess coating solution. Ultraviolet (UV)-initiated grafting was conducted by irradiating the sandwich using a UV stand (Classic Manufacturing, Inc., Oakdale, MN) equipped with 18 bulbs (Sylvania RG2 40W F40/350BL/ECO, 10 above and 8 below the substrate, 1.17 meters (46 inches) long, spaced 5.1 cm (2 inches) on center), with an irradiation time of 30 minutes. The polyester sheets were removed and the resulting grafted substrate was placed in a 250 mL polyethylene bottle. The bottle was filled with a saline solution (0.9 weight percent), sealed, and shaken for 30 minutes to wash off any residual monomer or ungrafted polymer. The saline solution was decanted, and the grafted substrate was washed for another 30 minutes with fresh saline solution. The saline washed substrate was further washed with deionized water for 30 minutes followed by a second 30 minute wash using fresh deionized water. The wash water was decanted and the grafted substrate was allowed to dry. Next, the grafted substrate was equilibrated in the low humidity chamber (described above) for a minimum of 18 hours. The grafted substrate was removed from the chamber and immediately weighed. The mass gain from the grafting procedure was used to determine the millimoles of monomer grafted to the substrate by dividing the mass gain by the molecular weight of the monomer. Graft density was calculated by dividing the millimoles of monomer grafted to the substrate by the grams of functionalized substrate used in the grafting procedure. Graft density (GD) is reported as millimoles of monomer grafted per gram of functionalized substrate (mmol/g).

Static IgG binding capacity for the grafted substrate was determined according to the procedure described above. Ligand efficiency was calculated as the quotient of the static IgG binding capacity to the graft density (capacity/GD). The results for graft density, static IgG binding capacity, and ligand efficiency are reported in Table 9.

Examples 2-8

The same grafting procedure as reported in Example 1 was followed using functionalized substrates selected from Preparative Examples 2-4 and 13-16. The results for graft density, static IgG binding capacity, and ligand efficiency are reported in Table 8.

Comparative Example A

A coating solution was prepared by adding the water soluble benzophenone initiator 4-(3-sulfopropyloxy)benzophenone, sodium salt (250 microliters of a 0.1 g/mL solution in deionized water) to 5 mL of a 0.75 M solution of 4-[[2-methyl-2-(prop-2-enoylamino)propanoyl]amino]butanoic acid, sodium salt (VDM-GABA) in deionized water. 4-(3-sulfopropyloxy)benzophenone, sodium salt was prepared essentially as described in Japanese Patent Number 47040913.

A 9 cm×12 cm section of nylon membrane substrate (nylon 6,6 membrane, single reinforced layer nylon three zone membrane, nominal pore size 1.8 micron, 0.165 mm thick, bulk density 0.415 g/cm$^3$, #080ZN from 3M Purification, Inc.) was placed on a sheet of clear polyester film (10 mil thick) and about 4.5 mL of the coating solution was pipetted onto the top surface of the substrate. The procedure of Example 1 was followed with the exception that the irradiation time was 15 minutes, instead of 30 minutes. The results for graft density, static IgG binding capacity, and ligand efficiency are reported in Table 9.

TABLE 9

Examples 1-8 and Comparative Example A

| Example | Functionalized Substrate of | VDM-GABA Irradiation Time (min) | Graft Density (mmol/g) | IgG Capacity (mg/mL) | Ligand Efficiency (capacity/GD) |
| --- | --- | --- | --- | --- | --- |
| 1 | Preparative Example 1 | 30 | 0.157 | 155 | 987 |

TABLE 9-continued

Examples 1-8 and Comparative Example A

| Example | Functionalized Substrate of | VDM-GABA Irradiation Time (min) | Graft Density (mmol/g) | IgG Capacity (mg/mL) | Ligand Efficiency (capacity/GD) |
|---|---|---|---|---|---|
| 2 | Preparative Example 2 | 30 | 0.179 | 179 | 1000 |
| 3 | Preparative Example 3 | 30 | 0.201 | 177 | 880 |
| 4 | Preparative Example 4 | 30 | 0.209 | 172 | 823 |
| 5 | Preparative Example 13 | 30 | 0.126 | 116 | 921 |
| 6 | Preparative Example 14 | 30 | 0.153 | 130 | 850 |
| 7 | Preparative Example 15 | 30 | 0.133 | 117 | 880 |
| 8 | Preparative Example 16 | 30 | 0.137 | 119 | 869 |
| Comparative Example A | | 15 | 0.49 | 169 | 357 |

Examples 9-16

The same grafting procedure as reported in Examples 1-8 was followed with the exception that an extended irradiation time of 60 minutes was used. The results for graft density, static IgG binding capacity, and ligand efficiency are reported in Table 10.

TABLE 10

Examples 9-16

| Example | Functionalized Substrate of | VDM-GABA Irradiation Time (min) | Graft Density (mmol/g) | IgG Capacity (mg/mL) | Ligand Efficiency (capacity/GD) |
|---|---|---|---|---|---|
| 9 | Preparative Example 1 | 60 | 0.190 | 224 | 1179 |
| 10 | Preparative Example 2 | 60 | 0.204 | 200 | 980 |
| 11 | Preparative Example 3 | 60 | 0.246 | 223 | 907 |
| 12 | Preparative Example 4 | 60 | 0.251 | 209 | 833 |
| 13 | Preparative Example 13 | 60 | 0.178 | 176 | 989 |
| 14 | Preparative Example 14 | 60 | 0.181 | 198 | 1094 |
| 15 | Preparative Example 15 | 60 | 0.160 | 170 | 1063 |
| 16 | Preparative Example 16 | 60 | 0.171 | 176 | 1029 |

Examples 17-22

The same grafting procedure as reported in Example 1 was followed using functionalized substrates selected from Preparative Examples 17-22. The results for graft density, static IgG binding capacity, and ligand efficiency are reported in Table 11.

TABLE 11

Example 17-22

| Example | Functionalized Substrate of | VDM-GABA Irradiation Time (min) | Graft Density (mmol/g) | IgG Capacity (mg/mL) | Ligand Efficiency (capacity/GD) |
|---|---|---|---|---|---|
| 17 | Preparative Example 17 | 30 | 0.217 | 149 | 687 |
| 18 | Preparative Example 18 | 30 | 0.213 | 147 | 690 |
| 19 | Preparative Example 19 | 30 | 0.271 | 164 | 605 |
| 20 | Preparative Example 20 | 30 | 0.273 | 168 | 615 |
| 21 | Preparative Example 21 | 30 | 0.280 | 172 | 614 |
| 22 | Preparative Example 22 | 30 | 0.241 | 160 | 664 |

Examples 23-26

The same grafting procedure as reported in Example 1 was followed using functionalized substrates selected from Preparative Examples 5-8. The results for graft density, static IgG binding capacity, and ligand efficiency are reported in Table 12.

TABLE 12

Examples 23-26

| Example | Functionalized Substrate of | VDM-GABA Irradiation Time (min) | Graft Density (mmol/g) | IgG Capacity (mg/mL) | Ligand Efficiency (capacity/GD) |
|---|---|---|---|---|---|
| 23 | Preparative Example 5 | 30 | 0.227 | 166 | 731 |
| 24 | Preparative Example 6 | 30 | 0.267 | 164 | 614 |
| 25 | Preparative Example 7 | 30 | 0.344 | 159 | 462 |
| 26 | Preparative Example 8 | 30 | 0.289 | 162 | 561 |

Examples 27-30

The same grafting procedure as reported in Example 1 was followed using functionalized substrates selected from Preparative Examples 9-12. The results for graft density, static IgG binding capacity, and ligand efficiency are reported in Table 13.

TABLE 13

Examples 27-30

| Example | Functionalized Substrate of | VDM-GABA Irradiation Time (min) | Graft Density (mmol/g) | IgG Capacity (mg/mL) | Ligand Efficiency (capacity/GD) |
|---|---|---|---|---|---|
| 27 | Preparative Example 9 | 30 | 0.342 | 135 | 395 |
| 28 | Preparative Example 10 | 30 | 0.264 | 118 | 447 |
| 29 | Preparative Example 11 | 30 | 0.350 | 119 | 340 |
| 30 | Preparative Example 12 | 30 | 0.463 | 124 | 268 |

Examples 31-34

The grafted substrates of Examples 27-30 were submitted to a second grafting procedure performed according to the procedure described in Example 1. The graft density of all the substrates increased after the second grafting procedure. The results for graft density, static IgG binding capacity, and ligand efficiency are reported in Table 14.

TABLE 14

Examples 31-34

| Example | Functionalized Substrate of | Irradiation Time (min) | Graft Density (mmol/g) | IgG Capacity (mg/mL) | Ligand Efficiency (capacity/GD) |
|---|---|---|---|---|---|
| 31 | Example 27 | 30 | 0.540 | 189 | 350 |
| 32 | Example 28 | 30 | 0.430 | 177 | 412 |
| 33 | Example 29 | 30 | 0.516 | 187 | 362 |
| 34 | Example 30 | 30 | 0.642 | 191 | 298 |

Examples 35-39

The same grafting procedure as reported in Example 1 was followed using functionalized substrates selected from Preparative Examples 23-27. The results for graft density, static IgG binding capacity, and ligand efficiency are reported in Table 15.

TABLE 15

Examples 35-39

| Example | Functionalized Substrate of | VDM-GABA Irradiation Time (min) | Graft Density (mmol/g) | IgG Capacity (mg/mL) | Ligand Efficiency (capacity/GD) |
|---|---|---|---|---|---|
| 35 | Preparative Example 23 | 30 | 0.198 | 147 | 742 |
| 36 | Preparative Example 24 | 30 | 0.216 | 149 | 690 |
| 37 | Preparative Example 25 | 30 | 0.204 | 143 | 701 |
| 38 | Preparative Example 26 | 30 | 0.179 | 132 | 737 |
| 39 | Preparative Example 27 | 30 | 0.133 | 106 | 797 |

Example 40

A coating solution of 4-[[2-methyl-2-(prop-2-enoylamino)propanoyl]amino]butanoic acid, sodium salt (VDM-GABA) in deionized water (0.5 M) was prepared.

The functionalized substrate of Preparative Example 28 (9 cm by 12 cm) was equilibrated for a minimum of 18 hours in a low humidity chamber (Sampia Dry Keeper, Sanplatec Corporation, available from VWR International, Radnor, PA) at a relative humidity (RH) of 20-25 percent prior to being grafted. The functionalized substrate was removed from the chamber and immediately weighed. The functionalized substrate was then placed on a sheet of clear polyester film (10 mil thick) and about 4.5 mL of the coating solution was pipetted onto the top surface of the substrate. The coating solution was allowed to soak into the substrate for about 1 minute, and then a second sheet of clear polyester film (10 mil thick) was placed over the top surface of the substrate. A 2.28 kg cylindrical weight was rolled over the top of the resulting three-layer sandwich (polyester film-functionalized substrate-polyester film) to squeeze out excess coating solution. Ultraviolet (UV)-initiated grafting was conducted by irradiating the sandwich using a UV stand (Classic Manufacturing, Inc., Oakdale, MN) equipped with 18 bulbs (Sylvania RG2 40W F40/350BL/ECO, 10 above and 8 below the substrate, 1.17 meters (46 inches) long, spaced 5.1 cm (2 inches) on center), with an irradiation time of 15 minutes. The polyester sheets were removed and the resulting grafted substrate was placed in a 250 mL polyethylene bottle. The bottle was filled with a saline solution (0.9 weight percent), sealed, and shaken for 30 minutes to wash off any residual monomer or ungrafted polymer. The saline solution was decanted, and the grafted substrate was washed for another 30 minutes with fresh saline solution. The saline washed substrate was further washed with deionized water for 30 minutes followed by a second 30 minute wash using fresh deionized water. The wash water was decanted and the grafted substrate was allowed to dry. Next, the grafted substrate was equilibrated in the low humidity chamber (described above) for a minimum of 18 hours. The grafted substrate was removed from the chamber and immediately weighed. The mass gain from the grafting procedure was used to determine the millimoles of monomer grafted to the substrate by dividing the mass gain by the molecular weight of the monomer. Graft density was calculated by dividing the millimoles of monomer grafted to the substrate by the grams of functionalized substrate used in the grafting procedure. Graft density (GD) is reported as millimoles of monomer grafted per gram of functionalized substrate (mmol/g).

Static IgG binding capacity for the grafted substrate was determined according to the procedure described above. Ligand efficiency was calculated as the quotient of the static IgG binding capacity to the graft density (capacity/GD). The results for graft density, static IgG binding capacity, and ligand efficiency are reported in Table 16.

Examples 41-43

The same grafting procedure as reported in Example 40 was followed using functionalized substrates selected from Preparative Examples 29-32. The results for graft density, static IgG binding capacity, and ligand efficiency are reported in Table 16.

TABLE 16

Examples 40-43

| Example | Functionalized Substrate of | VDM-GABA Irradiation Time (min) | Graft Density (mmol/g) | IgG Capacity (mg/mL) | Ligand Efficiency (capacity/GD) |
|---|---|---|---|---|---|
| 40 | Preparative Example 28 | 15 | 0.155 | 159 | 1026 |
| 41 | Preparative Example 29 | 15 | 0.192 | 176 | 917 |
| 42 | Preparative Example 30 | 15 | 0.154 | 154 | 1000 |
| 43 | Preparative Example 31 | 15 | 0.105 | 112 | 1067 |

Example 44

A 12.5 cm×12.5 cm section of polyethersulfone (PES) membrane substrate (0.8 micron nominal pore size, 0.11 mm thick, Zetapore 8F PH from 3M Purification, Inc.) was placed on a sheet of clear polyester film (10 mil thick).

A first coating solution of methyl 2-ethoxycarbothioylsulfanylacetate (2.6 weight percent) in heptane was prepared and 5-6 mL of the first coating solution was pipetted onto the top surface of the PES substrate. The first coating solution was allowed to soak into the substrate and then a second sheet of the polyester film was placed on top of the substrate. Excess first coating solution was removed by rolling a 2.28 kg cylindrical weight over the top of the three-layer sandwich. Ultraviolet (UV) light-initiated treatment was conducted by irradiating the sandwich for a first irradiation time using a stand (Classic Manufacturing, Inc., Oakdale, MN) equipped with 18 bulbs (Sylvania RG2 40W F40/350BL/ECO, 10 bulbs positioned above and 8 bulbs positioned below the substrate, with each bulb 1.17 meters (46 inches) long and spaced 5.1 cm (2 inches) on center). The substrate was placed on a glass plate positioned in the stand with a bulb to substrate distance of 3.5 cm. The first irradiation time was 60 minutes. Following irradiation, the polyester sheets were removed. The resulting PES substrate functionalized with covalently attached thiocarbonylthio containing groups (—S—C(S)OCH$_2$CH$_3$) was washed three times with fresh portions of heptane and then dried. Next, the functionalized substrate was cut into (6.25 cm×6.25 cm) sections and grafted with a 0.75 M coating solution of 4-[[2-methyl-2-(prop-2-enoylamino)propanoyl]amino]butanoic acid, sodium salt (VDM-GABA) in deionized water. The procedure described in Example 1 was followed with the exception that the coating irradiation time was 15 minutes, instead of 30 minutes. The results for graft density, static IgG binding capacity, and ligand efficiency are reported in Table 17.

Examples 45-48

The same procedure as reported in Example 44 was followed except that the first irradiation time was either 30, 15, 10, or 5 minutes. The results for graft density, static IgG binding capacity, and ligand efficiency are reported in Table 17.

Comparative Example B

A 12.5 cm×12.5 cm section of polyethersulfone (PES) membrane substrate (0.8 micron nominal pore size, 0.11 mm thick, Zetapore 8F PH from 3M Purification, Inc.) was grafted with a 0.75 M coating solution of 4-[[2-methyl-2-(prop-2-enoylamino)propanoyl]amino]butanoic acid, sodium salt (VDM-GABA) in deionized water. The procedure described in Example 1 was followed with the exception that the coating irradiation time was 15 minutes, instead of 30 minutes. The results for graft density, static IgG binding capacity, and ligand efficiency are reported in Table 17.

TABLE 17

Examples 44-48 and Comparative Example B

| Example | First Irradiation Time (min) | VDM-GABA Irradiation Time (min) | Graft Density (mmol/g) | IgG Capacity (mg/mL) | Ligand Efficiency (capacity/GD) |
|---|---|---|---|---|---|
| 44 | 60 | 15 | 0.283 | 228 | 806 |
| 45 | 30 | 15 | 0.264 | 208 | 788 |
| 46 | 15 | 15 | 0.248 | 187 | 754 |
| 47 | 10 | 15 | 0.269 | 197 | 732 |
| 48 | 5 | 15 | 0.229 | 192 | 838 |
| Comparative Example B | none | 15 | 0.397 | 237 | 597 |

Examples 49-51

The same procedure as reported in Examples 44, 46, and 48 was followed except that the concentration of the VDM-GABA coating solution was 0.5 M (instead of 0.75 M) and the VDM-GABA coating irradiation time was 30 minutes (instead of 15 minutes). The results for graft density, static IgG binding capacity, and ligand efficiency are reported in Table 18.

Comparative Example C

A 12.5 cm×12.5 cm section of polyethersulfone (PES) membrane substrate (0.8 micron nominal pore size, 0.11 mm thick, Zetapore 8F PH from 3M Purification, Inc.) was grafted with a 0.5 M coating solution of 4-[[2-methyl-2-(prop-2-enoylamino)propanoyl]amino]butanoic acid, sodium salt (VDM-GABA) in deionized water according to the procedure described in Example 1. The results for graft density, static IgG binding capacity, and ligand efficiency are reported in Table 18.

TABLE 18

Examples 49-51 and Comparative Example C

| Example | First Irradiation Time (min) | VDM-GABA Irradiation Time (min) | Graft Density (mmol/g) | IgG Capacity (mg/mL) | Ligand Efficiency (capacity/GD) |
|---|---|---|---|---|---|
| 49 | 60 | 30 | 0.183 | 202 | 1104 |
| 50 | 15 | 30 | 0.196 | 213 | 1087 |
| 51 | 5 | 30 | 0.197 | 215 | 1091 |
| Comparative Example C | none | 30 | 0.344 | 280 | 814 |

Example 52

A 12.5 cm×12.5 cm section of polyethersulfone (PES) membrane substrate (0.8 micron nominal pore size, 0.11 mm thick, Zetapore 8F PH from 3M Purification, Inc.) was placed on a sheet of clear polyester film (10 mil thick). A first coating solution of tetraethylthiuram disulfide (4.0 weight percent) in toluene was prepared and 5-6 mL of the first coating solution was pipetted onto the top surface of the PES substrate. The first coating solution was allowed to soak into the substrate and then a second sheet of the polyester film was placed on top of the substrate. Excess first coating solution was removed by rolling a 2.28 kg cylindrical weight over the top of the three-layer sandwich. Ultraviolet (UV) light-initiated treatment was conducted by irradiating the sandwich for a first irradiation time using a stand (Classic Manufacturing, Inc., Oakdale, MN) equipped with 18 bulbs (Sylvania RG2 40W F40/350BL/ECO, 10 bulbs positioned above and 8 bulbs positioned below the substrate, with each bulb 1.17 meters (46 inches) long and spaced 5.1 cm (2 inches) on center). The substrate was placed on a glass plate positioned in the stand with a bulb to substrate distance of 3.5 cm. The first irradiation time was 60 minutes. Following irradiation, the polyester sheets were removed. The resulting PES substrate functionalized with covalently attached thiocarbonylthio containing groups (—S—C(S)N(CH$_2$CH$_3$)$_2$) was washed three times with fresh portions of toluene and then dried. Next, the functionalized substrate was cut into (6.25 cm×6.25 cm) sections and grafted with a 0.75 M coating solution of 4-[[2-methyl-2-(prop-2-enoylamino)propanoyl]amino]butanoic acid, sodium salt (VDM-GABA) in deionized water according to the procedure described in Example 1. The results for graft density, static IgG binding capacity, and ligand efficiency are reported in Table 19.

Examples 53-56

The same procedure as reported in Example 52 was followed except that the first irradiation time was either 30, 15, 10, or 5 minutes. The results for graft density, static IgG binding capacity, and ligand efficiency are reported in Table 19.

Comparative Example D

A 12.5 cm×12.5 cm section of polyethersulfone (PES) membrane substrate (0.8 micron nominal pore size, 0.11 mm thick, Zetapore 8F PH from 3M Purification, Inc.) was grafted with a 0.75 M coating solution of 4-[[2-methyl-2-(prop-2-enoylamino)propanoyl]amino]butanoic acid, sodium salt (VDM-GABA) in deionized water according to the procedure described in Example 1. The results for graft density, static IgG binding capacity, and ligand efficiency are reported in Table 19.

TABLE 19

Examples 52-56 and Comparative Example D

| Example | First Irradiation Time (min) | VDM-GABA Irradiation Time (min) | Graft Density (mmol/g) | IgG Capacity (mg/mL) | Ligand Efficiency (capacity/GD) |
| --- | --- | --- | --- | --- | --- |
| 52 | 60 | 30 | 0.180 | 204 | 1133 |
| 53 | 30 | 30 | 0.205 | 220 | 1073 |
| 54 | 15 | 30 | 0.283 | 256 | 905 |
| 55 | 10 | 30 | 0.254 | 248 | 976 |
| 56 | 5 | 30 | 0.261 | 266 | 1019 |
| Comparative Example D | none | 30 | 0.556 | 289 | 519 |

Examples 57-59

The same procedure as reported in Examples 52, 53, and 54 was followed except that the coating irradiation time was 15 minutes (instead of 30 minutes). The results for graft density, static IgG binding capacity, and ligand efficiency are reported in Table 20.

Comparative Example E

A 12.5 cm×12.5 cm section of polyethersulfone (PES) membrane substrate (0.8 micron nominal pore size, 0.11 mm thick, Zetapore 8F PH from 3M Purification, Inc.) was grafted with a 0.75 M coating solution of 4-[[2-methyl-2-(prop-2-enoylamino)propanoyl]amino]butanoic acid, sodium salt (VDM-GABA) in deionized water. The procedure described in Example 1 was followed with the exception that the coating irradiation time was 15 minutes (instead of 30 minutes). The results for graft density, static IgG binding capacity, and ligand efficiency are reported in Table 20.

TABLE 20

Examples 57-59 and Comparative Example E

| Example | First Irradiation Time (min) | VDM-GABA Irradiation Time (min) | Graft Density (mmol/g) | IgG Capacity (mg/mL) | Ligand Efficiency (capacity/GD) |
| --- | --- | --- | --- | --- | --- |
| 57 | 60 | 15 | 0.053 | 153 | 2887 |
| 58 | 30 | 15 | 0.093 | 190 | 2043 |
| 59 | 15 | 15 | 0.175 | 217 | 1240 |
| Comparative Example E | none | 15 | 0.272 | 256 | 941 |

Examples 60-64

The same grafting procedure as reported in Example 1 was followed using functionalized substrates selected from Preparative Examples 32-36. The only change was that the VDM-GABA coating irradiation time was 15 minutes, instead of 30 minutes. The results for graft density, static IgG binding capacity, and ligand efficiency are reported in Table 21.

TABLE 21

Examples 60-64

| Example | Functionalized Substrate of | VDM-GABA Irradiation Time (min) | Graft Density (mmol/g) | IgG Capacity (mg/mL) | Ligand Efficiency (capacity/GD) |
| --- | --- | --- | --- | --- | --- |
| 60 | Preparative Example 32 | 15 | 0.089 | 55 | 618 |
| 61 | Preparative Example 33 | 15 | 0.073 | 61 | 836 |
| 62 | Preparative Example 34 | 15 | 0.146 | 117 | 801 |
| 63 | Preparative Example 35 | 15 | 0.150 | 114 | 760 |
| 64 | Preparative Example 36 | 15 | 0.223 | 158 | 708 |

What is claimed is:

1. An article comprising a plurality of polymeric chains grafted to a solid polymeric substrate, the article being a reaction product of a reaction composition after exposure to actinic radiation, the reaction composition comprising:
   a) the solid polymeric substrate having a plurality of thiocarbonylthio-containing groups, wherein each thiocarbonylthio-containing group is covalently bonded directly to a carbon atom in a polymeric backbone of the solid polymeric substrate; and
   b) a radically polymerizable monomer composition comprising a first monomer, the first monomer having (a) at least one ethylenically unsaturated group, (b) at least one ligand functional group that is an acidic group, basic group, or salt thereof, and (c) a spacer group that directly links the at least one ethylenically unsaturated group and the at least one ligand functional group by a chain having at least six catenated atoms; and
   wherein the reaction product after exposure to actinic radiation comprises a plurality of grafted polymeric chains comprising monomeric units derived from the first monomer, each polymeric chain being covalently attached directly to a carbon atom in the polymeric backbone of the solid polymeric substrate and wherein at least some of the grafted polymeric chains are terminated by a thiol or by a thiocarbonylthio-containing group covalently attached to a terminal carbon atom of a terminal monomeric unit in the polymeric chain.

2. The article of claim 1, wherein the thiocarbonylthio-containing groups are of formula —S—C(=S)—R$^1$ wherein
group R$^1$ in the thiocarbonylthio-containing group is selected to be an alkoxy, aralkyloxy, alkenyloxy or N(R$^4$)$_2$; and
each R$^4$ is an alkyl or two adjacent R$^4$ groups are combined with the nitrogen to which they are both attached to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic.

3. The article of claim 1, wherein the first monomer is of Formula (IV):

CH$_2$=CR$^{21}$—C(=O)—X$^1$—R$^{22}$—[Z—R$^{22}$]$_n$-L  (IV)

wherein
R$^{21}$ is selected from hydrogen, alkyl, cycloalkyl, aryl, and combinations thereof;
R$^{22}$ is a (hetero)hydrocarbylene;
X$^1$ is O or NR$^{23}$;
R$^{23}$ is selected from hydrogen or hydrocarbyl;
Z is heterohydrocarbylene including at least one hydrogen bond donor, at least one hydrogen bond acceptor, or a combination thereof;
n is an integer of 0 or 1; and
L is a ligand functional group comprising an acidic group, a basic group, or salt thereof.

4. The article of claim 3, wherein n is equal to 1, Z is C(=O)—X$^2$ where X$^2$ is oxy or NR$^{23}$, and the first monomer of Formula (IV) is of Formula (IV-1)

CH$_2$=CR$^{21}$—C(=O)—NH—R$^{22}$—C(=O)—X$^2$—R$^{22}$-L  (IV-1).

5. The article of claim 3, wherein n is equal to 1, Z is NH—C(=O)—X$^2$ where X$^2$ is oxy or NR$^{23}$, and the first monomer of Formula (IV) is of Formula (IV-2)

CH$_2$=CR$^{21}$—C(=O)—X$^1$—R$^{22}$—NH—C(=O)—X$^2$—R$^{22}$-L  (IV-2).

6. The article of claim 3, wherein n is equal to 1, Z is C(=O)—NR$^{23}$, X$^1$ is NR$^{23}$, L is of formula NR$^{24}$—[C(=NR$^{24}$)—NR$^{24}$]$_m$R$^{25}$ where m is 1 or 2, R$^{24}$ is hydrogen or hydrocarbyl, R$^{25}$ is hydrogen, hydrocarbyl, or N(R$^{24}$)$_2$, and the first monomer is of Formula (IV-3)

CH$_2$=CR$^{21}$—C(=O)—NH—R$^{22}$—C(=O)—NR$^{23}$—R$^{22}$—NR$^{24}$—[C(=NR$^{24}$)—NR$^{24}$]$_m$R$^{25}$  (IV-3).

7. The article of claim 3, wherein n is equal to 1, Z is NH—C(=O)—NR$^{23}$, L is of formula NR$^{24}$—[C(=NR$^{24}$)—NR$^{24}$]$_m$R$^{25}$ where m is 1 or 2, R$^{24}$ is hydrogen or hydrocarbyl, R$^{25}$ is hydrogen, hydrocarbyl, or N(R$^{24}$)$_2$, and the first monomer of Formula (IV) is of Formula (IV-4)

CH$_2$=CR$^{21}$—C(=O)—X$^1$—R$^{22}$—NH—C(=O)—NR$^{23}$—R$^{22}$—NR$^{24}$—[C(=NR$^{24}$)—NR$^{24}$]$_m$—R$^{25}$  (IV-4).

8. The article of claim 7, wherein the solid polymeric substrate is porous.

9. The article of claim 1, wherein the solid polymeric substrate is a membrane or non-woven substrate.

10. The article of claim 1, wherein the article is a reaction product of a functionalized substrate having thiocarbonylthio-containing groups directly and covalently attached to the solid polymeric substrate with the radically polymerizable monomer composition.

11. An article comprising a plurality of polymeric chains grafted to a solid polymeric substrate, the article being a reaction product of a reaction composition after exposure to actinic radiation, the reaction composition comprising:
a) a solid polymeric substrate having a plurality of thiocarbonylthio-containing groups, wherein each thiocarbonylthio-containing group is covalently bonded directly to a carbon atom in a polymeric backbone of the solid polymeric substrate, wherein each thiocarbonylthio-containing group that is covalently bonded to the solid polymeric substrate is of formula

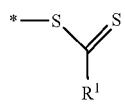

wherein
R$^1$ is an alkoxy, aralkyloxy, alkenyloxy or N(R$^4$)$_2$; and
each R$^4$ is an alkyl or two adjacent R$^4$ groups are combined with the nitrogen to which they are both attached to form a first heterocyclic ring having 1 to 3 heteroatoms selected from nitrogen, oxygen, and sulfur, the first heterocyclic ring being saturated or unsaturated and optionally fused to one or more second rings that are carbocyclic or heterocyclic; and
an asterisk (*) shows the attachment site to a carbon atom in the polymeric backbone of the solid polymeric substrate; and
b) a radically polymerizable monomer composition comprising a first monomer, the first monomer being of Formula (IV)

CH$_2$=CR$^{21}$—C(=O)—X$^1$—R$^{22}$—[Z—R$^{22}$]$_n$-L  (IV)

wherein
R$^{21}$ is selected from hydrogen, alkyl, cycloalkyl, aryl, and combinations thereof;
R$^{22}$ is a (hetero)hydrocarbylene;
X$^1$ is O or NR$^{23}$;
R$^{23}$ is selected from hydrogen or hydrocarbyl;
Z is heterohydrocarbylene including at least one hydrogen bond donor, at least one hydrogen bond acceptor, or a combination thereof;
n is an integer of 0 or 1; and
L is a ligand functional group comprising an acidic group, a basic group, or salt thereof; and
wherein the reaction product after exposure to actinic radiation comprises a plurality of grafted polymeric chains comprising monomeric units derived from the first monomer, each polymeric chain being covalently attached directly to a carbon atom in a polymeric backbone of the solid polymeric substrate and wherein at least some of the grafted polymeric chains are terminated by a thiol or by a thiocarbonylthio-containing group, wherein the thiol or the thiocarbonylthio-containing group is covalently attached to a terminal carbon atom of a terminal monomeric unit in the polymeric chain.

12. An article comprising
a) a solid polymeric substrate; and
b) a plurality of polymeric chains being covalently attached directly to a carbon atom in a polymeric backbone of the solid polymeric substrate, wherein each polymeric chain comprises monomeric units derived from a first monomer of Formula (IV)

$$CH_2\text{—}CR^{21}\text{—}C(\text{=}O)\text{—}X^1\text{—}R^{22}\text{—}[Z\text{—}R^{22}]_n\text{-}L \quad (IV)$$

wherein
- $R^{21}$ is selected from hydrogen, alkyl, cycloalkyl, aryl, and combinations thereof;
- $R^{22}$ is a (hetero)hydrocarbylene;
- $X^1$ is O or $NR^{23}$;
- $R^{23}$ is selected from hydrogen or hydrocarbyl;
- Z is heterohydrocarbylene including at least one hydrogen bond donor, at least one hydrogen bond acceptor, or a combination thereof;
- n is an integer of 0 or 1; and
- L is a ligand functional group comprising an acidic group, a basic group, or salt thereof; and wherein at least some of the grafted polymeric chains are terminated by a thiol or by a thiocarbonylthio-containing group, wherein the thiol or the thiocarbonylthio-containing group is covalently attached to a terminal carbon atom of a terminal monomeric unit in the polymeric chain.

* * * * *